US005646176A

United States Patent [19]
Golik et al.

[11] Patent Number: 5,646,176
[45] Date of Patent: Jul. 8, 1997

[54] PHOSPHONOOXYMETHYL ETHERS OF TAXANE DERIVATIVES

[75] Inventors: Jerzy Golik, Southington; Dolatrai Vyas, Madison; John J. Wright, Guilford; Henry Wong, Durham; John F. Kadow, Wallingford, all of Conn.; John K. Thottathil, Robbinsville; Wen-Sen Li, Marlboro, both of N.J.; Murray A. Kaplan, Syracuse; Robert K. Perrone, Liverpool, both of N.Y.; Mark D. Wittman, Cheshire, Conn.

[73] Assignee: Bristol-Myers Squibb Company, Princeton, N.J.

[21] Appl. No.: 445,360

[22] Filed: May 19, 1995

Related U.S. Application Data

[63] Continuation of Ser. No. 245,119, May 17, 1994, abandoned, which is a continuation-in-part of Ser. No. 154,840, Nov. 24, 1993, abandoned, which is a continuation-in-part of Ser. No. 108,015, Aug. 17, 1993, abandoned, which is a continuation-in-part of Ser. No. 996,445, Dec. 24, 1992, abandoned.

[51] Int. Cl.$^6$ .................. A61K 31/38; C07D 305/14
[52] U.S. Cl. .................. 514/444; 514/449; 514/471; 549/60; 549/214; 549/220; 549/472; 549/473; 549/510; 549/511
[58] Field of Search .................. 514/444, 449, 514/471; 549/60, 214, 220, 472, 473, 510, 511

[56] References Cited

U.S. PATENT DOCUMENTS

| | | |
|---|---|---|
| 4,814,470 | 3/1989 | Colin et al. .................. 514/449 |
| 4,876,399 | 10/1989 | Holton et al. .................. 568/817 |
| 4,942,184 | 7/1990 | Haugwitz et al. .................. 514/449 |
| 4,960,790 | 10/1990 | Stella et al. .................. 514/449 |
| 5,059,699 | 10/1991 | Kingston et al. .................. 549/511 |
| 5,175,315 | 12/1992 | Holton .................. 549/510 |
| 5,227,400 | 7/1993 | Holton et al. .................. 514/444 |
| 5,229,526 | 7/1993 | Holton .................. 549/213 |
| 5,243,045 | 9/1993 | Holton et al. .................. 544/60 |
| 5,248,796 | 9/1993 | Chen et al. .................. 549/510 |
| 5,250,683 | 10/1993 | Holton et al. .................. 544/60 |
| 5,283,253 | 2/1994 | Holton et al. .................. 514/444 |
| 5,284,864 | 2/1994 | Holton et al. .................. 514/449 |
| 5,284,865 | 2/1994 | Holton et al. .................. 514/449 |
| 5,294,637 | 3/1994 | Chen et al. .................. 514/449 |

FOREIGN PATENT DOCUMENTS

| | | |
|---|---|---|
| 522958A1 | 1/1993 | European Pat. Off. . |
| 524093A1 | 1/1993 | European Pat. Off. . |
| 558959A1 | 9/1993 | European Pat. Off. . |
| 233663 | 9/1992 | New Zealand . |
| 235993 | 10/1992 | New Zealand . |
| 237172 | 2/1993 | New Zealand . |
| 237173 | 7/1993 | New Zealand . |
| 239377 | 9/1993 | New Zealand . |
| 243548 | 7/1994 | New Zealand . |
| 240698 | 8/1994 | New Zealand . |
| 241312 | 9/1994 | New Zealand . |
| 243972 | 11/1994 | New Zealand . |
| 244754 | 3/1995 | New Zealand . |
| WO 92/09589 | 6/1992 | WIPO . |
| WO 93/02064 | 2/1993 | WIPO . |
| WO 93/06079 | 4/1993 | WIPO . |
| WO 93/06093 | 4/1993 | WIPO . |

OTHER PUBLICATIONS

Gunda I. Georg et al, "Novel Biologically Active Taxol Analogues: Baccatin III 13–(N–(p–Chlorobenzoyl)–(2'R, 3'S)–3'–phenylisoserinate) and Baccatin III 13–(N–benzoyl–(2'R, 3's)–3'–(p–chlorophynyl)isoserinate)," Bioorganic and Medicinal Chemistry Letters, vol. 2, No. 4, pp. 295–298, 1992.

Gunda I. Georg et al, "Semisynthesis and Biological Activity of Taxol Analogues: Baccatin III 13–( N–benzoyl–(2'R, 3'S)–3'–(p–tolyl)isoserinate), Baccatin III 13–( N–( p–toluoyl)–(2'R,3'S)–3'–(phenylisoserinate), Baccatin III 13–( N–benzoyl–(2'R, 3'S)–3'–(p–trifluoromethylphenyl)isoserinate), and Baccatin III 13–(N–( p–trifluoromethylbenzoyl)–(2'R, 3'S)–3'–phenylisoserinate)," Bioorganic and Medicinal Chemistry Letters, vol. 2, No. 12, pp. 1751–1754, 1992.

Gunda I. Georg et al, "Synthesis of Biologically Active Taxol Analogues with Modified Phenylisoserine Side Chains," Journal of Medicinal Chemistry, vol. 35, pp. 4230–4237, 1992.

F. Gueritte–Voegelein et al, "Relationships between the Structure of Taxol Analogues and Their Antimitotic Activity," Journal of Medicinal Chemistry, vol. 34, pp. 992–998, 1991.

D.G.I. Kingston, et al, "The Chemistry of Taxol, A Clinically Useful Anticancer Agent", Journal of Natural Products, vol. 53, No. 1, pp. 1–12, 1990.

Larry L. Klein, "Synthesis of 9–Dihydrotaxol: A Novel Bioactive Taxane", Tetrahedron Letters, vol. 34, No. 13, pp. 2047–2050, 1993.

Julio C. Medina et al, "A Mild Method for the Conversion of Alcohols to Methylthiomethyl Ethers," Tetrahedron Letters, vol. 29, No. 31, pp. 3773–3776, 1988.

K.C. Nicolaou, et al, "Design, synthesis and biological activity of protaxols," Nature, vol. 364, Jul. 29, 1993, pp. 464–466.

Iwao Ojima et al, "Efficient and Practical Asymmetric Synthesis of the Taxol C–13 Side Chain, N–Benzoyl–(2 R,3 S)–3–phenylisoserine, and Its Analogues via Chiral 3–Hydroxy–4–aryl–β–lactams through Chiral Ester Enolate–Imine Cyclocondensation," Journal of Organic Chemistry, vol. 56, pp. 1681–1683, 1991.

(List continued on next page.)

Primary Examiner—Ba K. Trinh
Attorney, Agent, or Firm—Mollie M. Yang; William T. Han; Samuel J. DuBoff

[57] ABSTRACT

The present invention concerns antitumor compounds. More particularly, the invention provides novel taxane derivatives, pharmaceutical compositions thereof, and their use as antitumor agents.

43 Claims, No Drawings

OTHER PUBLICATIONS

Iwao Ojima et al, "New and Efficient Approaches to the Semisynthesis of Taxol and Its C–13 Side Chain Analogs by Means of β–Lactam Synthon Method," Tetrahedron, vol. 48, No. 34, pp. 6985–7012, 1992.

Iwao Ojima et al, "New and Efficient Routes to Norstatine and Its Analogs with High Enantiomeric Purity by β–Lactam Synthon Method," Tetrahedron Letters, vol. 33, No. 39, pp. 5737–5740, 1992.

Muhammad Safadi, et al, "Phosphoryloxymethyl Cabamates and Carbonates—Novel Water–Soluble Prodrugs for Amines and Hindered Alcohols," Pharmaceutical Research, vol. 10, No. 9, pp. 1350–1355, 1993.

G.H. Veeneman et al, "An Efficient Approach to the Synthesis of Thymidine Derivatives Containing Phosphate–Isosteric Methylene Acetal Linkages," Tetrahedron, vol. 47, No. 8, pp. 1547–1562, 1991.

Dolatrai M. Vyas, et al, "Synthesis and Antitumor Evaluations of Water Soluble Taxol Phosphates," Bioorganic & Medicinal Chemistry Letters, vol. 3, No. 6, pp. 1357–1360, 1993.

N. Gerber, et al., "Safety, Tolerance and Pharmacokinetics of Intravenous Doses of the Phosphate Ester of 3–Hydroxymethyl–5,5–Diphenylhydantoin: A New Prodrug of Phenytoin", J. Clin. Pharmacol., vol. 28, pp. 1023–1032, 1988.

Albert S. Kearney and Valentino J. Stella, "Hydrolysis of Pharmaceutically Relevant Phosphate Monoester Monoanions: Correlation to an Established Structure– Relativity Relationship", Journal of Pharmaceutical Sciences, vol. 82, No. 1, pp. 69–72, Jan., 1993.

Theodora W. Greene and Peter G.M. Wuts, "Productive Groups in Organic Synthesis", Second Edition, pp. 10–12, 14, and 413, John Wiley & Sons, Inc., USA, 1991.

Greene et al, "Protective Groups in Organic Synthesis", 2nd edition, pp. 10–12, 14 and 413, 1991.

PHOSPHONOOXYMETHYL ETHERS OF TAXANE DERIVATIVES

CROSS-REFERENCE TO RELATED APPLICATION(S)

This application is a continuation of U.S. Ser. No. 08/245,119 filed May 17, 1994, now abandoned which is a continuation-in-part of U.S. Ser. No. 08/154,840 filed Nov. 24, 1993, now abandoned which is a continuation-in-part of U.S. Ser. No. 08/108,015 filed Aug. 17, 1993, now abandoned, which in turn is a continuation-in-part of U.S. Ser. No. 07/996,455 filed Dec. 24, 1992, now abandoned.

BACKGROUND OF THE INVENTION

1. Field of the Invention

The present invention concerns antitumor compounds. More particularly, the invention provides novel taxane derivatives, pharmaceutical compositions thereof, and their use as antitumor agents.

2. Background Art

Taxol® (paclitaxel) is a natural product extracted from the bark of Pacific yew trees, *Taxus brevifolia*. It has been shown to have excellent antitumor activity in in vivo animal models, and recent studies have elucidated its unique mode of action, which involves abnormal polymerization of tubulin and disruption of mitosis. It was recently approved for the treatment of ovarian cancer; and studies involving breast, colon, and lung cancers have shown promising results. The results of paclitaxel clinical studies are reviewed in Rowinsky and Donehower, "The Clinical Pharmacology and Use of Antimicrotubule Agents in Cancer Chemotherapeutics" *Pharmac. Ther.*, 52:35–84, 1991.

Recently, a semi-synthetic analog of paclitaxel named Taxotere® has also been found to have good antitumor activity in animal models. Taxotere® is also currently undergoing clinical trials in Europe and the United States. The structures of paclitaxel and Taxotere® are shown below; the conventional numbering system of the paclitaxel molecule is provided.

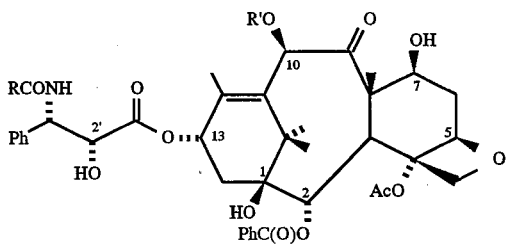

Taxol®: R=Ph; R'=acetyl
Taxotere®: R=t-butoxy; R'=hydrogen

One drawback of paclitaxel is its very limited water solubility requiring it to be formulated in nonaqueous pharmaceutical vehicles. One commonly used carrier is Cremophor EL which may itself have undesirable side effects in man. Accordingly, a number of research teams have prepared water-soluble derivatives of paclitaxel which are disclosed in the following references:

(a) Haugwitz et al, U.S. Pat. No. 4,942,184;
(b) Kingston et al, U.S. Pat. No. 5,059,699;
(c) Stella et al, U.S. Pat. No. 4,960,790;
(d) European Patent Application 0,558,959 A1 published Sep. 8, 1993;
(e) Vyas et al, *Bioorganic & Medicinal Chemistry Letters*, 1993, 3:1357–1360; and
(f) Nicolaou et al, *Nature*, 1993, 364:464–466

Compounds of the present invention are phosphonooxymethyl ethers of taxane derivatives and pharmaceutically acceptable salts thereof. The water solubility of the salts facilitates preparation of pharmaceutical formulations.

SUMMARY OF THE INVENTION

The present invention relates to taxane derivatives having the formula (A):

$$T\text{-}[OCH_2(OCH_2)_m OP(O)(OH)_2]_n \qquad (A)$$

wherein T is a taxane moiety bearing on the C13 carbon atom a substituted 3-amino-2-hydroxypropanoyloxy group; n is 1, 2 or 3; m is 0 or an integer from 1 to 6 inclusive; or a pharmaceutically acceptable salt thereof.

Another aspect of the present invention provides taxane derivatives having the formula (B):

$$T'\text{-}[OCH_2(OCH_2)_m SCH_3]_n \qquad (B)$$

wherein T' is T in which non-reacting hydroxy groups have been blocked, m and n are as defined under formula (A).

Yet another aspect of the present invention provides intermediates having the formula (C):

$$T'\text{-}[OCH_2(OCH_2)_m OP(O)(OR^y)_2]_n \qquad (C)$$

wherein T', m and n are as defined under formula (A), and $R^y$ is a phosphono protecting group.

Another aspect of the present invention provides compounds of the formula (D):

$$13\text{-}OH\text{-}txn\text{-}[OCH_2(OCH_2)_m SCH_3]_n \qquad (D)$$

wherein m and n are as defined above; and txn is a taxane moiety; or a C13 metal alkoxide thereof.

Another aspect of the present invention provides a method for inhibiting tumor in a mammalian host which comprises administering to said mammalian host an antitumor effective amount of a compound of formula (A).

Further aspect of the present invention provides a method for inhibiting tumor in a mammalian host which comprises administering to said mammalian host an antitumor effective amount of a compound of the formula (B'):

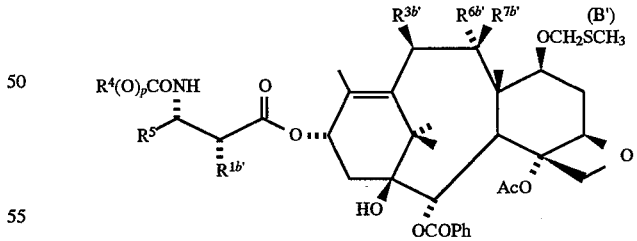

wherein $R^{1b'}$ is hydroxy, —OC(O)$R^x$ or —OC(O)O$R^x$; $R^{3b'}$ is hydrogen, hydroxy, —OC(O)O$R^x$, $C_{1-6}$alkyloxy or —OC(O)$R^x$; one of $R^{6b'}$ or $R^{7b'}$ is hydrogen and the other is hydroxy or $C_{1-6}$ alkanoyloxy; or $R^{6b'}$ and $R^{7b'}$ together form an oxo group; $R^4$ and $R^5$ are independently $C_{1-6}$ alkyl, $C_{2-6}$ alkenyl, $C_{2-6}$ alkynyl, or -Z-$R^6$; Z is a direct bond, $C_{1-6}$ alkyl or $C_{2-6}$ alkenyl; $R^6$ is aryl, substituted aryl, $C_{3-6}$ cycloalkyl or heteroaryl; p is 0 or 1; $R^x$ is $C_{1-6}$ alkyl optionally, substituted with one to six same or different halogen atoms, $C_{3-6}$ cycloalkyl, $C_{2-6}$ alkenyl or hydroxy; or $R^x$ is a radical of the formula

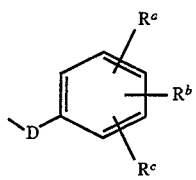

wherein D is a bond or $C_{1-6}$ alkyl; and $R^a$, $R^b$ and $R^c$ are independently hydrogen, amino, $C_{1-6}$ alkylamino, di-$C_{1-6}$alkylamino, halogen, $C_{1-6}$ alkyl, or $C_{1-6}$ alkoxy.

Thus, another aspect of the present invention provides a pharmaceutical composition which comprises an antitumor effective amount of a compound of formula (B') or (A) and a pharmaceutically acceptable carrier.

DETAILED DESCRIPTION OF THE INVENTION

In the application, unless otherwise specified explicitly or in context, the following definitions apply. "Alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. "Alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. "Alkynyl" means a straight or branched carbon chain having at least one carbon-carbon triple bond, and from two to six carbon atoms; examples include ethynyl, propynyl, butynyl, and hexynyl.

"Aryl" means aromatic hydrocarbon having from six to ten carbon atoms; examples include phenyl and naphthyl. "Substituted aryl" means aryl substituted with at least one group selected from $C_{1-6}$ alkanoyloxy, hydroxy, halogen, $C_{1-6}$ alkyl, trifluoromethyl, $C_{1-6}$ alkoxy, aryl, $C_{2-6}$ alkenyl, $C_{1-6}$ alkanoyl, nitro, amino, and amido. "Halogen" means fluorine, chlorine, bromine, and iodine.

"Phosphono-" means the group $—P(O)(OH)_2$ and "phosphonooxymethoxy" or "phosphonooxymethyl ether" means generically the group $—OCH_2(OCH_2)_mOP(O)(OH)_2$. "(Methylthio)thiocarbonyl" means the group $—C(S)SCH_3$. "Methylthiomethyl" (also abbreviated as MTM) generically refers to the group $—CH_2SCH_3$.

"Taxane moiety" (also abbreviated as txn) denotes moieties containing the twenty carbon taxane core framework represented by the structural formula shown below with the absolute configuration.

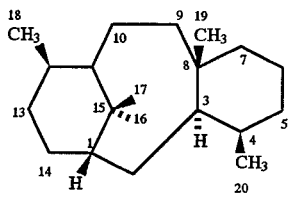

The numbering system shown above is one used in conventional taxane nomenclature, and is followed throughout the application. For example, the notation C1 refers to the carbon atom labelled as "1"; C5–C20 oxetane refers to an oxetane ring formed by the carbon atoms labelled as 4, 5 and 20 with an oxygen atom; and C9 oxy refers to an oxygen atom attached to the carbon atom labelled as "9", said oxygen atom may be an oxo group, α- or β-hydroxy, or α- or β-acyloxy.

"Substituted 3-amino-2-hydroxypropanoyloxy" denotes a residue represented by the formula

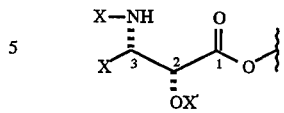

(X is a nonhydrogen group and X' is hydrogen or a nonhydrogen group.) The stereochemistry of this residue is the same as the paclitaxel sidechain. This group is sometimes referred to in the application as the "C13 sidechain."

"Taxane derivative" (abbreviated as T) refers to a compound having a taxane moiety bearing a C13 sidechain.

"Heteroaryl" means a five- or six-membered aromatic ring containing at least one and up to four non-carbon atoms selected from oxygen, sulfur and nitrogen. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings.

"Phosphono protecting groups" means moieties which can be employed to block or protect the phosphono functional group; preferably such protecting groups are those that can be removed by methods that do not appreciably affect the rest of the molecule. Suitable phosphonooxy protecting groups are well known to those skilled in the art and include for example benzyl and allyl groups.

"Hydroxy protecting groups" include, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl.

Additional examples of hydroxy and phosphono protecting groups may be found in standard reference works such as Greene and Wuts, *Protective Groups in Organic Synthesis*, 2d Ed., 1991, John Wiley & Sons, and McOmie, *Protective Groups in Organic Chemistry*, 1975, Plenum Press. Methods for introducing and removing protecting groups are also found in such textbooks.

"Pharmaceutically acceptable salt" means a metal or an amine salt of the acidic phosphono group in which the cation does not contribute significantly to the toxicity or biological activity of the active compound. Suitable metal salts include lithium, sodium, potassium, calcium, barium, magnesium, zinc, and aluminum salts. Preferred metal salts are sodium and potassium salts. Suitable amine salts are for example, ammonia, tromethamine (TRIS), triethylamine, procaine, benzathine, dibenzylamine, chloroprocaine, choline, diethanolamine, triethanolamine, ethylenediamine, glucamine, N-methylglucamine, lysine, arginine, ethanolamine, to name but a few. Preferred amine salts are lysine, arginine, triethanolamine, and N-methylglucamine salts. Even more preferred salt is N-methylglucamine or triethanolamine.

As used herein, the term $—OCH_2(OCH_2)_mOP(O)(OH)_2$ is intended to emcompass both the free acid and its pharmaceutically acceptable salts, unless the context indicates specifically that the free acid is meant.

One aspect of the present invention provides taxane derivatives of the formula (A)

T-[OCH₂(OCH₂)ₘOP(O)(OH)₂]ₙ  (A)

wherein T is a taxane moiety bearing on the C13 carbon atom a substituted 3-amino-2-hydroxypropanoyloxy group; n is an 1, 2 or 3; m is 0, or an integer from 1 to 6 inclusive, or a pharmaceutically acceptable salt thereof.

Another aspect of the present invention provides taxane derivatives having the formula (B)

T-[OCH₂(OCH₂)ₘSCH₃]ₙ  (B)

which are useful in making taxane derivatives of the formula (A).

In one embodiment the taxane moiety contains at least the following functionalities: C1-hydroxy, C2-benzoyloxy, C4-acetyloxy, C5–C20 oxetane, C9-oxy, and C11–C12 double bond.

In a preferred embodiment the taxane moiety is derived from a residue having the formula

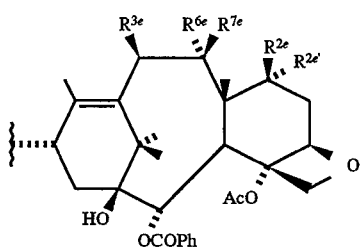

wherein $R^{2e'}$ is hydrogen and $R^{2e}$ is hydrogen, hydroxy, —OC(O)R*, or —OC(O)OR*; $R^{3e}$ is hydrogen, hydroxy, —OC(O)R*, —OC(O)OR* or $C_{1-6}$alkyloxy; one of $R^{6e}$ or $R^{7e}$ is hydrogen and the other is hydroxy or —OC(O)R*; or $R^{6e}$ and $R^{7e}$ together form an oxo group; R* is as defined below.

In another embodiment, the C13 sidechain is derived from a residue having the formula

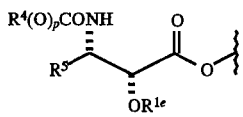

wherein $R^{1e}$ is hydrogen or —C(O)R*, —C(O)OR*; $R^4$ and $R^5$ are independently $C_{1-6}$ alkyl, $C_{2-6}$ alkenyl, $C_{2-6}$ alkynyl, or -Z-$R^6$; Z is a direct bond, $C_{1-6}$ alkyl or $C_{2-6}$ alkenyl; $R^6$ is aryl, substituted aryl, $C_{3-6}$ cycloalkyl, or heteroaryl; and R* is $C_{1-6}$ alkyl optionally substituted with one to six same or different halogen atoms, $C_{3-6}$ cycloalkyl, $C_{2-6}$ alkenyl or hydroxy; or R* is a radical of the formula

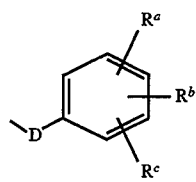

wherein D is a bond or $C_{1-6}$ alkyl; and $R^a$, $R^b$ and $R^c$ are independently hydrogen, amino, $C_{1-6}$ alkylamino, di-$C_{1-6}$alkylamino, halogen, $C_{1-6}$ alkyl, or $C_{1-6}$ alkoxy; p is 0 or 1.

In a preferred embodiment, $R^4$ is $C_{1-6}$ alkyl and p is 1, or $R^4$ is -Z-$R^6$ and p is 0. More preferably, $R^4(O)_p$ is t-butoxy, phenyl, isopropyloxy, n-propyloxy, or n-butoxy.

In another preferred embodiment $R^5$ is $C_{2-6}$alkenyl or -Z-$R^6$ and Z and $R^6$ are as previously defined. More preferably, $R^5$ is phenyl, 2-furyl, 2-thienyl, isobutenyl, 2-propenyl, or $C_{3-6}$cycloalkyl.

In another embodiment, compound of formula (A) may be more specifically represented by the formula (I)

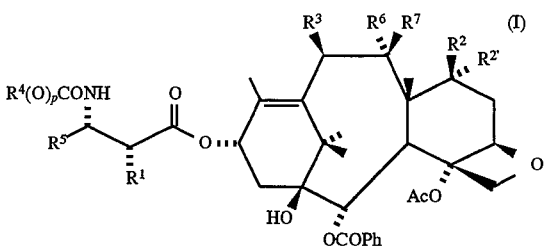

wherein $R^1$ is hydroxy, —OCH₂(OCH₂)ₘOP(O)(OH)₂, —OC(O)R* or —OC(O)OR*; $R^{2'}$ is hydrogen, and $R^2$ is hydrogen, hydroxy, —OCH₂(OCH₂)ₘOP(O)(OH)₂, —OC(O)R* or —OC(O)OR*; $R^3$ is hydrogen, hydroxy, $C_{1-6}$alkyloxy, —OC(O)R*, —OCH₂(OCH₂)ₘOP(O)(OH)₂ or —OC(O)OR*; one of $R^6$ or $R^7$ is hydrogen and the other is hydroxy, $C_{1-6}$ alkanoyloxy, or —OCH₂(OCH₂)ₘOP(O)(OH)₂; or $R^6$ and $R^7$ together form an oxo group; with the proviso that at least one of $R^1$, $R^2$, $R^3$, $R^6$ or $R^7$ is —OCH₂(OCH₂)ₘOP(O)(OH)₂; $R^4$, $R^5$, R*, m and p are as previously defined; or a pharmaceutically acceptable salt thereof.

In compounds of formula (I), examples of R* include methyl, hydroxymethyl, ethyl, n-propyl, isopropyl, n-butyl, isobutyl, chloromethyl, 2,2,2-trichloroethyl, cyclopropyl, cyclobutyl, cyclopentyl, cyclohexyl, ethenyl, 2-propenyl, phenyl, benzyl, bromophenyl, 4-aminophenyl, 4-methylaminophenyl, 4-methylphenyl, 4-methoxyphenyl and the like. Examples of $R^4$ and $R^5$ include 2-propenyl, isobutenyl, 3-furanyl (3-furyl), 3-thienyl, phenyl, naphthyl, 4-hydroxyphenyl, 4-methoxyphenyl, 4-fluorophenyl, 4-trifluoromethylphenyl, methyl, ethyl, n-propyl, isopropyl, n-butyl, isobutyl, t-butyl, ethenyl, 2-propenyl, 2-propynyl, benzyl, phenethyl, phenylethenyl, 3,4-dimethoxyphenyl, 2-furanyl (2-furyl), 2-thienyl, 2-(2-furanyl)ethenyl, 2-methylpropyl, cyclopropyl, cyclobutyl, cyclopentyl, cyclohexyl, cyclohexylmethyl, cyclohexylethyl and the like.

In one embodiment, the present invention provides a preferred group of compounds of formula (I) in which $R^5$ is $C_{2-6}$alkenyl or -Z-$R^6$ and Z and $R^6$ are as previously defined. More preferably, $R^5$ is phenyl, 3-furyl, 3-thienyl, 2-propenyl, isobutenyl, 2-furyl, 2-thienyl, or $C_{3-6}$cycloalkyl.

In another preferred embodiment $R^4$ of compounds of formula (I) is $C_{1-6}$alkyl in which case p is 1; or $R^4$ is -Z-$R^6$ and Z and $R^6$ are as previously defined, and in which case p is 0. More preferably $R^4(O)_p$- is t-butoxy, phenyl, isopropyloxy, n-propyloxy, n-butoxy.

In another preferred embodiment, the present invention provides compounds of formula (I) in which $R^1$ is —OCH₂(OCH₂)ₘOP(O)(OH)₂. In a more preferred embodiment, $R^2$ is hydroxy, —OCH₂(OCH₂)ₘOP(O)(OH)₂, —OC(O)OR* or —OC(O)R*, and R* is preferably $C_{1-6}$ alkyl. In another more preferred embodiment, $R^3$ is hydroxy or acetoxy.

In another embodiment, the present invention provides compound of formula (I) in which $R^2$ is —OCH₂(OCH₂)ₘOP(O)(OH)₂; $R^1$ is hydroxy, —OC(O)R* or —OC(O)OR*; and $R^3$ is hydrogen, hydroxy, acetoxy, —OCH₂(OCH₂)ₘOP(O)(OH)₂ or —OC(O)OR*; and R* is as previously defined. In a more preferred embodiment $R^1$ is hydroxy or —OC(O)OR* and R* is preferably $C_{1-6}$ alkyl; and $R^3$ is hydroxy or acetoxy.

In another preferred embodiment, the present invention provides compound of formula (I) in which $R^3$ is —OCH₂

$(OCH_2)_mOP(O)(OH)_2$; $R^1$ is hydroxy or —$OC(O)OR^x$; $R^{2'}$ is hydrogen, and $R^2$ is hydrogen, hydroxy or —$OC(O)OR^x$; and $R^x$ is as previously defined. In a more preferred embodiment, $R^1$ is hydroxy or —$OC(O)OR^x$, and $R^x$ is preferably $C_{1-6}$ alkyl. In another more preferred embodiment, $R^2$ is hydroxy.

In another preferred embodiment, m is 0, 1 or 2 when the phosphonooxymethoxy group is present on the C7 of the taxane moiety.

The preferred pharmaceutically acceptable salts of a compound of formula (A) are alkali metal salts including lithium, sodium and potassium salts; and amine salts including triethylamine, triethanolamine, ethanolamine, arginine, lysine and N-methylglucamine salts. Even more preferred salts are sodium, triethanolamine, and N-methylglucamine salts.

The most preferred embodiments of taxane derivatives of formula (A) include the following compounds: (1) 7-O-phosphonooxymethylpaclitaxel, (2) 2'-O-(ethyloxycarbonyl)-7-O-phosphonooxymethylpaclitaxel; (3) 2'-O-phosphonooxymethylpaclitaxel; (4) 2',7-bis-O-(phosphonooxymethyl)paclitaxel; (5) 3'-N-debenzoyl-3'-desphenyl-3'-N-(t-butyloxycarbonyl)-3'-(2-furyl)-2'-O-ethyloxycarbonyl-7-O-phosphonooxymethylpaclitaxel; (6) 3'-N-debenzoyl-3'-desphenyl-3'-N-(t-butyloxycarbonyl)-3'-(2-thienyl)-2'-O-ethyloxycarbonyl-7-O-phosphonooxymethylpaclitaxel; (7) 10-desacetyl-3'-N-desbenzoyl-3'-N-(t-butyloxycarbonyl)-10-O-(phosphonooxymethyl)paclitaxel; (8) 2'-O-phosphonooxymethoxymethylpaclitaxel; (9) 2'-O-n-propylcarbonyl-7-O-phosphonooxymethylpaclitaxel; (10) 2'-O-methylcarbonyl-7-O-phosphonooxymethylpaclitaxel; (11) 2'-O-methoxycarbonyl-7-O-phosphonooxymethylpaclitaxel; (12) 2'-O-phosphonooxymethoxymethyl-7-O-phosphonooxymethylpaclitaxel; and their respective pharmaceutically acceptable salts, particularly the sodium, potassium, arginine, lysine, N-methylglucamine, ethanolamine, triethylamine and triethanolamine salts.

Compounds of formula (A) may be prepared from a taxane derivative starting material T-[OH]$_n$ wherein T and n are as previously defined. The identity of T-[OH]$_n$ is not particularly limited so long as there is at least one reactive hydroxy group present on either the taxane moiety or the C13 side chain to allow the formation of phosphonooxymethyl ether linkage. It is to be understood that the reactive hydroxy group may be directly attached to the C13 propanoyloxy backbone (e.g. the 2'-hydroxy group of paclitaxel) or to the taxane core framework (e.g. the 7-hydroxy group of paclitaxel); or it may be present on a substituent on the C13 sidechain, or on a substituent on the taxane core. The reaction sequence shown in Scheme I may be used to prepare compounds of formula (A)

Scheme I

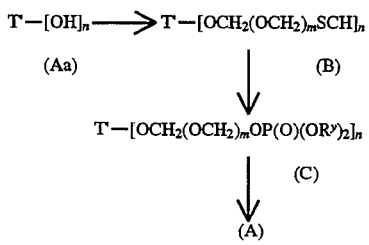

In Scheme I T' is a taxane derivative in which nonreacting hydroxy groups have been blocked; $R^y$ is a phosphono protecting group; n and m are as previously defined. Thus an appropriately protected T' having one or more reactive hydroxy groups is first converted to a corresponding methylthiomethyl ether of formula (B). Using paclitaxel as an example, T' may be paclitaxel itself (to effect 2',7-bismethylthiomethylation), 7-O-triethylsilylpaclitaxel, 7-O-benzyloxycarbonylpaclitaxel, or 2'-O-ethoxycarbonylpaclitaxel. A compound of formula (B) where m is 0 may be prepared by treating T'-[OH]$_n$ with dimethylsulfoxide/acetic anhydride, or with dimethylsulfide and an organic peroxide. These reactions are discussed more fully in a subsequent section.

The MTM ether having one intervening methyleneoxy unit (i.e. compounds of formula (B) where m=1) may be prepared by several possible routes. In one a compound of formula (B) where m=0 is reacted with N-iodosuccinimide (NIS) and methylthiomethanol to extend the chain by one methyleneoxy unit.

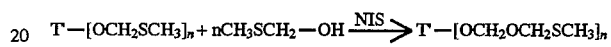

An analogous reaction of an alcohol with methylthiomethyloxy group in the presence of NIS was reported by Veeneman et al, in *Tetrahedron*, 1991, v47, pp. 1547–1562, the relevant portions thereof are hereby incorporated by reference. Silver triflate is preferably used as a catalyst. The compound of methylthiomethanol and its preparation is reported in *Syn. Comm.*, 1986, 16 (13): 1607–1610.

In an alternative method, the T-alkoxide (Ad) generated by treating a compound of formula (Aa) with a base such as n-butyl lithium, lithium diisopropylamide or lithium hexamethyldisilazide, is reacted with chloromethyl methylthiomethyl ether to provide a compound of formula (B) in which m=1.

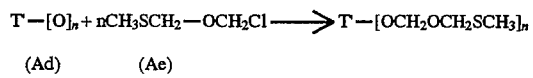

(Ad)   (Ae)

Compound (Ae) is prepared by reacting methylthiomethoxide (obtained from methythiomethanol by treatment with a base such as n-butyl lithium, lithium diisopropylamide or lithium hexamethyldisilazide) with chlor-oiodomethane. Compound (Ae) may also be prepared by treating 1,1'-dichlorodimethylether ($ClCH_2OCH_2Cl$) with a stoichiometric amount or less (e.g. about 0.8 equivalent) of sodium iodide followed by sodium thiomethoxide. 1,1'-Dichlorodimethyl ether is reported in *Ind. J. Chem.*, 1989, 28B, pp. 454–456.

In another method, a compound of formula (Aa) is reacted with bis(MTM)ether, $CH_3SCH_2OCH_2SCH_3$, and NIS to give a compound of formula (B) in which m=1.

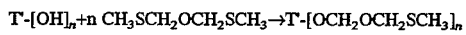

Bis(MTM)ether is prepared by reacting 1,1'-dichlorodimethyl ether with sodium iodide followed by sodium thiomethoxide.

The procedure described above using methylthiomethanol and NIS may be applied to any reagent having an MTM group to extend the chain by one methyleneoxy unit at a time. For example, a compound of formula (B) wherein m=1 can be reacted with methythiomethanol and NIS to provide a compound of formula (B) wherein m=2. The process may be repeated to provide compounds of formula (B) in which m is 3, 4, 5 or 6.

In the second step shown in Scheme I, the methylthiomethyl ether is converted to the corresponding protected phosphonooxymethyl ether. This is accomplished by treating the MTM ether with NIS and protected phosphate HOP(O)(OR$^y$)$_2$. In the third step, the phosphono protecting group and any hydroxy protecting group(s) are removed to provide a compound of formula (A). For example, a suitable phosphono protecting group is benzyl which may be removed by catalytic hydrogenolysis; hydroxy protecting groups such as trialkysilyl may be removed by fluoride ion, trichloroethoxycarbonyl may be removed by zinc. Removal of protecting groups are taught in textbooks such as Green and Wuts, *Protective Groups in Organic Synthesis*, John Wiley & Sons, 1991; and McOmie, *Protective in Organic Chemistry*, Plenum Press, 1973. Both steps are discussed in detail in a later section in the specification.

A variation of the reaction sequence shown in Scheme I is provided in Scheme II.

Scheme II

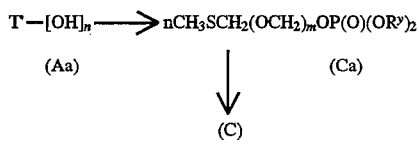

In Scheme II, a compound of formula (Aa) is reacted with a compound of formula (Ca) and NIS to give a compound of formula (C), which is then deblocked to give a compound of formula (A). Compounds of formula (Ca) in which m is 0 may be prepared by first treating methylthiomethanol with a base such as Na, Li or K hexamethyldisilazide to give methylthiomethoxide; the methoxide is then reacted with a protected chlorophosphate such as dibenzyl chlorophosphate to provide the desired compound. Compounds of formula (Ca) in which m is 1 may be prepared by treating CH$_3$SCH$_2$OCH$_2$Cl with a diprotected phosphate salt, e.g. sodium, potassium, tetra(n-butyl)ammonium salts of dibenzyl phosphate; or CH$_3$SCH$_2$OCH$_2$Cl may be first converted to the corresponding iodo compound using sodium iodide prior to reacting with the phosphate salt. Alternatively, compounds of formula (Ca) in which m is 1 may be prepared by treating ClCH$_2$OCH$_2$Cl with sodium iodide followed by sodium thiomethoxide to provide CH$_3$SCH$_2$OCH$_2$SCH$_3$; this compound is then treated with NIS and a diprotected phosphate such as dibenzyl phosphate to give the desired product. Any of the previously mentioned reagents having a MTM group may be extended one methyleneoxy unit at a time by reacting said reagent with methylthiomethanol and NIS.

In another method for preparing a compound of formula (A), T-alkoxide (Ad) is reacted with an iodophosphate as shown in Scheme III.

Scheme III

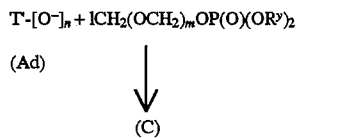

In Scheme III, the iodophosphate compound is obtained by reacting ClCH$_2$(OCH$_2$)$_m$Cl with a diprotected phosphate salt to give ClCH$_2$(OCH$_2$)$_m$OP(O)(OR$^y$)$_2$ which is then treated with sodium iodide to give the desired product.

Yet another method suitable for preparing a subset of compounds of formula (A) in which at least one of the phosphonooxymethoxy groups is linked to the taxane moiety is shown in Scheme IV.

Scheme IV

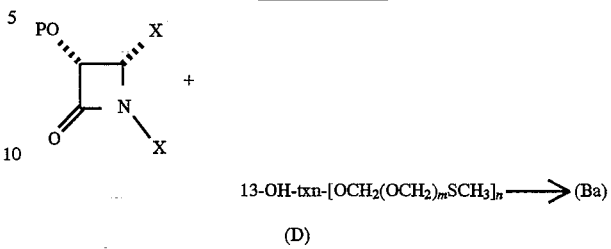

13-OH-txn-[OCH$_2$(OCH$_2$)$_m$SCH$_3$]$_n$ ⟶ (Ba)

(D)

In Scheme IV, m and n are as previously defined; X is a non-hydrogen group, P is a hydroxy protecting group; txn is a taxane moiety. Compounds of formula (D) are taxanes having a 13α-hydroxy group and one or more methylthiomethyl ether linked directly or indirectly to the taxane core; also included are C13 metal alkoxides of formula (D). An example of a compound of formula (D) is 7-O-methylthiomethylbaccatin III:

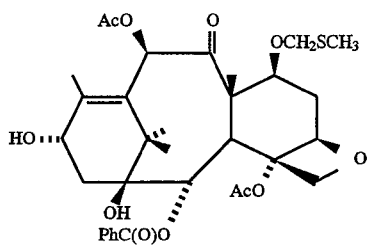

The coupling of the taxane (D) with the azetidinone is analogous to the one shown in Scheme VI, infra; thus the procedure described there for the preparation of a compound of formula (Id) is also applicable to the preparation of a compound of formula (Ba) [i.e. a compound of formula (B) in which at least one of the MTM group is linked directly or indirectly to the taxane moiety], if a compound of formula (D) is used in place of a compound of formula (II) in Scheme VI. The taxane (D) is preferably first converted to a C13 metal alkoxide such as sodium, potassium or lithium alkoxide; lithium alkoxide is preferred. The azetidinone serves as the precursor of the C13 sidechain. After the coupling reaction with a taxane, the hydroxy protecting group P is removed, and if desired, the free hydroxy group on the sidechain may be converted to the MTM ether or derivatized to an ester or a carbonate as herein described.

The azetidinone may be prepared by methods described later which are also methods generally known in the art. Compounds of formula (D) may be prepared by the general procedure described above for the preparation of compounds of formula (B) using a suitably protected taxane. However, more conveniently, they can be obtained from a compound of formula (Ba) by cleaving the 13-sidechain using a borohydride such as sodium or tetrabutylammonium borohydride; for example, 7-O-MTM of paclitaxel is treated with tetrabutylammoniumborohydride to give 7-O-MTM baccatin III.

The general process of Scheme I for the preparation of a compound of formula (A) is more particularly exemplified in Scheme V which illustrates the preparation of a compound of formula (I') (i.e. a compound of formula (I) in which m is 0). The procedure employed in this synthetic sequence is generally applicable to other taxane derivatives not specifically encompassed by formula (I). Furthermore, the procedure in Scheme (V) may be modified in accordance with teachings contained herein by one skilled in the art to arrive at taxane derivatives of formula (A) in which m is 1, 2 or 3.

It is to be understood that in Scheme V as well as elsewhere in the specification, the term "hydroxy protecting group" may encompass suitable carbonates (e.g. —OC(O)OR$^x$ in which R$^x$ does not contain hydroxy); thus, when a carbonate is used as a hydroxy protecting group, it is intended to be removed in a later step to generate the free hydroxy group, otherwise, the carbonate moiety remains as part of the final product.

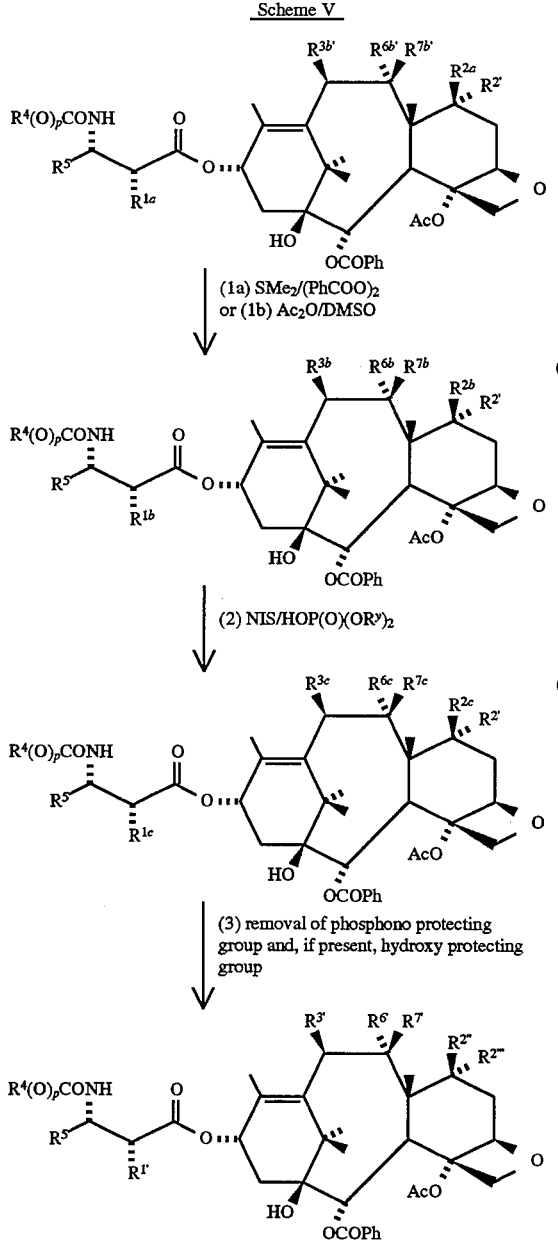

In Scheme V, R$^{1a}$ is hydroxy, protected hydroxy, —OC(O)R$^x$ or —OC(O)OR$^x$; R$^{2'}$ is hydrogen, and R$^{2a}$ is hydrogen, hydroxy, protected hydroxy, —OC(O)R$^x$ or —OC(O)OR$^x$; R$^{3a}$ is hydrogen, hydroxy, protected hydroxy, C$_{1-6}$alkyloxy, —OC(O)R$^x$ or —OC(O)OR$^x$; one of R$^{6a}$ or R$^{7a}$ is hydrogen and the other is hydroxy, protected hydroxy or C$_{1-6}$ alkanoyloxy; or R$^{6a}$ and R$^{7a}$ together form an oxo group; with the proviso that at least one of R$^{1a}$, R$^{2a}$ or R$^{3a}$, R$^{6a}$ or R$^{7a}$ is hydroxy. R$^{1b}$ is hydroxy, protected hydroxy, —OCH$_2$SCH$_3$, —OC(O)R$^x$ or —OC(O)OR$^x$; R$^{2'}$ is hydrogen, and R$^{2b}$ is hydrogen, hydroxy, protected hydroxy, —OCH$_2$SCH$_3$, —OC(O)R$^x$ or —OC(O)OR$^x$; R$^{3b}$ is hydrogen, hydroxy, protected hydroxy, C$_{1-6}$alkyloxy, —OC(O)R$^x$, —OCH$_2$SCH$_3$ or —OC(O)OR$^x$; one of R$^{6b}$ or R$^{7b}$ is hydrogen and the other is hydroxy, protected hydroxy, C$_{1-6}$ alkanoyloxy or —OCH$_2$SCH$_3$; or R$^{6b}$ and R$^{7b}$ together form an oxo group; with the proviso that at least one of R$^{1b}$, R$^{2b}$, R$^{3b}$, R$^{6b}$ or R$^{7b}$ is —OCH$_2$SCH$_3$. R$^{1c}$ is hydroxy, protected hydroxy, —OCH$_2$OP(O)(OR$^y$)$_2$, —OC(O)R$^x$ or —OC(O)OR$^x$; R$^{2'}$ is hydrogen, and R$^{2c}$ is hydrogen, hydroxy, protected hydroxy, —OCH$_2$OP(O)(OR$^y$)$_2$, —OC(O)R$^x$ or —OC(O)OR$^x$; R$^{3c}$ is hydrogen, hydroxy, protected hydroxy, C$_{1-6}$alkyloxy, —OC(O)R$^x$, —OCH$_2$OP(O)(OR$^y$)$_2$ or —OC(O)OR$^x$; one of R$^{6c}$ or R$^{7c}$ is hydrogen and the other is hydroxy, protected hydroxy, C$_{1-6}$ alkanoyloxy or —OCH$_2$OP(O)(OR$^y$)$_2$; with the proviso that at least one of R$^{1c}$, R$^{2c}$, R$^{3c}$, R$^{6c}$ or R$^{7c}$ is —OCH$_2$OP(O)(OR$^y$)$_2$. R$^{1'}$ is hydroxy, —OCH$_2$OP(O)(OH)$_2$, —OC(O)R$^x$ or —OC(O)OR$^x$; R$^{2'''}$ is hydrogen, and R$^{2''}$ is hydrogen, hydroxy, —OCH$_2$OP(O)(OH)$_2$, —OC(O)R$^x$ or —OC(O)OR$^x$; R$^{3'}$ is hydrogen, hydroxy, C$_{1-6}$alkyloxy, —OC(O)R$^x$, —OCH$_2$OP(O)(OH)$_2$ or —OC(O)OR$^x$; one of R$^{6'}$ or R$^{7'}$ is hydrogen and the other is hydroxy, C$_{1-6}$ alkanoyloxy or —OCH$_2$OP(O)(OH)$_2$; with the proviso that at least one of R$^{1'}$, R$^{2''}$, R$^{3'}$, R$^{6'}$ or R$^{7'}$ is —OCH$_2$OP(O)(OH)$_2$. R$^4$, R$^5$, R$^x$, and p are as defined previously, and R$^y$ is a phosphono protecting group.

In the first step, the free hydroxy group of a compound of formula (Ia) is converted to the corresponding methylthiomethyl ether (—OCH$_2$SCH$_3$) group. This conversion may be accomplished by either one of the two procedures (1a—the dimethylsulfide method) and (1b—the dimethylsulfoxide method). The dimethylsulfide method for converting alcohols to methylthiomethyl ethers is reported in Medina et al, Tet. Lett., 1988, pp. 3773-3776, the relevant portions thereof are hereby incorporated by reference. The dimethylsulfoxide method is the well-known reaction commonly known as the Pummerer reaction.

It should be noted that the reactivity of a hydroxy group differs depending on its location on the taxane derivative starting material of formula (Ia). Although in general the 2'-hydroxy group is more reactive in acylation reactions than the 7-hydroxy group which in turn is more reactive than the 10-hydroxy group, it has been found that, surprisingly with the dimethylsulfide method, the 7-hydroxy is more readily converted into the methylthiomethyl ether than the 2'-hydroxy group. The tertiary hydroxy group at C-1 is usually the least reactive. The difference in hydroxy reactivity may be exploited in controlling the site and degree of methylthiomethylation.

Thus with a compound of formula (Ia) wherein R$^{1a}$ and R$^{2a}$ are both hydroxy, the predominant methylthiomethylation product is the corresponding 7-O-methylthiomethyl ether with the dimethylsulfide method. In order to obtain a compound of formula (Ib) wherein R$^{1b}$ is methylthiomethoxy, without also converting the 7-hydroxy group, if present, into a methylthiomethyl ether, the 7-hydroxy group is blocked with a conventional hydroxy protecting group such as triethylsilyl or benzyloxycarbonyl. Similarly, 10-methylthiomethyl ether may be obtained without also converting the 7- and/or 2'-hydroxy groups, if present, when the latter groups are blocked by the same of different hydroxy protecting groups. Even though the 7-hydroxy is the preferential methylthiomethylation site in the dimethylsulfide method, it is still preferable to protect the 2'-hydroxy group if the 7-monomethylthiomethyl ether is the desired product.

Moreover, the reaction conditions may be manipulated to favor the formation of bis- or tris-methylthiomethyl ether taxane derivatives. For example, in the case of paclitaxel, increasing reaction time or using a larger excess of the methylthiomethylating reagents can result in a higher ratio of 2',7-bis(methylthiomethyl) ether paclitaxel in the product mixture.

Returning now to Scheme V, in procedure (1a) a compound of formula (Ia) is treated with dimethylsulfide and an organic peroxide such as benzoyl peroxide. The reaction is carried out in an inert organic solvent such as acetonitrile, methylene chloride and the like at a temperature conducive to product formation; typically the reaction is carried at a temperature range of from about −40° C. to about ambient temperature. Dimethylsulfide and benzoyl peroxide are used in excess relative to the taxane derivative starting material (Ia), and dimethylsulfide is used in excess relative to benzoyl peroxide.

The relative amounts of starting materials used will depend on the degree of methylthiomethylation to be achieved. Thus when one free hydroxy group of the taxane derivative starting material (Ia) is to be converted to the methylthiomethyl ether, dimethylsulfide and benzoyl peroxide may be used in up to 10 fold excess relative to taxane derivative (Ia); and preferably, dimethylsulfide is used in about two to three fold excess relative to benzoyl peroxide. In the case where the starting material (Ia) has both 2'- and 7-hydroxy groups, the amount of 2',7-bis(methylthiomethyl) ether obtained increases with the relative amounts of dimethylsulfide and benzoyl peroxide. When 2',7-bis(methylthiomethyl) ether is the desired product, dimethylsulfide is preferably used in about 15 to about 20 fold excess of the taxane derivative starting material; and benzoyl peroxide is used in about 5 to about 10 fold excess relative to the taxane derivative starting material.

Alternatively, a compound of formula (Ib) may be prepared by reacting a compound of formula (Ia) with dimethylsulfoxide and acetic anhydride (procedure 1b). This procedure is suitable for derivatizing a non-2'-hydroxy group into its methylthiomethyl ether. In procedure (1b), a compound of formula (Ia) is dissolved in dimethylsulfoxide and acetic anhydride is added to the solution. The reaction is usually carried out at room temperature, and for 18–24 hours to produce the monomethylthiomethyl ether.

In the second step of the reaction sequence, the methylthiomethyl ether is converted to the corresponding protected phosphonooxymethyl ether. The methylthiomethyl to protected phosphonooxymethyl conversion may be accomplished by the general method reported in Veeneman et al, Tetrahedron, 1991, v47, pp. 1547–1562, the relevant portions thereof are hereby incorporated by reference. Thus, a compound of formula (Ib) with at least one methylthiomethyl ether group is treated with N-iodosuccinimide and a protected phosphoric acid such as dibenzyl phosphate. The reaction is carried out in an inert organic solvent such as tetrahydrofuran or a halogenated hydrocarbon such as 1,2-dichloroethane or methylene chloride, and optionally in the presence of a dehydrating agent such as molecular sieves. A catalyst such as silver trifluoromethanesulfonate may also be added to accelerate the reaction. The reaction is carried out at a temperature ranging from about 0° C. to about room temperature, preferably at room temperature. N-Iodosuccinimide and the protected phosphoric acid are used in about the same molar equivalent as the methylthiomethylether (Ib), but preferably they are used in slight excess, for example about 1.3 to about 1.5 equivalents relative to compound of formula (Ib).

In the third step of the reaction sequence, the phosphono protecting group and hydroxy protecting group, if present, are removed. The deblocking is accomplished by conventional methods well known in the art such as acid- or base-catalyzed hydrolysis, hydrogenolysis, reduction, and the like. For example, catalytic hydrogenolysis can be used to remove the benzyl phosphono protecting group as well as the benzyloxycarbonyl hydroxy protecting group. Deprotecting methodologies may be found in standard texts such as Greene and Wutz, or McOmie, supra. Needless to say if a compound of formula (Ia) contains hydroxy groups in radical $R^x$, said hydroxy groups are preferably protected with suitable hydroxy protecting groups until deprotected in this last step.

As indicated earlier the procedure in Scheme V may be modified in accordance with the teaching contained herein by one skilled in the art to arrive at taxane derivatives of formula A in which m is 1, 2 or 3. As examples, Schemes Va and Vb specifically illustrate how one skilled in the art can modify the teaching contained herein to arrive at certain compounds of formula A wherein at least one substitutent is —OCH$_2$(OCH$_2$)$_2$OP(O)(OH)$_2$. Similarly other compounds of formula A in which m is 3 can be readily obtaiined.

SCHEME Va

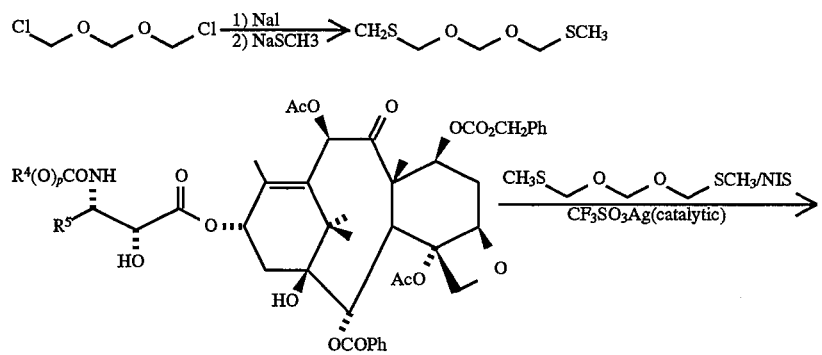

-continued
SCHEME Va
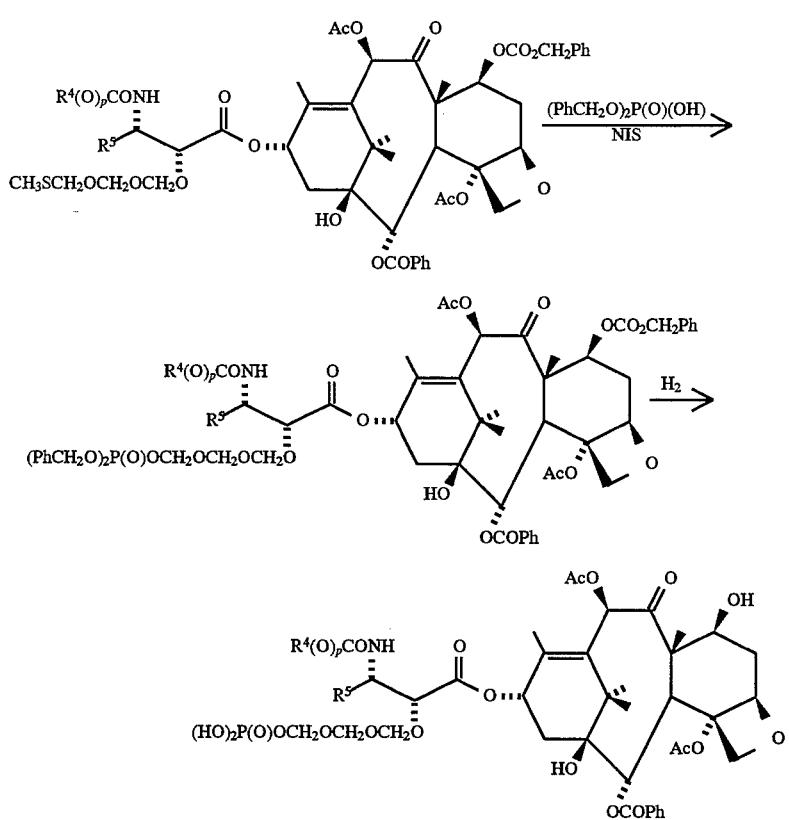
SCHEME Vb
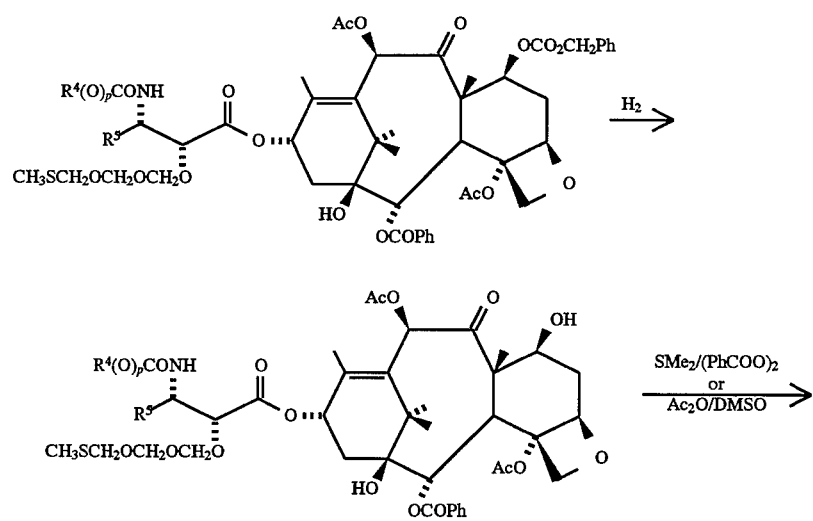

-continued
SCHEME Vb

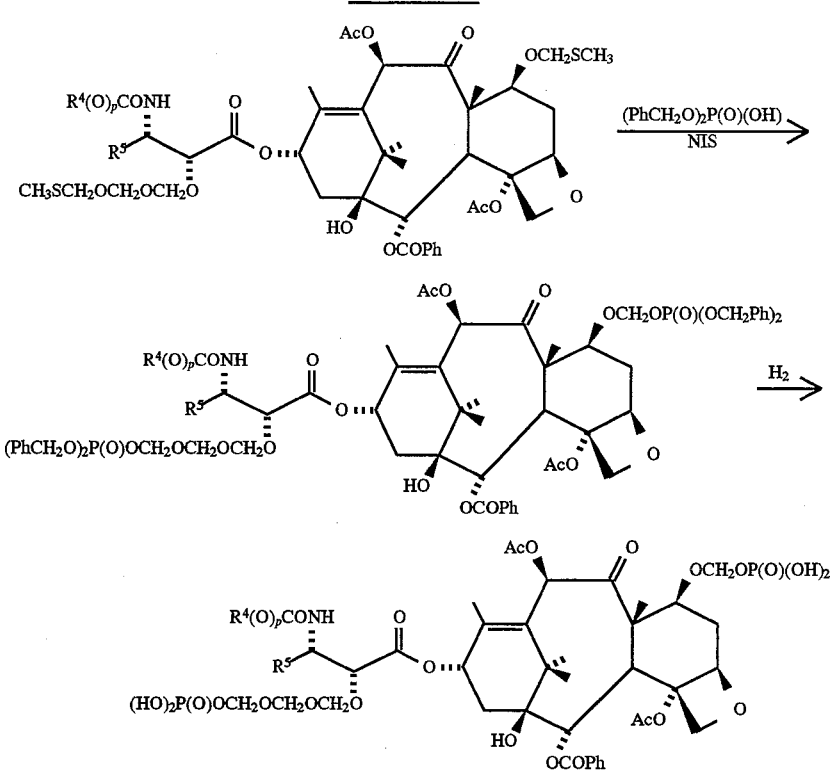

The base salts of a compound of formula (I) may be formed by conventional techniques involving contacting a compound of formula (I) free acid with a metal base or with an amine. Suitable metal bases include hydroxides, carbonates and bicarbonates of sodium, potassium, lithium, calcium, barium, magnesium, zinc, and aluminum; and suitable amines include triethylamine, ammonia, lysine, arginine, N-methylglucamine, ethanolamine, procaine, benzathine, dibenzylamine, tromethamine (TRIS), chloroprocaine, choline, diethanolamine, triethanolamine and the like. The base salts may be further purified by chromatography followed by lyophilization or crystallization.

TAXANE DERIVATIVES STARTING MATERIALS

The processes described above may be applied to any taxane derivatives of the formula T-[OH]$_n$ to form compounds of formula (A). Many examples of T-[OH]$_n$ have been reported in the literature and some of which are listed below. (a) paclitaxel; (b) Taxotere®; (c) 10-desacetylpaclitaxel; (d) taxane derivatives disclosed in PCT application 93/06079 (published Apr. 1, 1993) having the formula

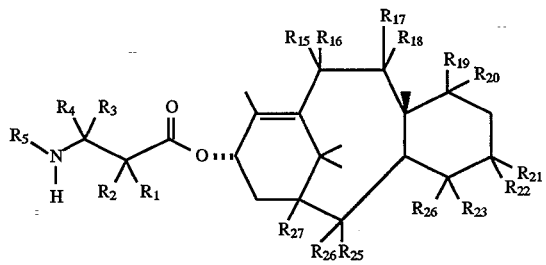

wherein $R_1$ is —$OR_6$, —$SR_7$, or —$NR_8R_9$; $R_2$ is hydrogen, alkyl, alkenyl, alkynyl, aryl, or heteroaryl; $R_3$ and $R_4$ are independently hydrogen, alkyl, alkenyl, alkynyl, aryl, heteroaryl, or acyl, provided, however, that $R_3$ and $R_4$ are not both acyl; $R_5$ is —$COR_{10}$, —$COOR_{10}$, —$COSR_{10}$, —$CONR_8R_{10}$, —$SO_2R_{11}$, or —$POR_{12}R_{13}$; $R_6$ is hydrogen, alkyl, alkenyl, alkynyl, aryl, heteroaryl, hydroxy protecting group, or a functional group which increases the water solubility of the taxane derivative; $R_7$ is alkyl, alkenyl, alkynyl, aryl, heteroaryl, or sulfhydryl protecting group; $R_8$ is hydrogen, alkyl, alkenyl, alkynyl, aryl, heteroaryl; $R_9$ is an amino protecting group; $R_{10}$ is alkyl, alkenyl, alkynyl, aryl, heteroaryl; $R_{11}$ is alkyl, alkenyl, alkynyl, aryl, heteroaryl, —$OR_{10}$, or —$NR_8R_{14}$; $R_{12}$ and $R_{13}$ are independently alkyl, alkenyl, alkynyl, aryl, heteroaryl, —$OR_{10}$, or —$NR_8R_{14}$; $R_{14}$ is hydrogen, alkyl, alkenyl, alkynyl, aryl, heteroaryl; $R_{15}$ and $R_{16}$ are independently hydrogen, hydroxy, lower alkanoyloxy, alkenoyloxy, alkynoyloxy, aryloyloxy or $R_{15}$ and $R_{16}$ together form an oxo; $R_{17}$ and $R_{18}$ are independently hydrogen, hydroxy, lower alkanoyloxy, alkenoyloxy, alkynoyloxy, aryloyloxy or $R_{17}$ and $R_{18}$ together form an oxo; $R_{19}$ and $R_{20}$ are independently hydrogen or hydroxy or lower alkanoyloxy, alkenoyloxy, alkynoyloxy, or aryloyloxy; $R_{21}$ and $R_{22}$ are independently hydrogen or lower alkanoyloxy, alkenoyloxy, alkynoyloxy, or aryloyloxy or $R_{21}$ and $R_{22}$ together form an oxo; $R_{24}$ is hydrogen or hydroxy or lower alkanoyloxy, alkenoyloxy, alkynoyloxy, or aryloyloxy; or $R_{23}$ and $R_{24}$ together form an oxo or methylene or $R_{23}$ and $R_{24}$ together with the carbon atom to which they are attached form an oxirane ring or $R_{23}$ and $R_{22}$ together with the carbon atom to which they are attached form an oxetane ring; $R_{25}$ is hydrogen, hydroxy, or lower alkanoyloxy, alkenoyloxy, alkynoyloxy, or aryloyloxy; or $R_{26}$ is hydrogen, hydroxy, or lower alkanoyloxy, alkenoyloxy, alkynoyloxy, or aryloyloxy; or $R_{26}$ and $R_{25}$ taken together form an oxo; and $R_{27}$ is hydrogen, hydroxy or lower alkoxy, alkanoyloxy, alkenoyloxy, alkynoyloxy, or aryloyloxy; (e) taxane derivatives disclosed in U.S. Pat. No. 5,227,400 3'-desphenyl-3'-(2-furyl) or 3'-(2-thienyl) derivatives of paclitaxel, Taxotere®; (f) taxane derivatives disclosed in EP 534,709 published Mar. 31, 1993 (paclitaxel derivatives in which the sidechain phenyl groups are independently replaced with naphthyl, styryl or substituted phenyl). See also PCT 92/09589 published Jun. 11, 1992; (g) taxane derivatives disclosed in EP 534,707 published Mar. 31, 1993 (paclitaxel derivatives in which the 3'-N-benzoyl group is replaced with ethoxycarbonyl or methoxycarbonyl); (h) PCT Application 93/06093 published Apr. 1, 1993 (10-desacetoxy derivatives of paclitaxel and Taxotere®); (i) EP 524,093 published Jan. 20, 1993 (10-, 7-, or 7,10-bis-O-(N-substituted carbamoyl taxane derivatives); (j) 9-α-hydroxy analog of paclitaxel is disclosed in Klein, "Synthesis of 9-Dihydrotaxol: A New Bioactive Taxane," Tetrahedron Letters, 1993, 34(13):2047–2050; (k) 14-β-hydroxy analog of paclitaxel and Taxotere® prepared from 14β-hydroxy-10-deacetylbaccatin III are disclosed at the 205th ACS National Meeting in Colorado, 1993. (Med. Chem. Division, Abstract No. 28); and (1) other taxanes, such as C7-fluorotaxanes and various C10-substituted taxanes, as disclosed in European Patent Application 577, 082A1 published Jan. 5, 1994, which is herein incorporated by reference in its entirety.

The free hydroxy group or groups of taxane derivatives may be converted by conventional methods to the corresponding ester or carbonate; for example in compounds of formula (Ia) one of $R^{1a}$, $R^{2a}$ or $R^{3a}$ is —OC(O)R* or —OC(O)OR*and R* is as previously defined. Thus, a taxane derivative T-OH may be reacted with a compound of the formula L-C(O)OR* (L being a leaving group) such as a chloroformate in the presence of a base such as tertiary amine to give the corresponding carbonate; for example, paclitaxel reacts with ethyl chloroformate in the presence of diisopropylethylamine to provide 2'-O-ethyloxycarbonylpaclitaxel. T-OH may also react with a carboxylic acid R*CO$_2$H or an acylating equivalent thereof (e.g. an anhydride, active ester or an acyl halide) to provide the corresponding ester. Needless to point out when R* in L-C(O)OR*, or R*CO$_2$H or an acylating equivalent thereof contains hydroxy groups, they are preferably protected with suitable hydroxyprotecting groups.

Additionally, taxane derivatives T-[OH]$_n$ may be prepared by acylating a taxane moiety having a C13-hydroxy group with an appropriately substituted 3-amino-2-hydroxypropanoic acid, an acylating equivalent thereof, or a precursor thereof. Suitable precursors of substitutd 3-amino-2-hydroxypropanoic acid are for example azetidinones of formula (III). This acylation reaction is exemplified in the coupling of hydroxy protected baccatin III or hydroxyprotected 10-deacetylbaccatin III and a phenylisoserine derivative to give paclitaxel derivatives as disclosed in e.g. Denis et al. U.S. Pat. Nos. 4,924,011 and 4,924,012; and in the coupling of a protected baccatin III and an azetidinone to give paclitaxel and derivatives thereof as disclosed in EP Published Application 400,971 published Dec. 5, 1990 (now U.S. Pat. No. 5,175,315) and U.S. Pat. No. 5,229,526.

The process as disclosed in EP 400,971 (the Holton process) involves reacting 1-benzoyl-3-(1-ethoxy)ethoxy-4-phenyl-2-azetidinone with 7-O-triethylsilylbaccatin III in the presence of N,N-dimethylaminopyridine and pyridine at 25° C. for 12 hours; paclitaxel is obtained after the various hydroxyprotecting groups are removed. An improvement of the Holton process is reported by Ojima et al in "New and Efficient Approaches to the Semisynthesis of Taxol and its C-13 Side Chain Analogs by Means of β-Lactam Synthon Method" Tetrahedron, 1992, 48(34):6985–7012. Ojima's process involves first generating the sodium salt of 7-triethylsilylbaccatin III with sodium hydride; this salt is then reacted with chiral 1-benzoyl-3-(1-ethyoxy)ethoxy-4-phenyl-2-azetidinone to provide paclitaxel after removal of the hydroxy protecting groups. In U.S. Pat. No. 5,229,526 Holton discloses the coupling of a metal alkoxide of baccatin III or a derivative thereof with a 2-azetidinone to provide taxanes with C13 sidechain. This process is said to be highly diastereoselective; therefore racemic mixtures of the sidechain precursor 2-azetidinone may be used. Recently, Ojima et al reported in "A Highly Efficient Route to Taxotere by the β-Lactam Synthon Method," Tetrahedron Letters, 1993, 34(26):4149–4152, the coupling of metal alkoxides of 7,10-bis-O-(trichloroethoxycarbonyl)-10-deacetylbaccatin III with chiral 1-(t-butoxycarbonyl)-4-phenyl-3-(protected hydroxy)-2-azetidinone to give Taxotere® after deprotection. The relevant portions of all references cited above are hereby incorporated by reference.

The baccatin/azetidinone process generalized to the preparation of compounds of formula (Ia) is illustrated in Scheme VI. Again, other taxane derivatives not specifically encompassed within the formula (Ia) may also be prepared by this process by employing appropriate starting materials.

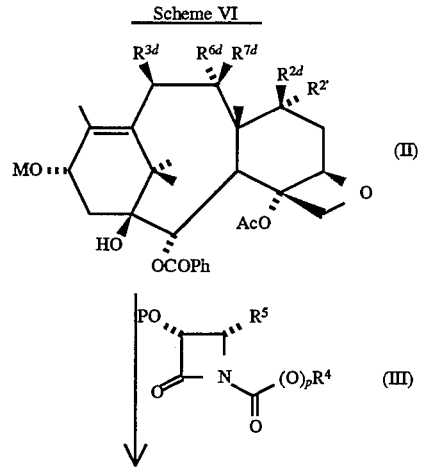

-continued
Scheme VI

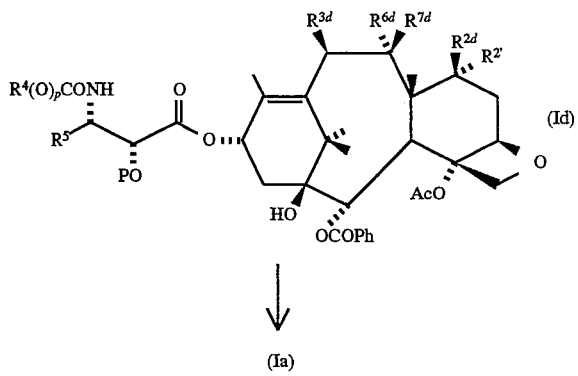

In Scheme VI, $R^{2'}$ is hydrogen, and $R^{2d}$ is hydrogen, protected hydroxy, —OC(O)$R^x$ or —OC(O)O$R^x$; $R^{3d}$ is hydrogen, —OC(O)$R^x$, $C_{1-6}$alkyloxy, protected hydroxy or —OC(O)O$R^x$; one of $R^{6d}$ or $R^{7d}$ is hydrogen and the other is hydroxy, protected hydroxy or $C_{1-6}$ alkanoyloxy; or $R^{6d}$ and $R^{7d}$ together form an oxo group; P is a hydroxy protecting group; M is hydrogen or a Group IA metal such as lithium, sodium or potassium; and p, $R^4$, $R^5$ and $R^x$ are as previously defined. The reaction may be conducted according to the procedure disclosed in EP 400,971 wherein the baccatin III derivative of formula (II) wherein M is hydrogen is reacted with an azetidinone of formula (III) in the presence of an organic base such as N,N-dimethylaminopyridine. Preferably, however, the baccatin III derivative is first converted to a 13-alkoxide by treating the former with a strong base such as hydrides, alkylamides, and bis(trialkylsilyl)amides of Group IA metals as disclosed in U.S. Pat. No. 5,229,526 and the Ojima references, supra. More preferably, the 13-alkoxide is a lithium alkoxide. The formation of a lithium salt may be achieved by reacting a compound of formula (II) wherein M is hydrogen with a strong metal base, such as lithium diisopropylamide, $C_{1-6}$ alkyllithium, lithium bis(trimethylsilyl)amide, phenyllithium, lithium hydride, or the like base. Needless to point out that if a compound of formula (II) contains hydroxy groups in radical $R^x$, said hydroxy groups are preferably protected with suitable hydroxy protecting groups.

The coupling reaction between a taxane of formula (II) and an azetidinone of formula (III) is conducted in an inert organic solvent such as tetrahydrofuran at reduced temperature in the range of about 0° C. to about −78° C. The azetidinones of formula (III) may be used as a racemic mixture to couple with taxane metal alkoxides of formula (II) in which M is a group 1A metal; in such case, the azetidinone reactant is preferably used in at least 2 equivalents relative to the taxane reactant, and more preferably from about 3 to about 6 equivalents. Chiral azetidinones may also be used, and in such case one equivalent of the azetidinone relative to the taxane may be sufficient, but preferably the azetidinone is used in slight excess, for example up to 1.5 equivalents.

The hydroxy protecting groups may be the same or they may be chosen in a manner to allow the selective removal of one or more protecting groups without substantially affecting the others; for example, in a compound of formula (Id), $R^{2d}$ and PO may be both triethylsilyloxy, and $R^{3d}$ may be benzyloxycarbonyl; catalytic hydrogenolysis in the presence of palladium on carbon removes the benzyloxycarbonyl protecting group without removing the triethylsilyl group. Thus, the hydroxy protecting groups of a compound of formula (Id) may be selectively removed to provide a compound of formula (Ia).

Compounds of formula (II) are either known in the literature, e.g baccatin III, 10-deacetylbaccatin III and their hydroxy protected derivatives, or can be prepared from the known compounds by conventional conventional methods, e.g converting a hydroxy group to a carbonate. Additional compounds of formula (II) may be prepared according to procedures described hereinbelow in the section PREPARATION OF STARTING MATERIALS.

Compounds of formula (III) can be prepared from a compound of (IIIa) according to the general method described in EP 400,971 and Ojima et al, Tetrahedron, 48:6985–7012, 1992.

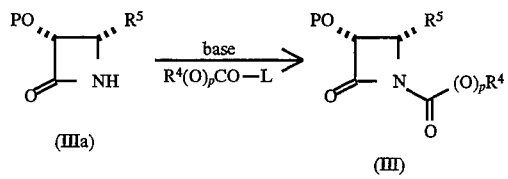

Thus a compound of formula (IIIa) is first treated with a base such as n-butyllithium or triethylamine, and then followed by a compound of the formula $R^4(O)_pCO$-L where L is a leaving group to provide a compound of formula (III).

Compounds of (IIIa) may be prepared according to the general method disclosed in EP 400,971 by going through an intermediate compound 3-acetoxy-4-substituted-2-azetidinone (IIIb); or by the method disclosed in U.S. Pat. No. 5,229,526 by going through an intermediate compound 3-triethylsilyloxy-4-substituted-2-azetidinone. In an improved process a compound (IIIb) may be obtained by condensing acetoxyacetyl chloride with a bis-imine followed by hydrogenolysis or acid cleavage to remove the N-imine group; this process is shown in the following scheme in which $R^{5'}$ is an optionally substituted aryl or a heteroaryl group such as furyl or thienyl. This process is disclosed in co-pending application U.S. Ser. No. 08/165, 610 filed Dec. 13, 1993 which is hereby incorporated by reference.

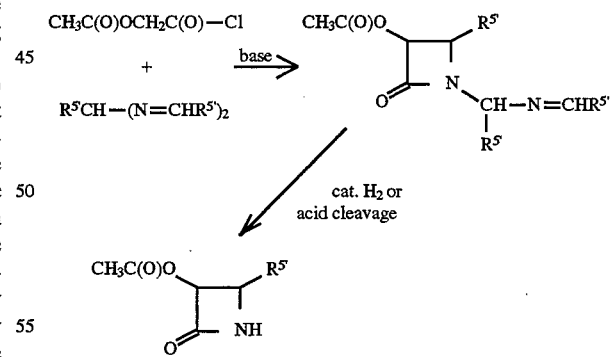

The products (IIIb) obtained from these cycloaddition reactions are usually a racemic mixture of the two cis-azetidinones. The racemic mixture may be resolved by conventional methods such as conversion to diastereomers, differential absorption on column packed with chiral adsorbents, or enzymatically. For example, a racemic mixture of compounds of formula (IIIb) may be contacted with an enzyme that catalyzes the hydrolysis of an ester, for example an esterase or a lipase, to selectively cleave the 3-acyl group of one enantiomer without affecting the other.

(See e.g. Brieva et al, *J. Org. Chem.*, 1993, 58:1068–1075; also co-pending application U.S. Ser. No. 092,170 filed Jul. 14, 1993, European Patent Application Number 552041, published Jul. 21, 1993). Alternatively, the racemic mixture may be first subjected to base-catalyzed hydrolysis to remove the 3-acyl group and to generate a racemic mixture of the corresponding 3-hydroxy β-lactam; the racemic mixture of 3-hydroxy β-lactam is then contacted with an enzyme capable of catalyzing acylation of an hydroxy group to selectively acylate the hydroxy group of one enantiomer without affecting the other. Or the racemic mixture of 3-hydroxy β-lactam may be acylated with a chiral carboxylic acid, and the resulting diastereomeric mixture may then be separated using methods known in the art, and the chiral auxiliary removed to provide the desired enantiomer.

Ojima et al, in *J. Org. Chem.*, 56:1681–1683, 1991; *Tet. Lett.*, 33:5737–5740, 1992; and *Tetrahedron*, 48:6985–7012, 1992 reported the synthesis of a number of chiral azetidinones of formula (IIIa) and/or the corresponding N-(p-methoxyphenyl) congener; wherein P is the hydroxy protecting group triisopropylsilyl; and $R^5$ is 4-methoxyphenyl, 3,4-dimethyoxyphenyl, phenyl, 4-fluorophenyl, 4-trifluoromethylphenyl, 2-furyl, 2-phenylethenyl, 2-(2-furyl)ethenyl, 2-methylpropyl, cyclohexylmethyl, isopropyl, phenethyl, 2-cyclohexylethyl, or n-propyl. Other references for making azetidinones fo formula (IIIa) and/or (III) can be found in European Patent Applications 0,534,709 A1, 0,534, 708 A1, and 0,534,707 A1, all three published on Mar. 31, 1993; in PCT application WO 93/06079 published on Apr. 1, 1993; in *Bioorganic and Medicinal Chemistry Letters*, 3, No. 11, DP 2475–2478 (1993); also in *Bioorganic and Medicinal Chemistry Letters*, 3, No. 11, pp 2479–2482 (1993); in *J. Org. Chem.*, 58, pp 1068–1075; in *Tetrahedron Letters*, 31, No. 44, pp 6429–6432 (1990); in *Bioorganic and Medicinal Chemistry Letters*, 3, No. 11, pp 2467–2470 (1993); European Application 552,041 published on Jul. 21, 1993; and in our copending U.S. application Ser. No. 092,170 filed on Jul. 14, 1993. The relevant portions of all aforementioned references are hereby incorporated by reference. Other azetidinones within the definition of formula (III) but are not specifically disclosed in these references may be prepared by a person skilled in the art following the methodologies generally known in the art.

BIOLOGICAL EVALUATION

Compounds of formula (B) of the present invention are useful intermediates for novel antitumor agents of formula (A). In addition, some compounds within the scope of formula (B), namely compounds of formula (B'), were themselves found to be antitumor agents. Biological Section I below demonstrates the antitumor activity of the compounds of formula (A). On the other hand, Biological Section II below demonstrates the antitumor activity of the compounds of formula (B').

Biological Section I

In Vitro Cytotoxicity Data

The compounds of formula (A) showed in vitro cytoxicity activity against human colon carcinoma cells HCT-116 and HCT-116/VM46. The HCT-116/VM46 cells are cells that have been previously selected for teniposide resistance and express the multi-drug resistance phenotype, including resistance to paclitaxel. Cytotoxicity was assessed in HCT-116 human colon carcinoma cells by XTT (2,3-bis(2-methoxy-4-nitro-5-sulfphenyl)-5-[(phenylamino)carbonyl]2H-tetrazolium hydroxide) assay as reported in D. A. Scudiero, et al., "Evaluation of soluble tetrazolium/formazan assay for cell growth and drug sensitivity in culture using human and other tumor cell lines," *Cancer Res.* 48:4827–4833, 1988. Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance, the greater the number of live cells. The results are expressed as an $IC_{50}$, which is the drug concentration required to inhibit cell proliferation (i.e., absorbance at 450 nm) to 50% of that of untreated control cells. The $IC_{50}$ values for representative compounds evaluated in this assay are given in Table I.

TABLE I

| In vitro cytotoxicity data against human colon carcinoma cells. | | |
|---|---|---|
| | $IC_{50}$ (μM) | |
| Compound[1] | HCT-116 | HCT-116/VM46 |
| Taxotere ® | 0.004 | 0.213 |
| paclitaxel | 0.004 | 0.44 |
| Example 1 | 0.0158 | 1.24 |
| Example 3 | 0.312 | 6.25 |
| Example 4 | 0.0457 | >6.3 |

[1]Examples 1 and 4 as free acid; example 3 as sodium salt.

The compound 7-O-methylthiomethylpaclitaxel (Example 1 (a) was also tested in the cytotoxicity assay and it showed $IC_{50}$ of 0.003 μM against HCT-116 and 0.025 μM against HCT-116/VM46.)

In Vivo Antitumor Activity

Balb/c×DBA$_2$ F$_1$ (CDF$_1$) hybrid mice were implanted subcutaneously (sc) with 0.1 ml of a 2% (w/v) brei of M109 lung carcinoma (as described in W. Rose "Evaluation of Madison 109 Lung Carcinoma as a Model for Screening Antitumor Drugs," *Cancer Treatment Reports*, 65, No. 3–4 pp. 299–312 (1981). The test compounds and reference drug, paclitaxel, were administered intravenously to groups of mice; each group received a compound at a different dose level, and three or four different dose levels were evaluated per compound. Mice were followed daily for survival until their death or about day 75 post-tumor implant, whichever occurred first. One group of mice per experiment remained untreated and served as the control. Tumors were also measured once or twice weekly and the size in mm was used to estimate tumor weight according to the published procedure (ibid).

Median survival times of compound-treated (T) mice were compared to the median survival time of parallel control (C) mice. The ratio of the two values for each compound-treated group of mice was multiplied by 100 and expressed as a percentage (i.e., % T/C) in Table II for representative compounds. Additionally, the difference between the median time for treated groups and that for the control group to grow tumor to 1 gm, expressed as T–C values in days, is also shown in Table II. The greater the T–C value, the greater the delay in primary tumor growth. Compounds showing % T/C≧125% and/or T–C≧4.0 days are considered to be active in the M109 SC model.

TABLE II

| Compound | Maximum Effect % T/C | T-C (days) | Opt. Dose (mg/kg/inj;) |
|---|---|---|---|
| Example 1[d] | 131 | 14.0 | 45[a] |
| paclitaxel | 134 | 14 | 48/24[a,c] |
| Example 3[d] | 160 | 18.8 | 24[b] |
| paclitaxel | 151 | 15 | 18[b] |

[a]Compound was administered i.v. once daily, on days 4, 5, 6, 7 and 8 post-tumor implant.
[b]Compound was administered i.v. once daily, on days 5, 6, 7, 8 and 9 post-tumor implant.
[c]Higher dose achieved maximum increase in lifespan; lower dose associated with causing maximum delay in tumor growth.
[d]sodium salt.

Compound of Example 3 (as the triethanolamine salt) was further evaluated in murine and human xenograft tumor models (M109, A2780/cDDP—human ovarian carcinoma resistant to cisplatin, and HCT-116—human colon carcinoma) against paclitaxel as positive control. The A2780/cDDP model is described in Rose and Baslet, *In Vivo*, 1990, 4:391–396; the HCT-116 model is described in Rose and Baslet, *In Vivo*, 1989, 3:249–254. M109 was passaged sc biweekly in Balb/C mice and implanted sc into CDF1 mice for antitumor evaluation. A2780/cDDP and HCT-116 were grown in athymic mice for both passage (every two to three weeks) and therapy experiments. Compound of Example 3 was administered iv in water, or orally in water with a few drops of Tween 80, while paclitaxel was either suspended in water plus Tween 80, or dissolved in cremophore/ethanol (50%/50%) and diluted with saline. The treatment regimen for the sc M109 tumor tests was once daily for 5 consecutive days beginning on Day 4 post tumor implant. For the human tumor xenograft tests, compounds were given once daily every other day for five administrations beginning when the tumors were staged to between 50 to 100 mg.

In one M109 experiment, compound of Example 3 administered iv achieved max. % T/C of 155 (T–C of 19 days) at 36 mg/kg/inj. (cf. paclitaxel max. % T/C of 132 (T–C of 13 days) at 36 or 18 mg/kg/inj.). In the same experiment, compound of Example 3 administered orally achieved a max. % T/C of 158 (T–C of 22.8 days) at a dose of 160 mg/kg/adm. while paclitaxel at the same dose (highest tested) suspended in water and Tween 80 did not show activity. In another M109 experiment, iv administered compound of Example 3 produced max. % T/C of 170 (T–C of 17 days) at 48 mg/kg/inj. (cf. paclitaxel max. % T/C of 167 (T–C of 14 days) at 48 or 36 mg/kg/inj.). In the same experiment, orally administered compound of Example 3 produced max. % T/C of 172 (T–C of 17 days) at a dose of 200 mg/kg/adm. while paclitaxel dissolved in cremophore/ethanol/saline did not show activity at 60/mg/kg/inj. In this experiment, paclitaxel dissolved in cremophore/ethanol/saline could not be administered at greater than 60/mg/kg/inj. due to solubility and toxicity constraints.

In the A2780/cDDP experiment, iv administered compounds of Example 3 showed max. T–C value of 29.8 days at 36 mg/kg/inj (cf. paclitaxel max. T–C of 26.3 days at 36 mg/kg/inj.). Orally administered compound of Example 3 produced max. T–C of 20 days at a dose of 160 mg/kg/adm. In the HCT-116 experiment, iv treatment with 24 or 36 mg/kg/inj. of paclitaxel produced 6 cures of 7 or 6 cures of 8 treated mice, respectively, and 160 or 240 mg/kg/adm. of oral compound of Example 3 cured 6 or 7 of 8 treated mice, respectively. Cure means tumor-free on Day 80 post tumor implant.

The triethanolamine salt of compound of example 1 was also found to have oral activity in the M109 and HCT-116 models.

It is well appreciated in the art that there will be some, usually slight, variations in the anti-tumor activity depending on what particular salt form is employed.

The pharmaceutically acceptable salt of phosphonooxymethyl ethers of taxane derivatives of formula (A) exhibit improved water solubility over paclitaxel thereby allowing more convenient pharmaceutical formulations. Without being bound by theory, it is believed that the phosphonooxymethyl ethers of the present invention are prodrugs of paclitaxel or derivative thereof; the phosphonooxymethyl moiety being cleaved upon contact with phosphatase in vivo to generate subsequently the parent compound.

Biological Section II

Mice M109 Model

Balb/c×DBA/2 $F_1$ hybrid mice were implanted intraperitoneally, as described by William Rose in *Evaluation of Madison 109 Lung Carcinoma as a Model for Screening Antitumor Drugs, Cancer Treatment Reports*, 65, No. 3–4 (1981), with 0.5 mL of a 2% (w/v) brei of M109 lung carcinoma.

Mice were treated with compound under study by receiving intraperitoneal injections of various doses on either days 1, 5 and 9 post-tumor implant or days 5 and 8 post-implant. Mice were followed daily for survival until approximately 75–90 days post-tumor implant. One group of mice per experiment remained untreated and served as the control group. Median survival times of compound-treated (T) mice were compared to the median survial time of the control (C) mice. The ratio of the two values for each compound-treated group of mice was multiplied by 100 and expressed as a percentage (i.e. % T/C) in Table III for representative compounds of formula (B').

TABLE III

| EXAMPLE NUMBER | T/C (mg/kg/inj.; schedule in days) |
|---|---|
| 14 (b) | 143 (12; d. 5 + 9) |
| 15 | 192 (8; d. 5 + 9) |

As shown above, compounds of formula (A) and (B') of the instant invention are effective tumor inhibiting agents, and thus are useful in human and/or veterinary medicine. Thus, another aspect of the instant invention concerns a method for inhibiting human and/or other mammalian tumors which comprises administering to a tumor bearing host an antitumor effective amount of a compound of formula (A) or (B').

Compounds of formulas (A) and (B') of the present invention may be used in a manner similar to that of paclitaxel; therefore, an oncologist skilled in the art of cancer treatment will be able to ascertain, without undue experimentation, an appropriate treatment protocol for administering a compound of the present invention. The dosage, mode and schedule of administration for compounds of this invention are not particularly restricted, and will vary with the particular compound employed. Thus a compound of the present invention may be administered via any suitable route of administration, preferably parenterally; the dosage may be, for example, in the range of about 1 to about 100 mg/kg of body weight, or about 20 to about 500 mg/m$^2$.

Compounds of formula (A) and (B') may also be administered orally; oral dosage may be in the range of about 5 to about 500 mg/kg of body weight. The actual dose used will vary according to the particular composition formulated, the route of administration, and the particular site, host and type of tumor being treated. Many factors that modify the action of the drug will be taken into account in determining the dosage including age, weight, sex, diet and the physical condition of the patient.

The present invention also provides pharmaceutical compositions (formulations) containing an antitumor effective amount of a compound of formula (A) or (B') in combination with one or more pharmaceutically acceptable carriers, excipients, diluents or adjuvants. Examples of formulating paclitaxel or derivatives thereof may be found in, for example, U.S. Pat. Nos. 4,960,790 and 4,814,470, and such examples may be followed to formulate the compounds of this invention. For example, compounds of the present invention may be formulated in the form of tablets, pills, powder mixtures, capsules, injectables, solutions, suppositories, emulsions, dispersions, food premix, and in other suitable forms. They may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration.

Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

In the following experimental procedures, all temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quartet (dq). The solvents employed for taking NMR spectra are acetone-d$_6$ (deuterated acetone). DMSO-d$_6$ (perdeuterodimethylsulfoxide), D$_2$O (deuterated water), CDCl$_3$ (deuterochloroform) and other conventional deuterated solvents. The infrared (IR) spectral description include only absorption wave numbers (cm$^{-1}$) having functional group identification value.

Celite is a registered trademark of the Johns-Manville Products Corporation for diatomaceous earth.

The abbreviations used herein are conventional abbreviations widely employed in the art. Some of which are: MS (mass spectrometry); HRMS (high resolution mass spectrometry); Ac (acetyl); Ph (phenyl); v/v (volume/volume); FAB (fast atom bombardment); NOBA (m-nitrobenzyl alcohol); min (minute(s)); h or hr(s) (hour (s)); NIS (N-iodosuccinimide); BOC (t-butoxycarbonyl); CBZ or Cbz (benzyloxycarbonyl); Bn (benzyl); Bz (benzoyl); TES (triethylsilyl); DMSO (dimethylsulfoxide); THF (tetrahydrofuran); HMDS (hexamethyldisilazane).

PREPARATION OF STARTING MATERIALS

The preparations of several specific starting materials useful in the preparation of compounds of formula (A) are exemplified below.

Preparation 1. 10-Desacetoxypaclitaxel

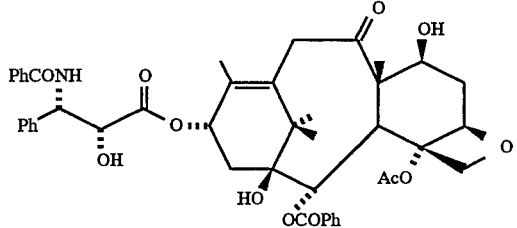

(a) 2',7-O-bis(2,2,2-trichloroethoxycarbonyl)-10-deacetyl paclitaxel

10-Deacetyl paclitaxel (140 mg, 0.173 mmol) in dry dichloromethane (3.5 mL) was treated at 0° C. with pyridine (0.028 mL, 0.346 mmol) and trichloroethyl chloroformate (0.0724 mL, 0.260 mmol). After 1 h at this temperature, the cold bath was removed and the mixture was stirred at room temperature overnight. The solvent was evaporated and the residue chromatographed on silica gel (30–50% ethyl acetate in hexane) to afford the title compound as a foam (92.3 mg, 46%). Further elution afforded unreacted starting material (35 mg, 25%), and 2',10-O-bis(2,2,2-trichloroethoxycarbonyl)-10-deacetylpaclitaxel in 16% yield.

(b) 2',7-O-bis(2,2,2-trichloroethoxycarbonyl)-10-desacetoxy-11,12-dihydropaclitaxel-10,12(18)-diene The product obtained in step (a) (92.3 mg, 0.079 mmol) in dry dichloromethane (2 mL) was treated at room temperature with 1,1,2-trifluoro-2-chlorotriethylamine (0.0384 mL, 0.238 mmol). The solution was stirred overnight. The solvent was evaporated and the residue purified by column chromatography (25% ethyl acetate in hexane) to afford the title compound as a white powder (42.8 mg, 47.3%).

(c) 10-Desacetoxy-11,12-dihydropaclitaxel-10,12 (18)-diene

The product of step (b) (39 mg, 0.034 mmol) was dissolved in methanol (0.5 mL) and acetic acid (0.5 mL), and treated with acid-washed zinc dust (66.4 mg, 1.020 mmol). The slurry was heated at 40° C. for 1 h, filtered and the filtrate evaporated. Chromatography of the residue with 60% ethyl acetate/hexane gave the title compound as a foam (22 mg, 81%).

(c) 10-Desacetoxypaclitaxel

The product of step (c) (22 mg, 0.028 mmol) in ethyl acetate (0.7 mL) was hydrogenated at atmospheric pressure in the presence of palladium on charcoal (10%, 14.7 mg, 0.014 mmol Pd) After 5.5 h at RT, filtration (rinsing with ethyl acetate), evaporation and chromatography (60% ethyl acetate in hexane) gave the title product (15.0 mg, 68%) as a white foam.

Preparation 2. 7-Deoxy-7α-fluoropaclitaxel

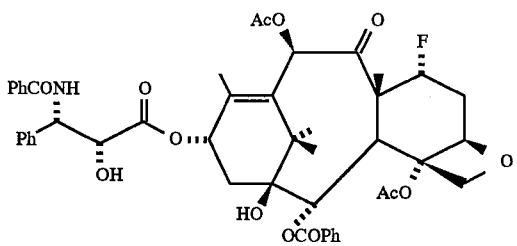

(a) 2'-O-Benzyloxycarbonyl-7-deoxy-7α-fluoropaclitaxel

Diethylaminosulfur trifluoride (DAST, 18.7 μL, 0.141 mmol) was dissolved in dry dichloromethane (0.5 mL), and this solution was cooled to 0° C. A solution of 2'-O-(benzyloxycarbonyl)paclitaxel (71 mg, 0.072 mmol) in dichloromethane (1 mL) was added and the resulting solution was kept at 0° C. for 30 min and at room temperature for 4 h. Then, water (0.15 mL) was added to the reaction mixture in order to quench the reaction and the resultant mixture was concentrated to leave a residue. The residue was chromatographed on a silica gel column (being eluted with 40% ethyl acetate in hexane) to yield 61 mg (Y: 85.7%) of a 1:1 mixture of the title compound and 2'-O-benzyloxycarbonyl-8-desmethyl-7,8-cyclopropapaclitaxel.

(b) 7-Deoxy-7α-fluoropaclitaxel

The product mixture obtained in Step (a) (89 mg) was dissolved in ethyl acetate (3 mL) and the mixture was stirred under slightly over one atmospheric pressure of hydrogen in the presence of palladium on charcoal (10% Pd, 29 mg, 0.027 mmol). After 12 h, the solvent was removed, and the residue was purified by silica gel chromatography (being eluted with 40% ethyl acetate in hexane) to afford 67.7 mg of the title compound, along with 8-desmethyl-7,8-cyclopropapaclitaxel.

The following HPLC method was used to separate the 7-deoxy-7α-fluoropaclitaxel and 8-desmethyl-7,8-cyclopropapaclitaxel.
Equipment
Pump: PE Series 4
Column: Shandon Hypercarb (graphitized carbon), 7μ, 100× 4.6 mm, #59864750 (information on preparative size columns may be obtained from Keystone Scientific, Bellefonte, Pa.)
Injector: PE ISS-100
Detector: HP-1040M
Conditions
Mobile Phase: 85:15 methylene chloride: hexane Separation not lost at 80:19:1 methylene chloride:hexane:isopropyl alcohol
Flow Rate: 2.5 mL/min
Detector: 254 nm
Diluent: Sample dissolved in methylene chloride Preparation 3. 7-Deoxy-7α-fluorobaccatin III

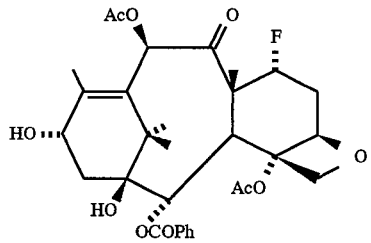

To a dry flask under an inert atmosphere was added 2'-O-(benzyloxycarbonyl)paclitaxel (4 g, 4 mmol) and dry toluene (80 mL). The resulting slurry was stirred at ambient temperature while dry tetrahydrofuran (16 mL) was added dropwise until a colorless solution resulted. The above solution was cooled to −78° C. in a dry ice/acetone bath then treated with diethylaminosulfur trifluoride (DAST, 1.2 mL, 2.5 eq.). The reaction mixture was allowed to stir for 16 h as it gradually warmed to ambient temperature. The resulting suspension was filtered and the filtrate (diluted with ethyl acetate (30 mL)) was washed with saturated aqueous sodium bicarbonate followed by brine. The organic fraction was dried ($MgSO_4$) and concentrated to give a crude product as a white foam. The crude material was partially purified by silica gel column chromatography (eluted with 10% $CH_3CN$ in $CH_2Cl_2$) to afford 1.45 g of a mixture of 2'-O-(benzyloxycarbonyl)-7-deoxy-7α-fluoropaclitaxel and 2'-O-(benzyloxycarbonyl)-8-desmethyl-7,8-cyclopropapaclitaxel (82:18 mixture by $^1$H-NMR).

The above mixture (1.45 g) was taken up in ethyl acetate (60 mL) and treated with palladium on carbon (300 mg). After shaking for 4 h under 50 pounds per square inch (psi) of hydrogen, the reaction was vented and filtered through a short plug of silica gel and concentrated. This furnished the desired product mixture, 7-deoxy-7α-fluoropaclitaxel and 8-desmethyl-7,8-cyclopropapaclitaxel, as a white foam (1.24 g, Y: 99%, 90:10 mixture by $^1$H-NMR). This mixture was taken up in dry methylene chloride (30 mL) and treated with tetrabutylammoniumborohydride (745 mg, 2.9 mmol, 2 eq) and allowed to stir for 6 h. The reaction was then quenched with acetic acid (1 mL), diluted with additional methylene chloride (30 mL) and washed with saturated aqueous sodium bicarbonate solution. The organic fraction was dried ($MgSO_4$) and concentrated. The crude, substituted taxane core mixture was partially purified by silica gel column chromatography (eluted with 10% $CH_3CN$ in $CH_2Cl_2$) to give a 90:10 mixture (as determined by $^1$H-NMR) of 7-deoxy-7-α-fluorobaccatin III and 8-desmethyl-7,8-cyclopropabaccatin III (510 mg, 60%) as a white foam. The resulting foam was crystallized from hot isopropanol to give 7-deoxy-7α-fluorobaccatin III (as small white needles (Y: 410 mg); m.p. 234°–236° C. (decomposition).

Preparation 4. 10-Desacetoxy-7-deoxy-7α-fluoropaclitaxel

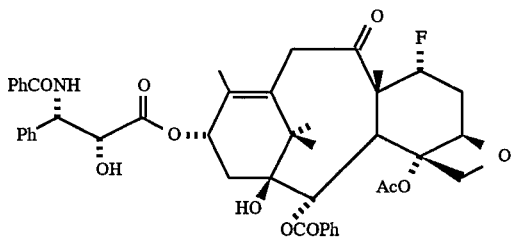

(a) 2'-O-Benzyloxycarbonyl-10-desacetoxypaclitaxel

10-Desacetoxypaclitaxel (27 mg, 0.034 mmol) in dichloromethane (1 mL) was treated with benzyl chloroformate (0.0146 mL, 0.102 mmol), followed by diisopropylethylamine (0.0177 mL, 0.102 mmol). The reaction mixture was stirred at 0° C. for 45 min, and at rt for 12 h. Evaporation of the solvent and silica gel chromatography (being eluted with 40% ethyl acetate in hexane) gave 25.5 mg (Y: 81%) of the title compound as a foam.

(b) 10-Desacetoxy-7-deoxy-7α-fluoropaclitaxel

The product obtained in Step (a) (25.5 mg, 0.028 mmol) in dichloromethane (0.8 mL) at 0° C. was treated with DAST (0.0071 mL, 0.055 mmol). After 45 min at 0° C., the reaction was allowed to proceed for 5 h at rt. Evaporation of the solvent and chromatography gave 2'-O-benzyloxycarbonyl-7-deoxy-7α-fluoropaclitaxel as a crude foam. This compound was dissolved in ethyl acetate (1 mL) and was stirred under slightly over one atmosphere of hydrogen in the presence of palladium on charcoal (10%, 8.9 mg) for 12 h at rt. The catalyst was removed by filtration and silica gel chromatography of the product gave 10 mg (Y: 40% over two steps) of the title product as a foam.

Preparation 5. 10-Deacetyl-7-deoxy-7α-fluoropaclitaxel

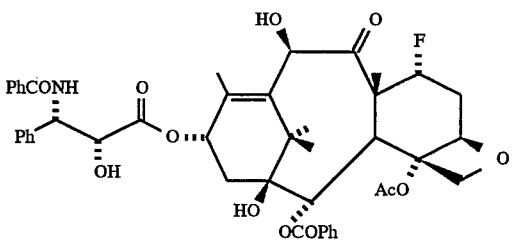

A solution of 2',10-O-bis(2,2,2-trichloroethoxycarbonyl)-10-deacetylpaclitaxel (120 mg, 0.103 mmol) in dichloromethane (2 mL) was cooled at 0° C. and treated with DAST (0.0266 mL, 0.207 mmol). The solution was stirred at 0° C. for 30 min and at rt for 4 h. The reaction was quenched by adding water (0.05 mL). The reaction mixture was concentrated and the residue was purified by silica gel chromatography (being eluted with 30% ethyl acetate in hexane) to afford 81 mg (Y: 68%) of 2',10-O-bis(2,2,2-trichloroethoxycarbonyl)-7-deoxy-7α-fluoropaclitaxel as a foam. This compound (63 mg, 0.054 mmol) was dissolved in methanol (0.5 mL) and acetic acid (0.5 mL) and treated with zinc dust (104 mg, 1.62 mmol) for 90 min at 45° C. The reaction mixture was filtered and the filtrate was concentrated. Silica gel chromatography (being eluted with 40% hexane in 60% ethyl acetate) of the residue afforded 38 mg (Y: 86%) of the title compound as a white solid.

Preparation 6. 7-Deoxybaccatin III

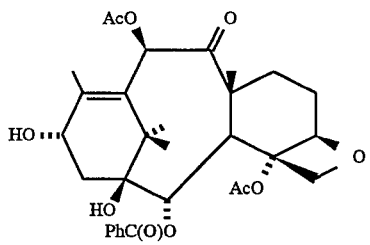

(a) 7-O-[(Methylthio)thiocarbonyl]baccatin III

Baccatin III (750 mg, 1.278 mmol) was dissolved in dry tetrahydrofuran (20 mL) and imidazole (8.7 mg, 0.128 mmol) was added in one lot. Sodium hydride (50% in mineral oil, 77 mg, 1.597 mmol) was added at room temperature. When gas evolution had ceased (10 min), carbon disulfide (4.6 mL) was added at once. After 3 h at room temperature, the yellow solution was treated with methyl iodide (0.238 mL, 3.835 mmol) and stirred overnight. Workup with ethyl acetate and water gave the title compound as a crude oil.

Alternate Run:

Baccatin III (394 mg, 0.672 mmol) was dissolved in tetrahydrofuran (5 mL) and carbon disulfide (1 mL). To this solution was added sodium hydride (40.3 mg, 60%, 1.009 mmol). A catalytic amount of imidazole was also added. The reaction mixture was stirred at room temperature for 1.5 h. and then methyl iodide (122.8 μL, 2.016 mmol) was added. After 40 min, the solvent was removed in vacuo, and the residue was chromatographed on silica gel (eluted with 20%–50%–60% ethyl acetate in hexanes) to afford the title product (260 mg, Y: 57.2%) together with 7-epi baccatin (98.5 mg, 25%).

(b) 7-O-[(Methylthio)thiocarbonyl]-13-O-triethylsilylbaccatin III

The product of step (a) as a crude oil was dissolved in dry dimethylformamide (5 mL) and treated with imidazole (870 mg, 12.78 mmol) and triethylsilyl chloride (2.10 mL, 12.78 mmol) at room temperature for 15 h. Addition of water was followed by extraction into ethyl acetate. The organic layer was washed extensively with water, and then dried. Silica gel flash chromatography (being eluted with 20% ethyl acetate in hexanes) gave the title compound as a glassy solid (Y: 209 mg, 20% yield over two steps).

Alternate Run:

The product of step (a) (193.4 mg, 0.286 mmol) was dissolved in dry dimethylformamide (2.86 mL). To this solution was added imidazole (77.9 mg, 1.14 mmol), followed by triethylsilyl chloride (192 μL, 1.14 mmol). The reaction mixture was stirred overnight at room temperature. After 12 h, the reaction mixture was diluted with ethyl acetate (150 mL). The organic layer was washed with water (3×10 mL) and brine (1×10 mL), dried, and concentrated in vacuo. The residue was chromatographed on silica gel (eluted with 20% Ethyl acetate in hexanes) to afford the title product (163 mg, Y: 72.0%).

(c) 7-Deoxy-13-O-triethylsilylbaccatin III

The product of step (b) (182 mg, 0.230 mmol) in dry benzene (5 mL) was heated to 80° C. in the presence of tributyltin hydride (0.310 mL, 1.150 mmol) and 2,2'-azobisisobutyronitrile (AIBN, 10 mg). After 3 h the solution was allowed to cool, and the solvent evaporated in vacuo. Silica gel chromatography of the residue (being eluted with 20% ethyl acetate in hexane) gave the title compound as an oil.

(d) 7-Deoxybaccatin III

The product of step (c) was dissolved in tetrahydrofuran (5 mL) and treated with tetrabutylammonium fluoride (1M in tetrahydrofuran, 0.50 mL, 0.50 mmol) for 2 h at room temperature. Dilution with ethyl acetate and washing with water and brine, followed by silica gel chromatography (being eluted with 1:1 ethyl acetate/hexane) gave the title compound as a white glassy solid (63 mg, Y: 58% over two steps).

Preparation 7. 10-Desacetoxybaccatin III

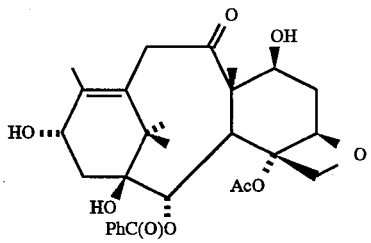

(a) 10-Deacetyl-10-O-(pentafluorophenoxy)thiocarbonyl-7-O-triethylsilylbaccatin III 7-O-Triethylsilyl-10-deacetylbaccatin III (see Greene et al, J. Am. Chem. Soc., 110, p. 5917, 1988) (319 mg, 0.485 mmol) was dissolved in dry tetrahydrofuran (5 mL), cooled to −40° C., and treated with n-butyllithium (1.58M in hexanes, 0.384 mL, 0.606 mmol). After 40 min at this temperature, pentafluorophenyl chlorothionoformate (0.086 mL, 0.536 mmol) was added neat by syringe. The reaction mixture was stirred at −20° C. for 90 min, quenched with saturated ammonium chloride solution, and extracted with ethyl acetate. The ethyl acetate layer was dried and concentrated. The residue was purified by silica gel chromatography (being eluted with 40% ethyl acetate in hexane) to afford the title compound as a foam (320 mg, Y: 74%).

(b) 10-Desacetoxy-7-O-triethylsilylbacctain III

The product of step (a) (119 mg, 0.135 mmol) was dissolved in dry toluene (3 mL) and treated with AIBN (2 mg). The solution was degassed with dry nitrogen, then tributyltin hydride (0.055 mL, 0.202 mmol) was added. Subsequently, the solution was heated at 90° C. for 1 h. The solvent was then evaporated and silica gel chromatography of the residue (being eluted with 40% ethyl acetate in hexane) gave the title compound (87 mg, Y: 99%) as a colorless foam.

(c) 10-Desacetoxybaccatin III

The product of step (b) (120 mg, 0.187 mmol) was dissolved in acetonitrile (3.5 mL) and the solution was cooled to −10° C. Concentrated HCl (36%, 0.060 mL) was added, and the solution was stirred for 30 min. The mixture was diluted with ethyl acetate (75 mL), and washed with saturated aqueous sodium bicarbonate and brine, then dried and concentrated. The residue was purified by flash silica chromatography (being eluted with 70% ethyl acetate in hexane) to afford 10-deacetyloxybaccatin III as a foam (75 mg, Y: 76%).

Preparation 8. 10-Desacetoxy-7-deoxybaccatin III

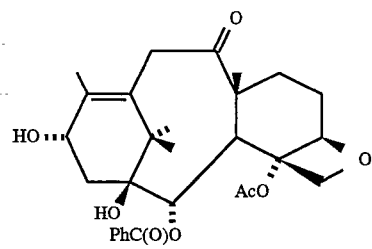

(a) 7-O-[(Methylthio)thiocarbonyl]-10-desacetoxybaccatin III

10-Desacetoxybaccatin III (75 mg, 0.142 mmol) was dissolved in dry tetrahydrofuran (2 mL) and carbon disulfide (0.5 mL). Sodium hydride (60% in mineral oil, 8.5 mg, 0.213 mmol) was then added, and the mixture was stirred at room temperature for 2 h. Iodomethane (0.026 mL, 0.426 mmol) was added, and the reaction was allowed to proceed overnight. The solvent was then removed and the residue was purified by silica gel chromatography (being eluted with 50–70% ethyl acetate in hexane) to give the title compound as a foam (46.4 mg, Y: 53%).

(b) 10-desacetoxy-7-deoxy-baccatin III

The product of step (a) (36 mg, 0.058 mmol) was refluxed in benzene (1 mL) in the presence of AIBN (2 mg) and tributyltin hydride (0.079 mL, 0.290 mmol) under an argon atmosphere for 3 h. Concentration of the reaction mixture and flash silica gel chromatography of the residue (being eluted with 40% ethyl acetate in hexanes) followed by HPLC (high pressure liquid chromatography) separation from other components afforded the title compound as a foam (16.8 mg, Y: 56%).

Alternate Run:

To a solution of 7-O-[(methylthio)carbonothioyl]-13-O-triethylsilylbaccatin III (product of preparation I, step (b), 416.3 mg, 0.527 mmol) in dry toluene (10.5 mL) was added catalytic amount of AIBN, and the resulting solution was degassed with dry $N_2$ for 5 min. Tributyltin hydride (708.7 uL, 2.63 mmol) was the added and the reaction mixture was heated at 100° C. for 2 h., after which another portion of tributyltin hydride (425.3 uL, 1.581 mmol) was added. The reaction mixture was heated for 5.5 h at 100° C., and then allowed to cool to room temperature. Silica gel chromatography (eluted with 20% ethyl acetate in hexanes) afforded 7-deoxy-10-desacetoxy-13-O-(triethysilyl)baccatin III (320 mg, Y: 97%).

To a solution of the product of the above step (160 mg, 0.255 mmol) in dry tetrahydrofuran (2 mL) at room temperature was added tetrabutylammonium fluoride (766 uL, 1M, 0.766 mmol). The reaction mixture was stirred for 1 h at room temperature. The solvent was removed and the residue was chromatographed on silica gel (eluted with 50–70% ethyl acetate in hexanes) to afford the desired title product (115 mg, Y: 87.9%).

Preparation 9. (3R, 4S)-1-t-Butoxycarbonyl-4-phenyl-3-triethylsilyloxy-2-azetidinone

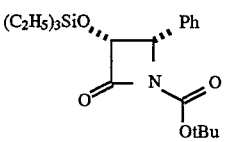

To a stirred solution of (3R,4S)-4-phenyl-3-triethylsilyloxy-2-azetidinone (2.200 g, 7.92 mmol) in dry tetrahydrofuran (25 mL) was added N,N-diisopropylethylamine (1.65 mL, 9.510 mmol, 1.2 equiv) at 0° C. under an argon atmosphere. The solution was stirred for 5 min followed by the addition of di-t-butyl dicarbonate (2.080 g, 9.510 mmol, 1.2 equiv) and 4-dimethylaminopyridine (193.6 mg, 1.581 mmol, 0.20 equiv). The reaction mixture was stirred at 0° C. for 60 min., then diluted with ethyl acetate (25 mL). The resulting solution was washed with brine, 10% NaHCO$_3$, 10% HCl solution, dried (MgSO$_4$), and concentrated to give a crude compound (oil). The compound was further purified by silica gel flash chromatography (being eluted with 15% ethyl acetate in hexanes) to afford the title compound as a white solid (2.4 g, Y: 83%).

Preparation 10. (±)-cis-3-Acetyloxy-4-phenylazetidin-2-one

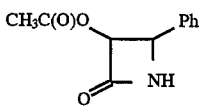

(a) To a 1 L, 3-necked round bottom flask equipped with a thermometer, magnetic stirrer and dropping funnel was added hydrobenzamide (30.00 g, 100.5 mmol) and ethyl acetate (150 mL). With stirring and under a blanket of argon, the reaction mixture was cooled to 5° C. and triethylamine (16.8 mL, 121 mmol) was added. A solution of acetoxyacetyl chloride (12.4 mL, 116 mmol) in ethyl acetate (300 mL) was then added dropwise over a 90 min period. After 16 h at this temperature, the reaction mixture was allowed to warm to 20° C. (1.5 h) and transferred to a separatory funnel. The organic layer was washed successively with aqueous NH$_4$Cl (sat) (150 mL, 100 mL), aqueous NaHCO$_3$ (saturated) (120 mL) and brine (120 mL). For purposes of characterization, the title compound can be isolated at this stage by drying the organic phase over MgSO$_4$, filtering, and removing the solvent in vacuo. This provided (±)-cis-3-acetyloxy-1-[(phenyl)(benzylidenimino)methyl]-4-phenylazetidin-2-one in quantitative crude yield as a red glass.

(b) A solution of the compound obtained in part (a) in ethyl acetate (500 mL) was carefully transferred, under a stream of argon, to a 2.0 L Parr flask containing 10% palladium on activated charcoal (6.00 g). This mixture was treated with hydrogen (4 atm) for 20 h whereupon the catalyst was removed by filtration through a pad of Celite. The filter cake was slurried in ethyl acetate (200 mL), stirred (10 min) and filtered. The filter cake was rinsed with ethyl acetate (100 mL) and the filtrates combined. The organic layer was washed with 10% HCl (300 mL) and both layers filtered through a sintered glass funnel to remove the white precipitate (dibenzylamine HCl) which was rinsed with ethyl acetate (100 mL). The phases were separated and the organic layer was washed with another portion of 10% HCl (200 mL). The combined 10% HCl washes were re-extracted with ethyl acetate (200 mL) and the combined organic layers were washed with aqueous NaHCO$_3$ (saturated) (300 mL) and brine (250 mL). The organic layer was dried over MgSO$_4$, filtered and concentrated in vacuo to a final volume of 75 mL. This mixture was cooled to 4° C. and the precipitated product isolated by filtration. The filter cake was washed with hexane (200 mL) to provide 16.12 g (78.1% overall yield from hydrobenzamide) of the title compound as white needles.

mp=150°–151° C.

Preparation 11. (±)-cis-3-Triethylsilyloxy-4-(2-furyl)-N-t-butoxycarbonylazetidin-2-one

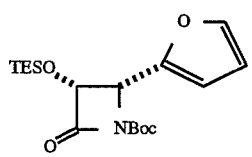

(a) The procedure described in Preparation 10, part (a), was followed except that hydrofuramide [i.e. 2-furyl-CH=(N=CH-2-furyl)$_2$] was used instead of hydrobenzamide and the reaction was performed on 18.6 mmol (vs 100 mmol) scale. Thus, hydrofuramide (5.00 g, 18.6 mmol), triethylamine (3.11 mL, 22.3 mmol) and acetoxyacetyl chloride (2.30 mL, 21.4 mmol) gave 6.192 g (Y: 90.4%) of (±)-cis-3-acetyloxy-1-[(2-furyl)(2-furylmethylenimino)methyl]-4-(2-furyl)azetidin-2-one as a pale red syrup.

(b) The procedure described in Preparation 10, part (b), was followed except that the product was isolated by preparative TLC and the reaction was performed on the 2.7 mmol scale based on the original amount of hydrofuramide. Thus, the crude product obtained in part (a) above was re-dissolved in ethyl acetate (50 mL) and added to 10% palladium on activated charcoal (150 mg). Purification of the crude solid by preparative TLC (2 mm silica gel, eluted with 1:1 ethyl acetate/hexane) gave 386 mg (65.8% corrected overall yield from hydrofuramide) (±)-cis-3-(acetyloxy)-4-(2-furyl)azetidin-2-one as a yellow solid. This was recrystallized from ethyl acetate/hexane.

mp=118°–119° C.

(c) The compound obtained in part (b) above (3.78 g, 19.4 mmol) in 60 mL of methanol was stirred with K$_2$CO$_3$ (20 mg, 0.14 mmol) for 90 min and the solution neutralized with Dowex 50W-X8 and filtered. The filtrate was concentrated and the residue dissolved in 80 mL of anhydrous THF and stirred at 0° C. with imidazole (1.44 g, 21.2 mmol) and TESCl (3.4 mL, 20.2 mmol) for 30 min. The solution was diluted with ethyl acetate and washed with brine, dried over MgSO$_4$ and concentrated. The residue was chromatographed over silica gel (eluted with 3:1 hexane/ethyl acetate) to give 4.47 g (Y: 86%) of (±)- cis-3-triethylsilyloxy-4-(2-furyl)-azetidin-2-one as a colorless oil.

(d) The product of part (c) (2.05 g, 7.7 mmol) in 30 mL of dichloromethane was stirred at 0° C. with diisopropylethyl amine (1.5 mL, 8.6 mmol) and di-t-butyl dicarbonate (2.0 g, 9.2 mmol) in addition to a catalytic amount of dimethylaminopyridine (DMAP). The solution was diluted with dichloromethane and washed with brine, dried over MgSO$_4$ and concentrated. The residue was chromatographed over silica gel (eluted with 8:1 hexane/ethyl acetate) to give 2.0 g (Y: 70%) of the title compound as a waxy solid.

The racemic mixture obtained in part (b) may be used as substrate for enzymatic hydrolysis using a lipase such as PS-30 from *Pseudomonas sp.* (Amano International Co.) to give (3R,4R)-3-hydroxy-4-(2-furyl)-azetidin-2-one. The method of enzymatic resolution using the lipase PD-30 and other enzymes is disclosed in our co-pending application U.S. Ser. No. 092,170, filed Jul. 14, 1993 which is hereby incorporated by reference in its entirety.

The procedure in parts (c) and (d) was followed using (3R,4R)-3-hydroxy-4-(2-furyl)-azetidin-2-one to provide (3R,4R)-N-(t-butoxycarbonyl)-3-triethylsilyoxy-4-(2-furyl) azetidine-2-one.

Preparation 12. (±)- cis-3-Triethylsilyloxy-4-(2-thienyl)-N-t-butoxycarbonylazetidin-2-one

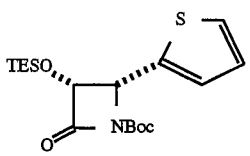

(a) The procedure described in Preparation 10, step (a) was followed except that hydrothienamide [i.e. 2-thienyl-CH—(N=CH-2-thienyl)$_2$] was used instead of hydrobenzamide. Thus, hydrothienamide (30 g, 94.7 mmol), thiethylamine (15.84 mL, 114 mmol) and acetoxyacetyl chloride (11.6 mL, 108 mmol) provided (±)-cis-3-acetyloxy-1-[(2-thienyl)(2-trienylmethylenimino)methyl]-4-(2-thienyl) azetidin-2-one as viscous oil.

(b) A 70% aqueous solution of acetic acid (0.35 mL glacial acetic acid and 0.15 mL water) was added in one portion to a stirred solution of the product obtained in part (a) (0.431 g, 1.03 mmol) in dichloromethane (2.93 ml) at 25° C. The reaction mixture was brought to reflux and stirred for 2.5 h. The reaction was diluted with 50 mL dichloromethane and then washed with two 75 mL portions of saturated aqueous sodium bicarbonate and then one 50 mL portion of saturated brine. The organic extract was concentrated in vacuo to a brown oil, dissolved in a minimal amount of dichloromethane, and then placed on a silica gel column measuring 4" by 0.5". Elution using a gradient of 10 through 60% EtOAc in hexane provided less polar sideproducts and then (±)-cis-3-acetyloxy-4-(2-thienyl)azetidin-2-one (0.154 g, Y: 75%) as a white solid.

(c) A solution of the product obtained in part (b) (2.5 g, 11.8 mmol) was dissolved in methanol (10 mL) and treated with saturated aqueous sodium bicarbonate (10 mL) and the resulting slurry was allowed to stir at ambient temperature for 3 h. The reaction was then diluted with ethyl acetate (20 mL) and washed with water (15 mL). The aqueous fraction was back extracted several times with ethyl acetate and the combined organic fractions were dried (MgSO$_4$) and concentrated to give a yellow solid (Y: 1.7 g). The crude material was dissolved in dry tetrahydrofuran (20 mL) and the solution was cooled to 5° C. in an ice/water bath. Imidazole (752 mg, 1.1 eq) was then added. After stirring 5 min, triethylchlorosilane (1.85 mL, 1.1 eq) was added dropwise. The resulting suspension was allowed to stir for 3 h at that temperature; then the solids were removed by filtration. The organic fraction was washed with water (2×20 mL) then dried (MgSO$_4$) and concentrated. The crude product was purified by silica gel column chromatography (eluted with hexanes/ethyl acetate 7:3) to give (±)-cis-3-triethylsilyloxy-4-(2-thienyl)-azetidin-2-one as a colorless solid (1.5 g, Y: 45%). m.p. 70°–71° C.

Alternate Run:

The product obtained in part (b) (2.0 g, 9.37 mmol) in 40 mL of methanol was stirred with K$_2$CO$_3$ (60 mg, 0.43 mmol) for 30 min and the solution neutralized with Dowex 50W-X8 and filtered. The filtrate was concentrated and the residue dissolved in 50 mL of anhydrous THF and stirred at 0° C. with imidazole (0.85 g, 11.3 mmol) and TESCl (1.9 mL, 12.5 mmol) for 30 min. The solution was diluted with ethyl acetate and washed with brine, dried over MgSO$_4$ and concentrated. The residue was chromatographed over silica gel (eluted with 3:1 hexane/ethyl acetate) to give 2.13 g (Y: 86%) of the title product as a colorless oil.

(d) A solution of the product obtained in part (c) (425.7 mg, 1.48 mmol) was dissolved in dichloromethane (10 mL) and cooled to 5° C. in an ice/water bath. The reaction was treated with a catalytic amount of DMAP followed by diisopropylethylamine (TESCl, 0.25 mL, 1.0 eq) then by di-t-butyl dicarbonate (388.4 mg, 1.2 eq). After stirring 2 h at that temperature the reaction was quenched with saturated aqueous sodium bicarbonate (5 mL) and the organic fraction was washed with water (5 mL) then dried (MgSO$_4$), passed through a short plug of silica gel and concentrated to give the desired product as a colorless oil (525.3 mg, Y: 93%).

Prepartion 13. (3R, 4R)-3-Triethylsilyloxy-4-(2-furyl)-N-n-butyloxycarbonylazetidin-2-one

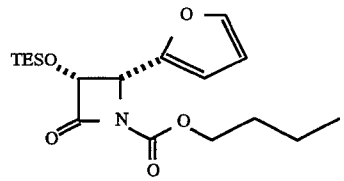

(3R,4R)-3-Triethylsilyloxy-4-(2-furyl)azetidin-2-one (0.58 g, 2.17 mmol) in 30 mL of dichloromethane was stirred with diisopropylethyl amine (0.4 mL, 2.30 mmol) and butylchloroformate (0.3 mL, 2.36 mmol) in addition to a catalytic amount of DMAP. The solution was stirred for 1 h and diluted with dichloromethane and washed with brine, dried over MgSO$_4$ and concentrated. The residue was chromatographed over silica gel (eluted with 3:1 hexane/ethyl acetate) to give 523 mg of product (Y: 65%); IR(KBr) 1820, 1734, 1318, 1018, 734 cm$^{-1}$; $^1$H-NMR (CDCl$_3$, 300 MHz) δ 7.38 (m, 1H), 6.35 (m, 2H), 5.09 (ABq, J=15.5, 5.6 Hz, 2H), 4.14 (m, 2H), 1.56 (m, 2H), 1.28 (s, 2H), 0.87 (t, J=8.7 Hz, 3H), 0.82 (t, J=7.9, 9H), 0.50 (m, 6H); $^{13}$C-NMR (CDCl$_3$, 75.5 Hz) δ 165.4, 149.1, 147.6, 142.9, 110.5, 109.9, 77.7, 66.6, 55.9, 30.5, 18.8, 13.6, 6.3, 4.3; DCIMS M+H calcd for C$_{18}$H$_{29}$NO$_5$Si: 368, Found: 368.

Preparation 14. (3R,4R)-3-Triethylsilyloxy-4-(2-furyl)-N-isopropyloxycarbonylazetidin-2-one

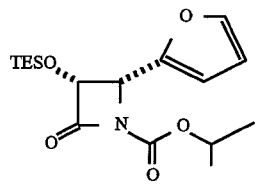

(3R, 4R)-3-Triethylsilyloxy-4-(2-furyl)azetidin-2-one (0.51 g, 1.91 mmol) in 25 mL of dichloromethane was stirred with diisopropylethyl amine (0.78 mL, 4.4 mmol)

and i-propylchloroformate (4.0 mL, 1.0M in toluene, 4.0 mmol) in addition to a catalytic amount of DMAP. The solution was stirred for 1 h and diluted with dichloromethane and washed with brine, dried over MgSO$_4$ and concentrated. The residue was chromatographed over silica gel (eluted with 5:1 hexane/ethyl acetate) to give 649 mg of the title product (Y: 96%); IR(KBr) 1822, 1812, 1716, 1374, 1314, 1186, 1018, 1004, 746 cm$^{-1}$; $^1$H-NMR (CDCl$_3$, 300 MHz) δ 7.39 (m, 1H), 6.35 (m, 2H), 5.08 (ABq, J=15.6, 5.6 Hz, 2H), 4.96 (d, J=10.0 Hz, 1H), 1.25 (d, J=6.3 Hz, 3H), 1.17 (d, J=6.3 Hz, 3H)), 0.83 (t, J=7.8, 9H), 0.50 (m, 6H); $^{13}$C-NMR (CDCl$_3$, 75.5 Hz) δ 165.5, 148.6, 147.8, 142.9, 110.5, 109.9, 77.6, 71.1, 55.9, 21.7, 21.6, 6.3, 4.4; DCIMS M+H calcd for C$_{17}$H$_{28}$NO$_5$Si: 354, Found: 354.

Preparation 15. (±)-cis-3-Triethylsilyloxy-4-isobutenyl-N-t-butoxycarbonylazetidin-2-one (a) N-4-methoxy-N-(3-methyl-2-butenyl) benzenamine

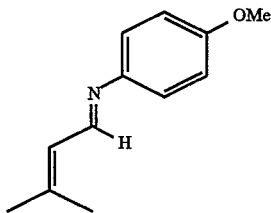

A solution of p-anisidine (5.7 g, 46.3 mmol) was dissolved in diethylether (100 mL) and was treated with a catalytic amount of p-toluensulfonic acid (10 mg). To this was added 3-methyl-2-butenal (2.67 mL, 50.9 mmol) in one portion and the reaction was allowed to stir at ambient temperature for 16 h. The solvent was then evaporated on a rotary evaporator at 0.5 torr to furnish the desired imine (8.7 g, 100%) as a brown oil; $^1$H NMR 300 MHz, CDCl$_3$): δ 8.38 (d, 1H, J=9.5 Hz), 7.11 (dd, 2H, J=2.2, 6.7 Hz), 6.88 (dd, 2H, J=2.2, 6.7 Hz), 6.22–6.18 (m, 1H), 3.81 (s, 3H), 2.01 (s, 3H), 1.95 (s, 3H).

(b) (±)-cis-N-(4-methoxyphenyl)-3-acetyloxy-4-isobutenylazetidin-2-one

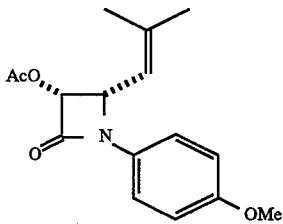

A solution of acetoxyacetyl chloride (6.9 g, 50.5 mmol) was dissolved in ethyl acetate (100 mL) and cooled to −30° C. under an inert atmosphere. To this solution was added triethylamine (7.0 mL, 50.5 mmol) over a 5 min period. The resulting white slurry was then treated with an ethyl acetate solution of N-4-methoxy-N-(3-methyl-2-butenyl) benzenamine (8.7 g, 40 mL) dropwise over a 20 min period. The resulting green-brown slurry was then gradually allowed to warm to ambient temperature over a 4 h period. The slurry was then filtered through a pad of celite and the filtrate was washed with water then brine. The organic fraction was dried (MgSO$_4$) and concentrated to give a brown oil. The crude product was purified by careful silica gel chromatography (eluted with hexanes/ethyl acetate 8:2) to furnish an orange oil which solidified on standing. This was recrystallized from dichloromethane/hexanes to furnish the desired product as a pale yellow solid (4.4 g, 32%); $^1$H NMR (300 MHz, CDCl$_3$): δ 7.32 (d, 2H, J=9.1 Hz), 6.86 (d, 2H, J=9.1 Hz), 5.59 (dd, 1H, J=3.0, 7.8 Hz), 5.14–5.10 (m, 1H), 4.96 (dd, 1H, J=4.8, 9.3 Hz), 3.77 (s, 3H), 2.11 (s, 3H,), 1.81 (s, 3H), 1.78 (s, 3H).

(c) (±)-cis-3-Acetyloxy-4-isobutenylazetidin-2-one

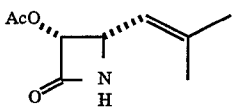

A solution of the (±)-cis-N-(4-methoxyphenyl)-3-acetyloxy-4-isobutenylazetidin-2-one (4.88 g, 16.2 mmol) was dissolved in acetonitrile (50 mL) and cooled to 0°–5° C. in an ice bath. To this was added a cold solution of ceric ammonium nitrate (26.6 g, 48.6 mmol, 50 mL) in one portion. The deep red reaction was allowed to stir for 10 min and during that time the color gradually lightened to orange. The cold solution was transferred to a separatory funnel, diluted with water, and extracted with ethyl acetate. The organic fraction was washed with several portions of 10% aqueous sodium sulfite, followed by saturated aqueous sodium bicarbonate. The organic fraction was dried (MgSO$_4$) and concentrated to give the desired product (2.71 g, 91%) as a yellow-orange solid that was used directly in the next step; $^1$H NMR (300 MHz, CDCl$_3$): δ 6.11 (bs, 1H), 5.73 (dd, 1H, J=2.2, 4.7 Hz), 5.12–5.08 (m, 1H), 4.63 (dd, 1H, 4.7, 9.1 Hz), 2.09 (s, 3H), 1.75 (s, 3H), 1.67 (s, 3H).

(d) (±)-cis-3-Triethylsilyloxy-4-isobutenylazetidin-2-one

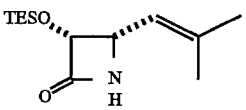

(±)-cis-3-Acetyloxy-4-isobutenylazetidin-2-one (1.47 g, 8.0 mmol) was dissolved in methanol (15 mL) and was stirred with K$_2$CO$_3$ (110.5 mg, 0.8 mmol) for 3 h at ambient temperature. The solution was then neutralized with Dowex 50W-X8 resin and then filtered. The filtrate was concentrated and the crude solid was dissolved in THF (25 mL) and cooled to 5° C. in an ice bath. Imidazole (544.0 mg, 8.0 mmol) was added and once dissolved, triethylsilyl chloride (1.34 mL, 8.0 mmol) was added dropwise via syringe. The resulting slurry was allowed to warm to ambient temperature and stir overnight. The solution was filtered and the filtrate was washed with water, then brine. The organic fraction was dried (MgSO$_4$) and concentrated. The crude solid was purified by silica gel chromatography (eluted with hexanes/ethyl acetate 3:1) to furnish the desired product (612 mg, 30%) as a pale yellow solid; $^1$H NMR (300 MHz, CDCl$_3$): δ 5.87 (bs, 1H), 5.31–5.26 (m, 1H), 4.90 (dd, 1H, J=2.2, 4.7 Hz), 4.42 (dd, 1H, J=4.7, 9.3 Hz), 1.74 (s, 3H), 1.28 (s, 3H), 0.98–0.91 (m, 9H), 0.71–0.55 (m, 6H).

(e) (±)-cis-3-Triethylsilyloxy-4-isobutenyl-N-t-butoxycarbonylazetidin-2-one

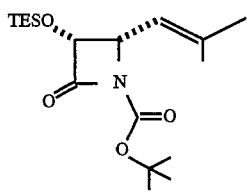

(±)-cis-3-Triethylsilyloxy-4-isobutenylazetidin-2-one (1.01 g, 3.95 mmol) was dissolved in dichloromethane (20 mL) and was treated with diisopropylethylamine (0.68 mL, 3.95 mmol) and a catalytic amount of dimethylaminopyridine. To this solution was added di-t-butyl dicarbonate (1.02 g, 4.68 mmol) and the solution was allowed to stir for 24 h at ambient temperature. The solution was then diluted with additional dichloromethane and washed with water then brine. The organic fraction was dried (MgSO$_4$) and concentrated. The residue was purified by silica gel chromatography (eluted with hexanes/ethyl acetate 8:2) to give the desired product (1.26 g, 90%) as a colorless oil; $^1$HNMR (300 MHz, CDCl$_3$): δ 5.24 (d, 1H, J=9.6 Hz), 4.86 (d, 1H, J=5.7 Hz), 4.72 (dd, 1H, J=6.0, 9.9 Hz), 1.78 (d, 3H, J=1.1 Hz), 1.75 (d, 3H, J=1.1 Hz), 1.47 (s, 9H), 0.96–0.91 (m, 9H), 0.64–0.55 (m, 6H).

The procedure described above in Preparations 9, 11(d), 12(d), 13, 14, and 15(e) may be adapted to the preparation of other N-substituted azetidinones useful in the preparation of compounds of the invention.

Examples of such azetidinones are listed in the following table; P below is a hydroxy protecting group such as triethyl silyl, triisopropylsilyl and ethoxyethyl.

$$\underset{\text{NH}}{\overset{\text{PO}_{\text{\tiny{...}}}\quad R^5}{\square}} + R^4(O)_pC(O)-L \longrightarrow \underset{\overset{\text{N}}{\underset{O}{\parallel}}(O)_pR^4}{\overset{\text{PO}_{\text{\tiny{...}}}\quad R^5}{\square}}$$

| L | R$^4$(O)$_p$ | R$^5$ |
|---|---|---|
| Cl | Ph | 4-CH$_3$O—Ph— |
| | | 3,4-diCH$_3$O—Ph— |
| | | Ph— |
| | | 4-F—Ph— |
| | | 4-CF$_3$—Ph— |
| | | 2-furanyl- |
| | | 2-thienyl- |
| | | PhCH=CH— |
| | | 2-furanyl-CH=CH— |
| | | (CH$_3$)$_2$CHCH$_2$— |
| | | C$_6$H$_{11}$—CH$_2$— |
| | | (CH$_3$)$_2$CH— |
| | | PhCH$_2$CH$_2$— |
| | | C$_6$H$_{11}$—CH$_2$CH$_2$— |
| | | CH$_3$CH$_2$CH$_2$— |
| | | 4-Cl—Ph |
| | | 2-F—Ph |
| | | 3-F—Ph |
| | | 4-CH$_3$—Ph |
| | | (CH$_3$)$_2$C=CH |
| Cl | 4-CH$_3$O—Ph— | 3,4-diCH$_3$O—Ph— |
| | | 4-CF$_3$—Ph— |
| | | 2-furanyl- |
| | | PhCH=CH— |
| | | (CH$_3$)$_2$CHCH$_2$— |
| | | C$_6$H$_{11}$—CH$_2$— |
| | | PhCH$_2$CH$_2$— |
| (CH$_3$)$_3$COCO$_2$— | (CH$_3$)$_3$CO— | 4-CH$_3$O—Ph— |
| | | 4-F—Ph— |
| | | 4-CF$_3$—Ph— |
| | | PhCH=CH— |
| | | (CH$_3$)$_2$CH— |
| | | PhCH$_2$CH$_2$— |
| | | C$_6$H$_{11}$—CH$_2$CH$_2$— |
| | | CH$_3$CH$_2$CH$_2$— |
| Cl | CH$_3$— | 4-CH$_3$O—Ph— |
| | | Ph— |
| | | 4-F—Ph— |
| | | 2-furanyl- |
| | | 2-furanyl-CH=CH— |
| | | PhCH$_2$CH$_2$— |
| | | C$_6$H$_{11}$—CH$_2$CH$_2$— |
| | | CH$_3$CH$_2$CH$_2$— |

Preparation 16. 10-deoxytaxotere

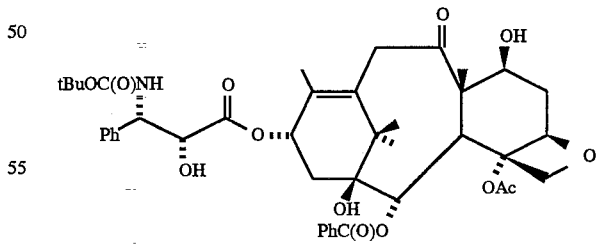

10-Desacetoxy-7-O-triethylsilylbaccatin III (100 mg, 0.156 mmol) was placed in a flask under argon and dissolved in dry tetrahydrofuran (1.5 mL). Upon cooling to −40° C., n-butyllithium (1.45M in hexanes, 0.119 mL, 0.170 mmol) was added dropwise, followed by (3R,4S)-1-tert-butoxycarbonyl-4-phenyl-3-triethylsilyloxy-2-azetidinone (94.2 mg, 0.25 mmol) in tetrahydrofuran (0.5 mL) over a period of 2 min. The mixture was immediately warmed to 0° C. and stirred for 45 min before being quenched with saturated ammonium chloride (3 mL). The mixture was extracted with ethyl acetate, dried, and concentrated. Silica gel chromatography (eluted with 30% ethyl acetate in hexane) afforded 10-deoxy-2',7-bis-O-(triethylsilyl)taxotere as a foam (125 mg, Y: 76%). This compound (100 mg, 0.098 mmol) was immediately dissolved in acetonitrile (2 mL) at −5° C. and treated with hydrochloric acid (0.037 mL, 36%, 12M). The mixture was stirred for 2 h at −5° C., then quenched with aqueous bicarbonate, extracted with ethyl acetate, and dried. Evaporation of the solvent was followed by silica gel chromatography (eluted with 75% ethyl acetate in hexane) to afford the title compound as a foam (80.5 mg, Y: 80%).

The general procedure provided in Preparation 16 may be adapted to the preparation of other compounds of formula (Ia) by starting with the appropriate baccatin III component and the azetidinone component; examples of other compounds of formula (Ia) are listed in the following table. It will be understood that even though the compounds below are shown with free hydroxy groups, with the judicious selection of the various hydroxy protecting groups, any one of the protecting groups at the 2'-, 7- or 10-position may be selectively removed without affecting other protecting groups present.

| $R^{2'}$ | $R^{2a}$ | $R^{3a}$ | $R^4(O)_p$ | $R^5$ |
|---|---|---|---|---|
| H | OH | AcO | Ph | 4-CH$_3$O—Ph— |
|  |  |  |  | 3,4-diCH$_3$O—Ph— |
|  |  |  |  | Ph— |
|  |  |  |  | 4-F—Ph— |
|  |  |  |  | 4-CF$_3$—Ph— |
|  |  |  |  | 2-furanyl- |
|  |  |  |  | 2-thienyl- |
|  |  |  |  | PhCH=CH— |
|  |  |  |  | 2-furanyl-CH=CH— |
|  |  |  |  | (CH$_3$)$_2$CHCH$_2$— |
|  |  |  |  | C$_6$H$_{11}$—CH$_2$— |
|  |  |  |  | (CH$_3$)$_2$CH— |
|  |  |  |  | PhCH$_2$CH$_2$— |
|  |  |  |  | C$_6$H$_{11}$—CH$_2$CH$_2$— |
|  |  |  |  | CH$_3$CH$_2$CH$_2$— |
|  |  |  |  | 4-Cl—Ph |
|  |  |  |  | 2-F—Ph |
|  |  |  |  | 3-F—Ph |
|  |  |  |  | 4-CH$_3$—Ph |
| H | OH | OH | (CH$_3$)$_3$CO | 4-CH$_3$O—Ph— |
|  |  |  |  | Ph |
|  |  |  |  | 4-F—Ph— |
|  |  |  |  | 4-CF$_3$—Ph— |
|  |  |  |  | 2-furanyl- |
|  |  |  |  | 2-thienyl- |
|  |  |  |  | PhCH=CH— |
|  |  |  |  | C$_6$H$_{11}$—CH$_2$— |
|  |  |  |  | (CH$_3$)$_2$CH— |
|  |  |  |  | PhCH$_2$CH$_2$— |
| OH | H |  | Ph | 4-CH$_3$O—Ph— |
|  |  |  |  | 3,4-diCH$_3$O—Ph— |
|  |  |  |  | 4-F—Ph— |
|  |  |  |  | 4-CF$_3$—Ph— |
|  |  |  |  | 2-furanyl- |
|  |  |  |  | 2-thienyl- |
|  |  |  |  | PhCH=CH— |
|  |  |  |  | 2-furanyl-CH=CH— |
|  |  |  |  | (CH$_3$)$_2$CHCH$_2$— |
|  |  |  |  | C$_6$H$_{11}$—CH$_2$— |
|  |  |  |  | (CH$_3$)$_2$CH— |
|  |  |  |  | PhCH$_2$CH$_2$— |
|  |  |  |  | C$_6$H$_{11}$—CH$_2$CH$_2$— |
|  |  |  |  | CH$_3$CH$_2$CH$_2$— |
| H | H |  | (CH$_3$)$_3$CO | 4-CH$_3$O—Ph— |
|  |  |  |  | 3,4-diCH$_3$O—Ph— |
|  |  |  |  | Ph— |
|  |  |  |  | 4-F—Ph— |
|  |  |  |  | 4-CF$_3$—Ph— |
|  |  |  |  | 2-furanyl- |
|  |  |  |  | 2-thienyl- |
|  |  |  |  | PhCH=CH— |
|  |  |  |  | 2-furanyl-CH=CH— |
|  |  |  |  | (CH$_3$)$_2$CHCH$_2$— |
|  |  |  |  | C$_6$H$_{11}$—CH$_2$— |
|  |  |  |  | (CH$_3$)$_2$CH— |
|  |  |  |  | PhCH$_2$CH$_2$— |
|  |  |  |  | C$_6$H$_{11}$—CH$_2$CH$_2$— |
|  |  |  |  | CH$_3$CH$_2$CH$_2$— |
| H | OH | AcO | 2-naphthyl | Ph |
|  |  |  | 4-OH—Ph |  |
|  |  |  | 4-CH$_3$O—Ph |  |
|  |  |  | 4-F—Ph |  |
|  |  |  | (CH$_3$)$_3$CO— |  |
|  |  |  | CH$_3$— |  |
|  |  |  | (CH$_3$)$_2$CH— |  |
|  |  |  | CH$_2$=CHCH$_2$— |  |
|  |  |  | 4-Cl—Ph |  |
| F | H | AcO | (CH$_3$)$_3$CO— | Ph |
| F | H | OH | Ph | Ph |
| H | H | AcO | Ph | 4-CH$_3$O—Ph— |
|  |  |  |  | 3,4-diCH$_3$O—Ph— |
|  |  |  |  | Ph— |
|  |  |  |  | 4-F—Ph— |
|  |  |  |  | 4-CF$_3$—Ph— |
|  |  |  |  | 2-furanyl- |
|  |  |  |  | 2-thienyl- |
|  |  |  |  | PhCH=CH— |
|  |  |  |  | 2-furanyl-CH=CH— |
|  |  |  |  | (CH$_3$)$_2$CHCH$_2$— |
|  |  |  |  | C$_6$H$_{11}$—CH$_2$— |
|  |  |  |  | (CH$_3$)$_2$CH— |
|  |  |  |  | PhCH$_2$CH$_2$— |
|  |  |  |  | C$_6$H$_{11}$—CH$_2$CH$_2$ |
|  |  |  |  | CH$_3$CH$_2$CH$_2$— |

Preparation 17. Bis(methylthiomethyl)ether

CH$_3$SCH$_2$OCH$_2$SCH$_3$

Sodium iodide (8.23 g, 55.23 mmol) was added to a solution of 1,1'-dichlorodimethyl ether (3.0 g, 26.3 mmol) in acetone (100 ml) at 0° C. and the mixture was stirred at this temperature for 20 min. Sodium thiomethoxide (1.84 g, 5.23 mmol) was then added in four portions and the resulting solution was stirred for an additional 1 h. The heterogeneous solution was then filtered through a pad of celite and the filtrate concentrated in vacuo. The residual oil was partitioned between ethyl acetate and saturated aqueous sodium bicarbonate solution. The aqueous layer was removed and further extracted with ethyl acetate. The combined organics were then treated with a 1:1 (v:v) mixture of saturated aqueous sodium bicarbonate and 5% aqueous sodium thiosulfate solution. The organics were then washed with brine, dried over sodium sulfate and concentrated in vacuo. The residual oil was purified via flash chromatography (30:1, hexanes:ethyl acetate) to provide 1.9 g of a yellow oil which was subsequently distilled using a kugelrhor apparatus (120°–130° C., 20 mmHg) yielding 1.5 g (45%) of the title compound as colorless oil:

$^1$H NMR (300 MHz, CDCl3) δ 4.73 (4H, s), 2.15 (6H, s).

Preparation 18. Dibenzyl Methylthiomethyl Phosphate

CH$_3$SCH$_2$OP(O)(OBu)$_2$

To a solution of bis(methylthiomethyl)ether (30 mg, 2.34 mmol) and molecular sieves (300 mg) in THF (100 ml) at room temperature was added dibenzyl phosphate (2.74 g, 9.85 mmol) followed by N-iodosuccinimide (608 mg, 2.71 mmol) and the solution was stirred for 4 h. The reaction mixture was then diluted with ethyl acetate and filtered through a pad of celite. The filtrate was treated with a 1:1 (v:v) solution of saturated aqueous sodium bicarbonate and 5% aqueous sodium thiosulfate. The colorless organic extract was then washed with brine, dried over sodium sulfate and concentrated in vacuo to provide 600 mg (69%) of the title compound:

$^1$H NMR (300 MHz, CDCl3) δ 7.35 (10H, s), 5.29 (2H, d, J=12.2 Hz), 5.08 (4H, dd, J=8.0, 1.0 Hz), 4.68 (2H, s), 2.10 (3H, s).

EXAMPLES

The following examples are provided to illustrate the synthesis of representative compounds of the instant invention and are not to be construed as limiting the scope of the invention in any manner. One skilled in the art will be able to adapt these methods, without undue experimentation, to the synthesis of compounds within the scope of this invention but not specifically disclosed.

Example 1

7-O-phosphonooxymethylpaclitaxel and Its Monosodium Salt (a) Preparation of 7-O-methylthiomethylpaclitaxel

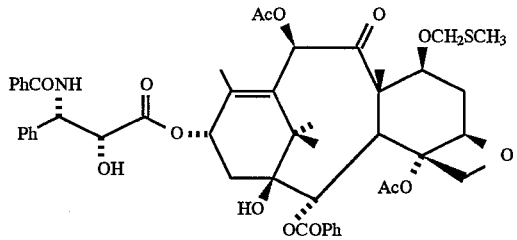

Benzoyl peroxide (0.98 g, 4 mmol) was added to a vigorously stirred mixture of paclitaxel (0.85 g, 1 mmol) and dimethyl sulfide (0.72 mL, 8 mmol) in dry acetonitrile (10 ml) at 0° C. Stirring was continued for 2.5 hours at 0° C. Progress of the reaction was monitored by silica gel TLC in toluene: acetone (2:1, v/v) solvent system (R$_{f\ tax}$=0.38, R$_{f\ prod}$=0.64), and when formation of higher mobility products was observed the reaction was quenched by evaporation of solvents using Rotavapor at 30° C. A TLC analysis of the reaction mixture indicated the presence of some quantities of unreacted paclitaxel and 2',7-O-bis(methylthiomethyl) paclitaxel. Separation of the title compound from the reaction mixture was achieved by flash column chromatography on Silica Gel 60 (40–63 µm) EM Science (100 mL), column diameter: 2 in. using ethyl acetate:hexane (1:1, v/v) solvent system (R$_{f\ prod}$=0.34). The product (552 mg, 60% yield) was recovered from fractions 12 to 18 (each fraction ca. 20 ml).

MS (FAB/matrix NOBA, NaI, KI): [M+H]$^+$, m/z 914; [M+Na]$^+$, m/z 936; [M+K]$^+$, m/z 952

Elemental Analysis: C: 64.28 (calc. 64.39), H: 5.85 (calc. 6.07), N: 1.46 (calc. 1.53)

UV (MeOH): λmax=226 nm, E(1%/1 cm)=150, A=0.2653

IR (KBr): 3432, 3066, 2940, 1726, 1668, 1602, 1582, 1514, 1484, 1452, 1372, 1242, 1178, 1142, 1108, 1068, 1026, 990, 916, 884, 852, 802, 774, 710, 608, 570, 538, 482 cm$^{-1}$.

$^1$H-NMR (CDCl$_3$) δ: 1.15 (3H, s), 1.19 (3H, s), 1.73 (3H, s), 1.79 (H, s), 1.90 (3H, d), 2.09 (3H, S), 2.16 (3H, s), 2.29 (2H, d), 2.35 (3H, s), 2.77 (H, m), 3.70 (H, d), 3.83 (H, d), 4.17 (H, d), 4.26 (H, m, overlaps with H, d), 4.63 (2H, t), 4.77 (H, dd), 4.91 (H, d), 5.65 (H, d), 5.77 (H, dd), 6.16 (H, dd), 6.48 (H, s), 7.07 (H, d), 7.29–7.50 (10H, m), 7.57 (H, m), 7.73 (2H, d), 8.08 (2H, d).

(b) Preparation of 7-O-
dibenzylphosphonooxymethylpaclitaxel

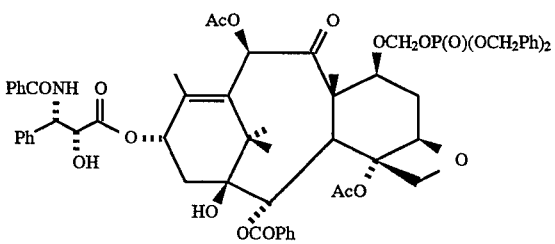

A solution of N-iodosuccinimide (45 mg, 0.2 mM) and dibenzyl phosphate (55 mg, 0.2 mM) in dry tetrahydrofuran (4 mL) was added to a mixture of 7-O-methylthiomethylpaclitaxel (119 mg, 0.13 mM) and powdered molecular sieves 4 Å (ca. 120 mg) in dry 1,2-dichloroethane (5 ml). The reaction mixture was stirred at room temperature for 16 hrs. Progress of the reaction was monitored by TLC in toluene:acetone (2:1, v/v) system ($R_{f\,prod.}$=0.48). Molecular sieves were removed by filtration through Celite 545 and the filtrate was extracted with methylene chloride (100 ml). The organic layer was washed with 1% solution of sodium thiosulfate (ca. 100 ml) and 0.5M sodium bicarbonate (100 ml) and with brine. Extract was filtered through Whatman Phase Separator and solvents were evaporated. Purification on Silica Gel 60 flash column in methylene chloride:ethyl acetate (2:1, v/v) yielded 7-O-dibenzylphosphonooxymethylpaclitaxel (41.5 mg).

(c) Preparation of 7-O-
phosphonooxymethylpaclitaxel and Its Monosodium
Salt

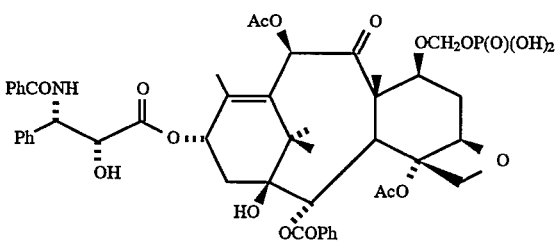

7-O-Dibenzylphosphonooxymethylpaclitaxel (41.5 mg) was dissolved in ethyl acetate (5 ml) and 10% palladium on charcoal (20 mg) was added. Hydrogenation was performed at 40 PSI (275 kPa) at room temperature for 1 hour. Progress of the reaction was monitored by TLC in chloroform:methanol:water (120:45:8, v/v). Purification by preparative TLC (20×20×0.05 cm silica gel plate in the analytical system) gave 7-O-phosphonooxymethylpaclitaxel (26 mg, 75% yield).

Because decomposition of 7-O-dibenzylphosphooxymethylpaclitaxel was observed during silica gel purification, the hydrogenation procedure has been modified. Thus, a crude extract of 7-O-dibenzylphosphonooxymethylpaclitaxel was hydrogenated without any purification. Hydrogenation of the crude extract of 7-O-dibenzylphosphonooxymethylpaclitaxel was performed at 60 PSI (400 kPa) for 24 hrs.

7-O-Phosphonooxymethylpaclitaxel (70 mg) was dissolved in 5 mL of acetone - water (1:1) solution and diluted with water to 50 ml. Dry sodium bicarbonate (18 mg, 1.2 eq.) was added. Acetone was evaporated at room temperature using Rotavapor and the remaining water solution was lyophilized. Crude 7-O-phosphonooxymethylpaclitaxel monosodium salt was purified by C18 reverse phase column chromatography in water:acetonitrile (70:30, v/v) system. Eluate was monitored by analytical HPLC (15 cm, Jones C18 column, 1 mL/min., l=230/270 nm) in acetonitrile: 0.05M ammonium acetate buffer (45:55, v/v), pH=7, Rt=2.09 min. Fractions containing the desired product were combined, acetonitrile evaporated and the remaining aqueous solution lyophilized to provide 7-O-phosphonooxymethylpaclitaxel monosodium salt (112 mg).

MS (FAB): [M+H]$^+$, m/z 986; [M+Na]$^+$, m/z 1008

UV (MeOH): λmax=230 nm, E(1%/1 cm)=248

IR (KBr): 3430, 3066, 2948, 1724, 1652, 1602, 1580, 1518, 1486, 1452, 1372, 1316, 1246, 1178, 1154, 1108, 1070, 1000, 982, 946, 856, 802, 776, 710, 628, 538 cm$^{-1}$.

$^1$H-NMR (acetone-d$_6$/D$_2$O) δ: 8.05 (2H, d), 7.92 (2H, d), 7.65 (1H, dd), 7.58–7.35 (9H, m, overlap), 7.23 (1H, dd), 6.38 (1H, s), 6.08 (1H, t), 5.65 (1H, d), 5.60 (1H, d), 5.10 (1H, br.s), 4.99 (1H, d), 4.97 (1H, br.s), 4.80 (1H, d), 4.28 (1H, dd), 4.11 (2H, s), 3.79 (1H, d), 2.94 (1H, m), 2.35 (3H, s), 2.35–2.10 (1H, m), 2.13 (3H, s), 1.95 (3H, s), 1.84 (1H, m), 1.67 (3H, s), 1.13 (6H, s, overlap).

Example 2

Alternate Method for the Preparation of 7-O-
phosphonooxymethylpaclitaxel (a) Preparation of 2'-O-(benzyloxycarbonyl)
paclitaxel

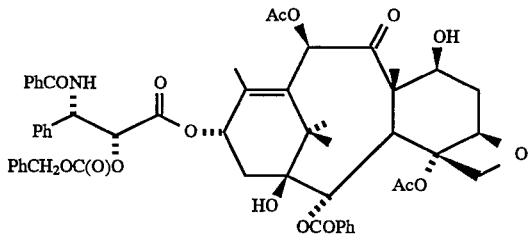

To a stirred solution of paclitaxel (150 mg, 0.176 mmol) and N,N-diisopropylethylamine (93 μL, 0.534 mmol, 3 eq.) in anhydrous methylene chloride (4 mL) at room temperature was added benzyl chloroformate (75 μL, 0.525 mmol, 3 eq.). The reaction mixture was stirred at room temperature for 3 h, concentrated to 2 mL, and purified on a silica gel column, using 1:1 of ethyl acetate/hexanes as eluant, to obtain the title compound as a white powder (150 mg, Y: 86%). MP 140°–150° C. (decomposition).

(b) Preparation of 2'-O-(benzyloxycarbonyl)-7-O-
methylthiomethylpactitaxel

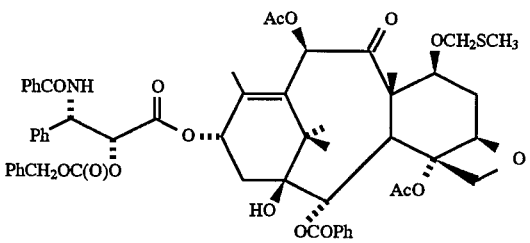

To a cooled (dry ice—CCl$_4$; –30° C. bath temp.) solution of 2'-O-(benzyloxycarbonyl)paclitaxel (4.935 g; 5.0 mmol)

in dry acetonitrile (80 ml) was added in succession dimethylsulfide (3.6 ml; 40 mmol) and benzyol peroxide (4.9 g; 20.247 mmol). After 10 mins. at −30° C., the cold bath was removed and the reaction mixture was stirred vigorously for 2 hr at room temperature. The reaction mixture was then diluted with ethyl acetate to a volume of 200 ml and washed with water and brine. The organic layer was dried (MgSO$_4$), and the solvent was then evaporated to give a residue which was kept under vacuum for 18 h to remove any dimethylsulfoxide that was present as a reaction side product. The residue was purified on a silica gel column using first ethyl acetate: hexane (1:2) as eluant to remove the less polar impurities, followed by ethyl acetate: hexane (1:1) to give the expected title compound as a foam. This was triturated with dry ether and filtered to give the title compound as a fluffy solid (5.0 g, 95%). MP 120°–122° C.

MS (FAB): [MH]$^+$, m/z 1048; [M+Na]$^+$, m/z 1070; [M+K]$^+$, m/z 108

IR (KBr): 3440, 3066, 1750, 1722, 1664, 1602, 1583, 1538 cm$^{-1}$.

NMR (CDCl$_3$) δ: 1.177 (3H, s) 1.236 (3H, s) 1.745 (3H, s) 2.023 (3H, s) 2.121 (3H s) 2.162 (3H, s) 2.436 (3H, s) 3.887 (H, d) 4.134 (H, d) 4.197 (H, d) 4.295 (H, m) 4.964 (H, d) 5.161 (2H, d) 5.450 (H, d) 5.703 (H, d) 5.981 (H, dd) 6.257 (H, t) 6.541 (H, s) 6.920 (H, d, NH) 7.322–8.22 (15H, m).

The title compound was also prepared by the following alternative method:

To a solution of 2'-O-(benzyloxycarbonyl)paclitaxel (2.0 g; 2.0263 mmol) in dry dimethylsulfoxide (10 ml) was added dropwise acetic anhydride (10 ml). The resulting mixture was stirred at room temperature for 18 h under N$_2$, diluted with ethyl acetate (100 ml), and washed carefully with cold 6% sodium bicarbonate solution (6×30 ml), cold water (6×30 ml) and brine. The organic layer was dried (MgSO$_4$), and the solvent was evaporated to give a residue. This was purified by silica gel column and eluted with methylene chloride, methylene chloride-5% acetonitrile, and methylene chloride-10% acetonitrile to give the expected title compound (1.86 g, 87.7%). This compound is identical to that obtained via the previously described dimethyl sulfide/benzoyl peroxide method.

(c) Preparation of 2'-O-(benzyloxycarbonyl)-7-O-dibenzylphosphonooxymethylpaclitaxel

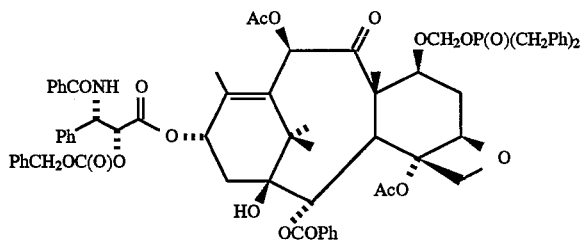

To a solution of 2'-O-(benzyloxycarbonyl)-7-O-methylthiomethylpaclitaxel (5.0 g; 5.5396 mmol) in dry 1,2-dichloroethane (120 ml) was added activated powdered 4 Å molecular sieves (5.0 g). To this mixture was added dropwise at room temperature a solution mixture of N-iodosuccinimide (1.61 g; 7.1632 mmol) and dibenzyl phosphate (1.97 g; 7.1632 mmol) in dry tetrahydrofuran (90 ml). After stirring vigorously at room temperature for 30 min. the reaction mixture was filtered over Celite and the filtrate was evaporated to dryness to give a red residue. The residue was taken up in ethyl acetate (100 ml), washed with cold 6% NaHSO$_3$ solution (2×50 ml), cold 6% NaHCO$_3$ solution (2×50 ml) and brine (1×50 ml). The organic layer was dried (MgSO$_4$) and the solvent was evaporated to give a solid mass which was triturated with dry ether and filtered to give the title compound as an ivory colored solid (5.9 g, 97%). MP 124°–127° C.

MS (FAB): [MH]$^+$, m/z 1278; [M+Na]$^+$, m/z 1301; [M+K]$^+$, m/z 1316

IR (KBr): 3430, 3066, 3032, 1750, 1726, 1664, 1582, 1532 cm$^{-1}$

NMR (CDCl$_3$) δ: 1.160 (3H, s) 1.703 (3H, s) 1.985 (3H, s) 2.164 (3H, s) 2.420 (3H, s) 3.854 (H, d) 4.151 (H, d) 4.216 (H, m) 4.298 (H, d) 4.873 (H, d) 5.043 (6H, m) 5.140 (2H, d) 5.417 (H, d) 5.670 (H, d) 5.971 (H, dd) 6.241 (H, t) 6.317 (H, s) 6.912 (H, d, NH) 7.280–8.115 (25H, m).

(d) Preparation of 7-O-phosphonooxymethylpaclitaxel

To a solution of 2'-O-(benzyloxycarbonyl)-7-O-dibenzylphosphonooxymethylpaclitaxel (6.0 g; 4.7095 mmol) in ethyl acetate (120 ml) was added 10% Pd/C (6.0 g) and the mixture was hydrogenated at 60 psi (400 kPa) for 24 hr. The reaction mixture was filtered over Celite and the solvent was evaporated to give 4.07 g of a crude residue. This was purified on a short silica gel column by successive elution with chloroform: 10%, 20% and 40% methanol to give the title compound as a white solid (3.2 g, 71%) MP 155°–158° C.

This product has the same Rf(TLC) and same retention time (HPLC) as an authentic sample.

MS (FAB): [MH]$^+$, m/z 964; [M+Na]$^+$, m/z 986; [M+K]$^+$, m/z 1002; [M+K$^+$+Na$^+$−H]$^+$, m/z 1024; [M+2K−H]$^+$, m/z 1040

UV (MeOH): λmax=230 nm, E(1%/1 cm)=252.5

IR (KBr): 3432, 3066, 2992, 1722, 1648, 1602, 1580, 1522, 1488, 1452, 1372, 1316, 1246, 1178, 1154,, 1110, 1070, 1000, 980, 946, 854, 802, 776, 710, 628, 538 cm$^{-1}$.

$^1$NMR (acetone-d$_6$/D$_2$O), δ: 1.08 (3H, s), 1.10 (3H, s), 1.63 (3H, s), 1.88 (3H, s), 1.96 (H, m), 2.13 (3H, s), 2.32 (3H, s), 2.89 (H, m), 3.76 (H, d), 4.19 (H, m), 4.89 (H, dd), 5.09 (H, dd), 5.55–5.60 (2H, overlapping d's), 6.04 (H, t), 6.32 (H, s), 720 (H, t), 7.34–7.67 (10H, overlapping m's), 7.87 (2H, dd), 8.02 (2H, dd).

Example 3

2'-O-(ethoxycarbonyl)-7-O-phosphonooxymethylpaclitaxel (a) Preparation of 2'-O-(ethoxycarbonyl)paclitaxel

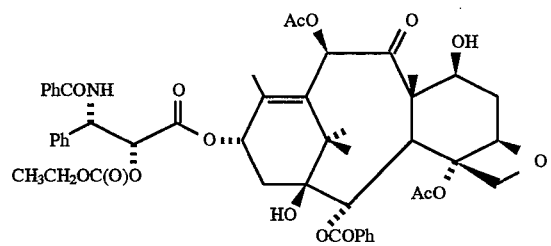

To a solution of paclitaxel (4.35 g, 5.1 mmol) in dry methylene chloride (51 ml) was added N,N-diisopropylethylamine (2.67 ml, 15.3 mmol), followed by ethyl chloroformate (1.46 ml, 15.3 mmol). The reaction mixture was stirred at 0° C. for 2 hrs, and then at room temperature for an additional 1 hr. The reaction mixture was diluted with ethyl acetate (400 ml), the organic phase was washed with saturated solution of NaHCO$_3$ (2×30 ml), and with brine (30 ml). The resulting organic phase was dried over MgSO$_4$ to provide crude title compound (93%) which was used in the next step without further purification.

MS (FAB/NOBA, NaI, KI): [M+H]$^+$, m/z 926; [M+Na]$^+$, m/z 948; [M+K]$^+$, m/z 964

HRMS (FAB/NOBA, CsI/Gly external reference): [M+H]$^+$ m/z 926.3588 observed, C$_{50}$H$_{56}$NO$_{16}$, calculated value: 926.3599 (deviation Δ=1.2 ppm)

$^1$HNMR (CDCl$_3$): δ 1.13 (3H, s), 1.23 (3H, s), 1.30 (3H, t), 1.67 (3H, s), 1.92 (3H, s), 2.21 (3H, s), 2.37 (H, d), 2.45 (3H, s), 2.54 (H, m), 3.80 (H, d), 4.15–4.32 (4H, m's overlapping), 4.43 (H, dd), 4.96 (H, d), 5.42 (H, d), 5.68 (H, d), 5.98 (H, dd), 6.28 (2H, m's, overlapping), 7.00 (H, d), 7.34–7.59 (11H, m's overlapping), 7.74 (2H, d), 8.12 (2H, d).

Alternate Run:

Paclitaxel (5.40 g, 6.324 mmol) in dry dichloromethane (63 mL) was cooled to 0° C. and treated with neat N,N-diisopropylethylamine (3.30 mL, 3 equiv) and then neat ethyl chloroformate (1.81 mL, 3 equiv) dropwise over a 5 min period. The reaction was monitored by TLC (50% ethyl acetate in hexane). After 2 h at 0° C. and 16 h at room temperature, the reaction was complete and the yellow-orange solution was diluted with ethyl acetate (300 mL) and washed with saturated sodium bicarbonate (3×75 mL) and brine (75 mL). Drying (MgSO$_4$) and evaporation afforded crude title compound, which was purified by precipitation: dichloromethane (ca. 100 mL) was added followed by cooling and addition of hexane (ca 60 mL) to the cloud point. After cooling in ice for several hours, the solid was collected by filtration. Yield 5.17 g (88%).

Alternate Run:

In a flame dried, single necked 3 L flask was dissolved paclitaxel (99.0 g, 115.9 mmol) in 1,350 mL of dry methylene chloride under the argon atmosphere. The solution was cooled to −10°. N,N-diisopropylethylamine (52.4 g, 405.7 mmol) was added slowly (addn. time ~13 min.), followed by ClCO$_2$Et (31.45 g, 289.8 mmol; addn. time ~15 min.). The resulting mixture was stirred overnight (16 hrs.) at −4° C. The reaction was judged incomplete by TLC. Another charge of N,N-diisopropylethylamine (2.62 g, 20.28 mmol) was added, followed by ClCO$_2$Et (2.20 g, 20.28 mmol) and the stirring was continued for 3 hrs at −4° C. No starting material was detected by TLC. The cold mixture was diluted with ethyl acetate (1.5 L) and transferred to a separatory funnel. It was then washed with 5% KHSO$_4$ (2×500 mL), water (1×500 mL), 5% KHSO$_4$ (1×500 mL), water (1×500 mL), satd. NaHCO$_3$ (2×500 mL) and brine (2×500 mL), dried (MgSO$_4$) and the solvents were removed in vacuo to give 147 g of the crude product. The residue was dissolved in hot methylene chloride (800 mL, bath temp. 42° C.) and hexanes were added dropwise (530 mL) with stirring, while the temperature was maintained. The crystallizing mixture was set aside for 3 hrs. at room temperature and then in the cold room (0° C.) overnight. The heavy white crystals were collected by filtration and washed with hexanes/CH$_2$Cl$_2$ 1:1 (v/v) (2×200 mL). After drying on the suction filter for 1 hr. it was dried in vacuo (~1.0 mmHg) overnight to give 95.7 g (89% yield) of the title compound (homogeneity index as measured by HPLC=98.5%).

(b) Preparation of 2'-O-(ethoxycarbonyl)-7-O-methylthiomethylpacitaxel

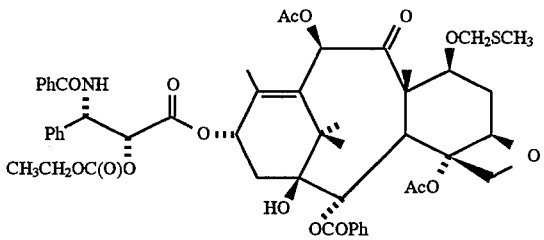

To a solution of 2'-O-(ethoxycarbonyl)paclitaxel (4.38 g, 4.7 mmol) in dry dimethylsulfoxide (12.5 ml) was added acetic anhydride (12.5 ml). The reaction mixture was stirred for 24 hrs at room temperature and then diluted with ethyl acetate (500 ml), washed with saturated solution of NaHCO$_3$ (3×40 ml) and with water (2×40 ml). The resulting organic layer was dried over MgSO$_4$, and the solvents were evaporated in vacuo to dryness. The residue was purified by silica gel chromatography (40% ethyl acetate in hexanes) to afford the desired title compound (4.39 g, 94%).

MS (FAB/NOBA, NaI, KI): [M+H]$^+$, m/z 986; [M+Na]$^+$, m/z 1008; [M+K]$^+$, m/z 1024

HRMS (FAB/NOBA, CsI/Gly external reference): [M+H]$^+$ m/z 986.3646 (calculated value: 986.3633, deviation Δ=1.3 ppm)

$^1$HNMR (CDCl3) δ: 1.18 (3H, s), 1.20 (3H, s), 1.30 (3H, s), 1.75 (3H, s), 1.84 (H, m), 2.09 (3H, s), 2.11 (3H, s), 2.16 (3H, s), 2.24 (H, d), 2.37 (H, d), 2.45 (3H, s), 2.80 (H, m), 3.68 (H, d), 4.08–4.33 (5H, m, overlapping), 4.65 (2H, s), 4.96 (H, d), 5.43 (H, d), 5.69 (H, d), 5.98 (H, dd), 6.26 (H, t), 6.55 (H, s), 7.00 (H, d), 7.32–7.61 (11H, m, overlapping), 7.73 (2H, dd), 8.11 (2H, dd).

Alternate Run:

2'-O-(Ethoxycarbonyl)paclitaxel (2.260 g, 2.4406 mmol) was dissolved in anhydrous dimethylsulfoxide (6 mL), and acetic anhydride (6 mL) was added in one lot at room temperature. The reaction was monitored by HPLC (C18 analytical column; 60% acetonitrile–40% 10 mM ammoniumphosphate buffer, pH 6). After 30 h, the solution was diluted with ethyl acetate (250 mL) and washed with saturated aqueous bicarbonate (3 times) then water and brine. After drying over magnesium sulfate and filtration, the crude product was chromatographed on silica (40% ethyl acetate in hexane) to yield the title compound as a white foam (2.030 g, 91%) that was 90% pure by HPLC. A portion was further purified by a second column (5% acetonitrile in dichloromethane) to afford material that was ca. 97% pure by HPLC.

Alternate Method for the Preparation of 2'-O-(ethoxycarbonyl)-7-O-methylthiomethylpaclitaxel 2'-O-(Ethoxycarbonyl)paclitaxel (4.170 g, 4.503 mmol) was dissolved in anhydrous acetonitrile (68 mL) at −40° C., and dimethyl sulfide (3.2 mL, 44.10 mmol) was added, followed by benzoyl peroxide (4.400 g, 18.24 mmol). The mixture was placed in an ice bath and stirred at 0° C., and the course of the reaction was monitored by TLC (40% ethyl acetate in hexane). After 3 h. no starting material was detected, and the solution was worked up by adding ethyl acetate (250 mL) and saturated aqueous sodium bicarbonate (100 mL). The organic phase was further washed with bicarbonate, water, and brine, then dried over magnesium sulfate and filtered. The residue was purified by silica gel flash chromatography (4% acetonitrile in dichloromethane), to yield the title compound as a white foam (2.571 g, 58% yield). The purity of this sample was judged as >97% by HPLC. The NMR spectrum was identical to the one reported above.

Alternate Run for Preparing 2'-O-(ethoxycarbonyl)-7-O-methylthiomethylpaclitaxel 2'-O-(Ethoxycarbonyl)paclitaxel (49.3 g, 53.2 mmol) was placed in a flame dried single necked 1 L flask and dissolved in dry acetonitrile (500 mL) at room temperature. Methyl sulfide (39.1 mL, 0.532 mol) was rapidly added via syringe. The stirred reaction mixture was cooled to −16° C. in an ice/salt bath and solid benzoyl peroxide (51.6 g, 0.213 mol) was added to the mixture in one lot. (Full four equivalents are required for the reaction to proceed to completion.) Stirring was continued for 30 minutes, during which time the temperature rose to −−10° C. The reaction medium remained heterogeneous throughout this period (benzoyl peroxide has not dissolved completely). The cooling bath was changed to ice/water, the temperature was raised to 0° C. and the remaining benzoyl peroxide dissolved ~5 min. after the warm-up. The reaction was judged complete by TLC after stirring at 0° C. for another 2.5 hours. The volume of the solution was reduced ~200 mL by removing the solvent on a rotovap and it was then transferred to a separatory funnel where it was washed with heptane (5×500 mL). The acetonitrile layer was diluted with ethyl acetate (1.5 L) and washed with a 3:1 mixture satd. $NaHCO_3$/5% $K_2CO_3$ (v/v) (2×500 mL), satd. $NaHCO_3$ (2×500 mL), half-satd. brine (1×500 mL) and brine (1×500 mL), dried ($MgSO_4$) and the solvents were removed in vacuo to give 67.0 g of the crude product. It was dissolved in acetone (200 mL), warmed to 40° C. in a water bath and hexanes were added dropwise with stirring until the cloudiness was observed (400 mL). The crystallizing mixture was set aside for 3 hrs. at room temperature and then transferred to a cold room (0° C.) where it was kept overnight (16 hrs.). A thick cake was formed. The solid was collected by filtration and washed with hexanes/acetone 3:1 (v/v) (2×50 mL). The resulting white crystals were dried on the suction filter for 1 hr. and then in vacuo (~0.5 mmHg) overnight to give 47.5 g (91% yield) of the title compound (homogeneity index as measured by HPLC=94.8%).

(c) Preparation of 2'-O-(ethoxycarbonyl)-7-O-dibenzylphosphonooxymethylpaclitaxel A solution of N-iodosuccinimide (1.953 g, 8.65 mmol) and dibenzyl phosphate (2.41 g, 8.65 mmol) in tetrahydrofuran was added to a mixture of 2'-O-(ethoxycarbonyl)-7-O-methylthiomethylpaclitaxel (5.677 g, 5.76 mmol) and 4 Å molecular sieves (5.7 g) in methylene chloride (100 ml) at room temperature. The reaction mixture was stirred for 40 min. at room temperature. After this period the reaction was complete as judged by TLC. The reaction mixture was filtered through Celite and the filtrate was concenterated in vacuo to give a brownish residue which was diluted with ethyl acetate (800 ml), the organic phase was washed with 1% $Na_2SO_3$ (2×80 ml), then washed with 5% brine (2×50 ml). The organic phase was concentrated in vacuo and dried. Chromatography of the resulting residue (50–60% ethyl acetate in hexanes) gave the desired title compound (6.23 g, 89%).

MS (FAB/NOBA, NaI, KI): $[M+Na]^+$, m/z 1238; $[M+K]^+$, m/z 1254

HRMS (FAB/NOBA, CsI/Gly external reference): $[M+Na]^+$ m/z 1216.4291 ($C_{65}H_{71}NO_{20}P$ calculated value: 1216.4307; deviation Δ=1.3 ppm)

$^1$HNMR (CDCl$_3$), δ: 1.18 (3H, s), 1.21 (3H, s), 1.30 (3H, t), 1.67 (6H, s), 1.80 (H, s), 1.93 (H, m), 1.99 (3H, d), 2.18 (3H, s), 2.23 (H, m), 2.38 (H, m), 2.45 (3H, s), 2.80 (H, m), 3.86 (H, d), 4.14–4.32 (5H, m's, overlapping), 4.88 (H, d), 5.00–5.07 (4H, m's, overlapping), 5.42 (H, d), 5.68 (H, d), 5.96 (H, dd), 6.26 (H, t), 6.33 (H, s), 6.95 (H, d), 7.30–7.61 (11H, m's overlapping), 7.75 (2H, dd), 8.12 (2H, dd).

Alternate Run:

To a solution of 2'-O-(ethoxycarbonyl)-7-O-methylthiomethylpaclitaxel (350 mg, 0.355 mmol) in anhydrous tetrahydrofuran (8 mL) was added a solution of N-iodosuccinimide (120 mg, 0.532 mmol) and dibenzyl phosphate (148 mg, 0.532 mmol) in tetrahydrofuran (5 mL). The reaction was monitored by HPLC (C18 column; 70% acetonitrile, 30% 10 mM ammonium phosphate, pH 6). After 2h, less than 5% starting material was detected, and the reaction was worked-up. The solution was diluted with ethyl acetate (75 mL), and washed with 1% aqueous sodium bisulfite (2×50 mL) and brine (50 mL). After quick drying over magnesium sulfate and filtration, the solvent was evaporated. Silica gel flash chromatography (45% ethyl acetate/hexane) provided the title compound as a white foam (281 mg, 65%). HPLC analysis indicated a purity of ca. 95%.

Alternte Run:

Crushed 4 Å molecular sieves were placed in a flame dried one-necked 1 L flask which was then connected to a vacuum line (~0.5 mmHg). The sieves were heated with a heatgun for ~10 min. while being shaken manually. After cooling under vacuum argon was introduced into the flask and 2'-O-(ethoxycarbonyl)-7-O-methylthiomethylpaclitaxel (37.5 g, 38.03 mmol) was added, followed by dibenzyl phosphate (14.8 g, 53.24 mmol) and THF (400 mL). The

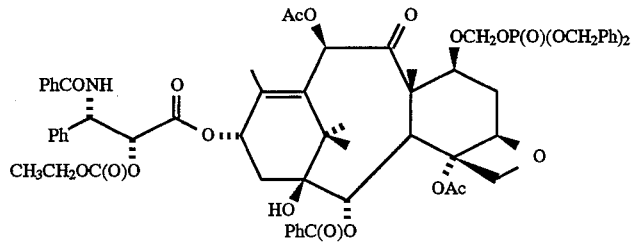

heterogeneous mixture was vigorously stirred for 15 min. at room temperature with a magnetic stirrer. In a separate flame dried flask, N-iodosuccinimide (10.7 g, 47.54 mmol) was dissolved in THF (50 mL) under argon. (During the preparation of the NIS solution, liquid transfer and during the reaction course, the vessels were covered with aluminum foil for protection against light.) It was then added slowly (10 min) to the reaction mixture via a syringe. The flask containing NIS was washed with 5 mL of THF and transferred to the reaction mixture, which was then stirred for 2 hrs. at room temperature. TLC analysis showed absence of the starting material. The deeply red colored solution was filtered through a pad of Celite® directly into a vigorously stirred bi-phasic mixture containing ethyl acetate (500 mL), 10% aq. sodium thiosulfate (300 mL) and satd. sodium bicarbonate (200 mL). The red color disappeared in a few seconds giving a colorless solution. The Celite® pad was washed with EtOAc (~100 mL) and both liquid layers were transferred into a separatory funnel. The organic layer was diluted with 1 L of EtOAc, the layers were separated and the organic layer was washed with a mixture of satd. NaHCO$_3$ and 5% K$_2$CO$_3$ (3:1 v/v, 2×500 mL), then satd. NaHCO$_3$ (2×500 mL), half-saturated brine (1×500 mL) and brine (1×500 mL). The extract was dried with anhydrous MgSO$_4$ and filtered. It was treated with 5.0 g of neutral Norit (charcoal) by stirring at room temperature for 15 min. It was filtered again through a Celite® pad and the solvent was removed under the reduced pressure to give 52 g of the crude product. It was dissolved in toluene/methylene chloride (280 mL/25 mL) and hexanes were added dropwise (20 mL). After being set aside for 3 hrs. at room temperature the crystallizing mixture was left at 0° C. overnight. A pale yellow solid was formed on the flask walls. After decanting the mother liquor, the residue was triturated with toluene (50 mL), filtered, washed with toluene and dried on the suction filter for 30 min. It was then transferred to a desiccator with Drierite® and further dried in vacuo (~0.5 mmHg) for four hours to give 24.4 g (53% yield) of the title compound (homogeneity index as measured by HPLC=95.9%). The mother liquor was evaporated to dryness, triturated with toluene (100 mL), filtered, washed with toluene and dried on the suction filter for 30 min. After drying in a desiccator as described above it gave 12.5 g (27% yield) of the same product (homogeneity index as measured by HPLC=97.1%).

(d) Preparation of 2'-O-(ethoxycarbonyl)-7-O-phosphonooxymethylpaclitaxel; Its Monosodium, Monopotassium, Triethylamine, Arginine, Lysine, Ethanolamine, N-methylglucamine, and Triethanolamine Salts

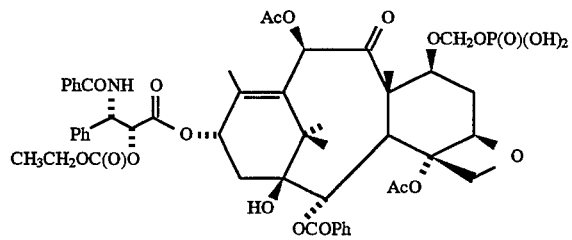

To a solution of 2'-O-(ethoxycarbonyl)-7-O-dibenzylphosphonooxymethylpaclitaxel (1.23 g, 1.01 mmol) in dry ethyl acetate (40 ml) was added 10% Pd on carbon (428 mg, 10%, 0.404 mmol). The reaction mixture was subjected to hydrogenation (60 PSI=400 kPa) with continuous shaking for 24 hrs. The solid was filtered off through Celite, then the Celite was rinsed several times with ethyl acetate. The filtrate was concentrated to give free acid form of the title compound (1.01 g, 80% purity as judged by HPLC). The impurities were removed at the next step by preparative C-18 column chromatography.

MS (FAB/NOBA, NaI, KI): [M+Na]$^+$, m/z 1058; [M+K]$^+$, m/z 1074; [M+2Na−H]$^+$, m/z 1080; [M+Na+K−H]$^+$, m/z 1096; [M+2K−H]$^+$, m/z 1112

HR-MS (FAB/NOBA, CsI/Gly, external reference): [M+Na]$^+$, m/z 1058.3163 (C$_{51}$H$_{58}$NO$_{20}$PNa calculated value: 1058.3188; deviation Δ=2.3 ppm)

$^1$H NMR (acetone-d$_6$/D$_2$O) δ: 1.13 (3H, s), 1.21 (3H, s), 1.66 (3H, s), 1.87 (H, m), 1.93 (3H, s), 2.14 (3H, s), 2.18 (H, m), 2.44 (3H, s), 2.95 (H, m), 3.81 (H, d), 4.12 (2H, s), 4.15–4.27 (3H, m's overlapping), 4.92–4.99 (2H, br.m's overlapping), 5.15 (H, br.s), 5.48 (H, d), 5.61 (H, d), 5.84 (H, dd), 6.07 (H, t), 6.36 (H, s), 7.25 (H, t), 7.28–7.69 (10H, m's overlapping), 7.89 (2H, dd), 8.08 (2H, dd), 8.86 (H, d).

Alternate Run:

2'-O-(Ethoxycarbonyl)-7-O-(dibenzylphosphonooxymethyl)paclitaxel (490 mg, 0.402 mmol) in ethyl acetate (20 mL) was hydrogenated in a Parr shaker at 60 psi (400 kPa) in the presence of palladium on charcoal (10% w/w, 150 mg). Monitoring was carried out by TLC and HPLC. When no more starting material nor an intermediate (presumably the monobenzyl phosphate) were detected (26 h), the suspension was filtered through Celite and evaporated to dryness. HPLC analysis showed a purity of 88–92%.

Alternate Run:

2'-O-(Ethoxycarbonyl)-7-O-phosphonooxymethylpaclitaxel triethylamine salt to be described below (5.4 g, 4.75 mmole) was partitioned vigorously between EtOAc (100 mL) and 5% NaHSO$_4$ (45 ml) with stirring at 0° C. for 30 minutes. The aqueous layer was separated and extracted with EtOAc (20 ml). The combined EtOAc layer was washed with half-brine (25 ml), brine (25 mL×2), dried over NaSO$_4$ and filtered to give a solution of the acid (~4.75 mmole) in EtOAc (~150 mL). This EtOAc solution was then concentrated to dryness on a rotary evaporator to give 3.75 g of the title compound in free acid form in 95% yield. HPLC analysis showed homogeneity index of 96.1%.

The monosodium salt was prepared as follows:

A sample of 2'-O-(ethoxycarbonyl)-7-O-phosphonooxymethylpaclitaxel (1.6 g, 1.55 mmol) was dissolved in acetonitrile (30 ml) by sonication. This solution was diluted with water (30 ml) and 1.1M solution of NaHCO$_3$ (2.11 ml, 2.32 mmol) was added, alternately shaking and sonicating to obtain a solution (5–20 min). The somewhat milky solution was applied onto a C-18 column, washing with two column volumes of water, then eluting the monosodium salt with 25% acetonitrile/water. The appropriate fractions were pooled, the acetonitrile evaporated, and the aqueous phase lyophilized, to yield the monosodium salt of the title compound (850 mg, ca 50%), having HPLC purity of 97%.

MS (FAB/NOBA, NaI, KI): [M+Na]$^+$, m/z 1180

HR - MS (FAB/NOBA, CsI/Gly external reference): [M+Na]$^+$, m/z 1080.2968 (C$_{51}$H$_{57}$NO$_{20}$PNa$_2$ calculated value: 1080.3007; deviation D=3.6 ppm)

Elemental analysis: C: 52.65 (calc. 56.72), H: 5.06 (calc. 5.23), N: 1.20 (calc. 1.30), Na: 2.74 (calc. 2.12)

IR (KBr): 3430, 3066, 2988, 1746, 1722, 1660, 1602, 1582, 1526, 1488, 1452, 1374, 1246, 1178, 1150, 1108, 1070, 1052, 1026, 1002, 966, 912, 834, 792, 776, 710, 628, 538 cm$^{-1}$.

$^1$H-NMR (DMSO-d$_6$, D$_2$O, acetone-d$_6$) δ: 1.10 (6H, s), 1.23 (3H, t), 1.64 (3H, s), 1.70 (H, m), 1.90 (3H, s), 1.99 (H, m), 2.14 (3H, s), 2.37 (3H, s), 2.98 (H, m), 3.74 (H, d), 4.07 (2H, s), 4.13–4.26 (3H, m, overlapping), 4.80 (H, br.dd), 4.97 (H, d), 5.09 (H, br.t), 5.44 (H, d), 5.55 (H, d), 5.99 (H, t), 6.34 (H, s), 7.22 (H,t), 7.43–7.69 (10H, m, overlapping), 7.92 (2H, dd), 8.06 (2H, dd).

The sodium salt can also be prepared as follows:

Crude 2'-O-(ethoxycarbonyl)-7-O-phosphonooxymethylpaclitaxel (89%; 70 mg, 0.060 mmol), in EtOAc (2 ml) was treated with a solution of sodium ethylhexanoate (87.5 mM in EtOAc, 1.0 ml, 0.0875 mmol) at room temperature with stirring. After stirring at room temperature for 1 h, hexane (1.2 ml) was added to the cloud point. After storing at −20° C. for 2 h, the fine amorphous powder was filtered (with some difficulty, very slow) through fine filter paper, to yield 45 mg (70%) of the sodium salt. This was 95.2% pure by HPLC and contained a small amount of ethylhexanoic acid (NMR).

The triethanolamine salt was prepared as follows:

2'-O-(Ethoxycarbonyl)-7-O-phosphonooxymethylpaclitaxel, crude from the hydrogenation (89% by HPLC) (0.69 g, 0.593 mmol after correction for impurities) was dissolved in ethyl acetate (10 ml), and stirred slowly while a solution of triethanolamine (0.11M in EtOAc, used 5.1 ml, 0.95 eq) was added dropwise. The milky solution obtained by this procedure was digested at 0° C. for 2 h, then filtered on file filter paper, rinsing with cold EtOAc. Yield: 499 mg (80%) of an amorphous, fine, non-electrostatic powder that was dried overnight in vacuo. HPLC shows 96.6% purity (C-18, 45% 5 mM $Q_{12}$+10 mM ammonium phosphate pH 6, 55% actonitrile). NMR spectrum ($D_2O$/acetone/DMSO) shows traces of ethyl acetate and no other clearcut impurities. It analyzes for a 2–3× hydrate.

The triethanolamine salt of lesser priority obtained from another experiment was further purified by the following procedure. The triethanolamine salt (approx. 2 g) was dissolved in about 30% acetonitrile/water. This solution was eluted with slight nitrogen pressure through a column of C18 (Bakerbond) with a gradient of 20% to 40% acetonitrile in water. The fractions containing the desired triethanolamine salt were collected; the acetonitrile was removed by rotary evaporation under reduced pressure. The aqueous solutions were frozen and lyophilized overnight to afford 1.4 grams of the triethanolamine salt with a purity of 97.5%.

The triethanolamine salt can also be prepared as follows:

2'-O-(Ethoxycarbonyl)-7-O-phosphonooxymethylpaclitaxel triethylamine salt (3.0 g, 2.64 mmole) was partitioned between EtOAc (60 ml) and 5% $NaHSO_4$ (30 ml) with vigorous stirring at 0° C. for 15 minutes. The aqueous layer was separated and extracted with EtOAc (10 mL). The combined EtOAc layer was washed with brine (15 ml), dried over $Na_2SO_4$, filtered to give a solution of the acid (~2.64 mmole) in EtOAc (~70 ml). To this EtOAc solution at room temperature was added dropwise with vigorous stirring $N(CH_2CH_2OH)_3$ (0.35 ml, 2.64 mmole) over a period of 5 minutes. The resulting suspension was stirred for an additional 1 hr and then it was filtered, washed with EtOAc (15 ml×2), dried in vacuo to give 2.8 g of the triethanolamine salt in 89% yield. HPLC analysis showed homogeneity index of 98.7%; mp.: >157° C. with decomposition.

Elemental analysis calculated for $C_{56}H_{73}N_2O_{23}P.2.0$ $H_2O.0.3$ EtOAc: C, 55.60; H, 6.48; N, 2.27; KF ($H_2O$), 2.92. Found: 55.94; H, 6.59; N, 2.43; KF ($H_2O$), 3.50.

The triethylamine salt was prepared as follows:

To the solution of 2'-O-(ethoxycarbonyl)-7-O-dibenzylphosphonooxymethylpaclitaxel (10 g, 8.23 mmole), in EtOAc (350 ml), at room temperature was added 10% Pd on carbon (2 g, 20% load). The resulting suspension was degassed by evacuating air and then purging with argon. This process was repeated two additional times. The argon then was replaced with hydrogen following the same degassing procedure. The resulting suspension was stirred under a balloon hydrogen pressure (2–3 pound per square inch) for 16 hr at room temperature with vigorous stirring. The hydrogen was evacuated and replaced with argon three times following the degassing procedure. The resulting suspension was filtered through a pad of Celite. To this homogeneous filtrate was slowly added $Et_3N$ (8.23 mmole, 1.14 mL) over a period of 5 min with vigorous stirring. The resulting fine white suspension was stirred for an additional 30 min. It was filtered through a fritted funnel. The filter cake was dried in vacuo (1 mmHg) for 16 hr to give 8.22 g of the title triethylamine salt in 88% yield. HPLC analysis showed homogeneity index of 97.4%; mp.: >178° C. with decomposition.

Elemental analysis calculated for $C_{57}H_{73}N_2O_{20}P.4.5$ $H_2O$: C, 56.19; H, 6.79; N, 2.30; KF ($H_2O$), 6.65. Found: 56.33; H, 6.87; N, 2.32; KF ($H_2O$), 7.96.

Alternate run for making the triethylamine salt:

2'-O-(Ethoxycarbonyl)-7-O-dibenzylphosphonooxymethylpaclitaxel (5.67 g, 4.66 mmol) was added to a 250 mL flask and dissolved in ethyl acetate (150 mL). The flask was equipped with a three-way valve with one connection to house vacuum and one connection to an argon line. Using the valve, the flask was partially evacuated and then purged with argon. This process was repeated two additional times. Palladium on activated carbon (10% Pd) (0.85 g) was added to the flask. The argon line attached to the three-way valve was replaced with a hydrogen-filled balloon. Using the valve, the flask was partially evacuated and then purged with hydrogen. This process was repeated four additional times. The resulting mixture was stirred at room temperature under the hydrogen balloon atmosphere overnight. TLC analysis 17 hours after the initial exposure to hydrogen showed the starting material to be absent. The hydrogen balloon attached to the three-way valve was replaced with an argon line. Using the valve, the flask was partially evacuated and then purged with argon. This process was repeated two additional times. The contents of the flask were vacuum-filtered through a pad of Celite. The Celite was rinsed with ethyl acetate (2×10 mL). To the stirring filtrate was added $NEt_3$ (0.650 mL, 4.66 mmol). The resulting suspension was stirred at room temperature for two hours, and the volume was then reduced to ~150 mL via a rotovap. The solid was filtered, washed with ethyl acetate (2×10 mL) and dried under vacuum to give 4.76 g (90% yield) of the title triethylamine salt as a white powder (homogeneity index of the product was determined to be 96.6% by HPLC analysis).

Alternate run for making the triethylamine salt:

2'-O-(Ethoxycarbonyl)-7-O-dibenzylphosphonooxymethylpaclitaxel (5.17 g, 4.25 mmol) was added to a 250 mL flask and dissolved in ethyl acetate (150 mL). The flask was equipped with a three-way valve with one connection to house vacuum and one connection to an argon line. Using the valve, the flask was partially evacuated and then purged with argon. This process was repeated two additional times. Palladium on activated carbon (10% Pd) (0.86 g) was added to the flask. The argon line attached to the three-way valve was replaced with a hydrogen-filled balloon. Using the valve, the flask was partially evacuated and then purged with hydrogen. This process was repeated five additional times. The resulting mixture was stirred at room temperature under the hydrogen balloon atmosphere overnight. TLC analysis 16 hours after the initial exposure to hydrogen showed the starting material to be absent. The hydrogen balloon attached to the three-way valve was replaced with an argon line. Using the valve, the flask was partially evacuated and then purged with argon.

This process was repeated two additional times. The contents of the flask were vacuum-filtered through a pad of Celite. The Celite was rinsed with ethyl acetate (4×10 mL). To the stirring filtrate was added NEt₃ (0.590 mL, 4.25 mmol). The resulting suspension was stirred at room temperature for one hour, and the volume was then reduced to ~140 mL via a rotovap. The solid was filtered, washed with ethyl acetate (10 mL) and dried under vacuum to give 4.46 g (92% yield) of the title triethylamine salt as a white powder (homogeneity index as determined by HPLC analysis was 96.7%).

The lysine salt was prepared as follows:

2'-O-(ethoxycarbonyl)-7-O-dibenzylphosphonooxymethylpaclitaxel (15.0 g, 12.34 mmole) was added portionwise to a suspension of 10% palladium on carbon (20% load, 3 g) in EtOH (600 ml, 200 proof) at 0° C. The resulting suspension was degassed by evacuating air and purging with argon. This process was repeated two additional times. The argon then was replaced with hydrogen following the same degassing procedure with vigorous stirring. The resulting mixture was stirred at 0° C. for 2 hrs. The cooling bath was removed and the reaction solution was stirred at ambient temperature for additional 4½ hrs. The reaction mixture was degassed by evacuating hydrogen and purging with argon three times. It was filtered under argon through a pad of Celite. To the resulting filtrate was slowly added a solution of lysine (1.63 g, 0.94 eq) in a 1:1 mixture of $H_2O$:EtOH (200 proof) (20 ml) over a period of 5 minutes with vigorous stirring. To the resulting white suspension was added distilled water (110 ml) and stirred for 30 minutes. It was warmed to about 55° C. The resulting homogeneous solution was kept in an oil bath set at 50° C. and slowly cooled down to room temperature for 16 hrs and 4° C. for 3 hrs. It was filtered and suction dried for 16 hrs to give 11.8 g (~80% yield) of the lysine salt with homogeneity index of 99.0% as determined by HPLC; mp.: >170° C. with decomposition.

Elemental analysis calculated for $C_{57}H_{72}N_3O_{22}P.8.0$ $H_2O$: C, 51.62; H, 6.69; N, 3.17; KF ($H_2O$), 10.87. Found: 51.76; H, 6.57; N, 3.48; KF ($H_2O$), 11.42.

The ethanolamine salt was prepared as follows:

2'-O-(Ethoxycarbonyl)-7-O-phosphonooxymethylpaclitaxel triethylamine salt (3.0 g, 2.64 mmole) was partitioned between EtOAc (60 ml) and 5% NaHSO₄ (30 ml) with vigorous stirring at 0° C. for 15 minutes. The aqueous layer was separated and extracted with EtOAc (15 ml). The combined EtOAc layer was washed with brine (15 ml), dried over Na₂SO₄, filtered to give a solution of the free acid (~2.64 mmole) in EtOAc (~70 ml). To this EtOAc solution at room temperature was added dropwise with vigorous stirring a solution of H₂NCH₂CH₂OH (0.15 ml, 2.64 mmole) in EtOAc (5 mL) over a period of 5 minutes. The resulting suspension was stirred for an additional 1 hr and then it was filtered, washed with EtOAc (15 ml×2), and dried in vacuo to give 2.6 g of the title ethanolamine salt in 89% yield. HPLC analysis showed homogeneity index of 97.8%; mp.: >130° C. with decomposition.

Elemental analysis calculated for $C_{53}H_{65}N_2O_{21}P.2.5$ $H_2O$: C, 55.73; H, 6.18; N, 2.45; KF ($H_2O$), 3.94. Found: C, 55.76; H, 6.39; N, 2.45; KF ($H_2O$), 6.00.

The arginine salt was prepared as follows:

2'-O-(Ethoxycarbonyl)-7-O-dibenzylphosphonooxymethylpaclitaxel (30.0 g, 24.69 mmole) was added portionwise to a suspension of 10% palladium on carbon (20%, load, 6 g) in EtOH (900 ml, 200 proof) at 0° C. The resulting suspension was degassed by evacuating air and purging with argon. This process was repeated two additional times. The argon then was replaced with hydrogen following the above degassing procedure with vigorous stirring. The resulting mixture was stirred at 0° C. for 2 hrs. The cooling bath was removed and the reaction solution was stirred at ambient temperature for additional 24 hrs. The reaction mixture was degassed by evacuating hydrogen and purging with argon three times following the above degassing procedure. It was filtered under argon through a pad of Celite. The filtrate was divided into two equal portions and EtOH (190 ml, 200 proof) was added to each portion. To one portion (~630 ml) was slowly added a solution of arginine (2.0 g, 0.94 eq) in a 2:1 mixture of $H_2O$:EtOH (200 proof) (20 ml) over a period of 5 minutes with vigorous stirring. To the resulting white suspension was added distilled water (100 ml) and stirred for 30 minutes and then warmed to about 60° C. It was filtered hot and the filtrate was kept in an oil bath set at 50° C., allowed to cool down to room temperature and kept at room temperature for 2 hrs and at 4° C. for 2 hrs. It was filtered and washed with cold 3% $H_2O$ in EtOH (100 ml) and suction dried for 16 hrs to give 12.95 g (~86% yield) of the title arginine salt with homogeneity index of 96.7%.

This material (12.95 g) was dissolved in a mixture of 15% $H_2O$ in EtOH (~700 ml) at 55° C. The solution was cooled down and kept at 30° C. for 3½ hrs, room temperature for 16 hrs, and 4° C. for 3 hrs. The resulting crystals were filtered, washed with cold 2% $H_2O$ in EtOH (50 ml×2), suction dried for 4 hrs, and then dried in vacuo (1 mmHg) for 16 hrs to give 10.2 gs (~80% yield) of the title arginine salt (homogeneity index was 98.5%); mp.: >176° C. with decomposition.

Elemental analysis calculated for $C_{57}H_{72}N_5O_{22}P.6.4$ $H_2O$: C, 51.65; H, 6.45; N, 5.28; KF ($H_2O$), 8.7. Found: C, 51.86; H, 6.65; N,5.53; KF ($H_2O$), 8.72.

The N-methylglucamine salt was prepared as follows:

2'-O-(Ethoxycarbonyl)-7-O-dibenzylphosphonooxymethylpaclitaxel (30.0 g, 24.69 mmole) was added portionwise to a suspension of 10% palladium on carbon (20% load, 6 g) in EtOH (900 ml, 200 proof) at 0° C. The resulting suspension was degassed by evacuating air and purging with argon. This process was repeated two additional times. The argon then was replaced with hydrogen following the above degassing procedure with vigorous stirring. The resulting mixture was stirred at 0° C. for 2 hrs. The cooling bath was removed and the reaction solution was stirred at ambient temperature for additional 24 hrs. The reaction mixture was degassed by evacuating hydrogen and purging with argon three times following the above degassing procedure. It was filtered under argon through a pad of Celite. The filtrate was divided into two equal portions and EtOH (190 ml, 200 proof) was added to each portion. To one portion (~630 ml) was slowly added a solution of N-methylglucamine (2.24 g, 0.94 eq) in a 1:1 mixture of $H_2O$:EtOH (200 proof) (20 ml) over a period of 5 minutes with vigorous stirring. To the resulting white suspension was added distilled water (100 ml) and the suspension was stirred for 30 minutes and then warmed to about 49° C. The clear homogeneous solution was kept in an oil bath set at 50° C., allowed to cool down to room temperature and kept at room temperature for 2 hrs and at 4° C. for 1½ hrs. It was filtered and washed with 3% $H_2O$ in EtOH (100 ml), suction dried at room temperature for 16 hrs to give 9.65 g (~64% yield) of the title N-methylglucamine salt with homogeneity index of 96.4%.

This material (9.65 g) was dissolved in a mixture of 15% $H_2O$ in EtOH (~450 ml) at 52° C. Then, the solution was cooled down and kept at 28° C. for 3½ hrs, room temperature for 16 hrs, and 4° C. for 3 hrs. The resulting crystals were filtered, washed with cold 2% $H_2O$ in EtOH (50 ml×2), suction dried for 4 hrs; and then dried in vacuo (1 mmHg) for 16 hrs to give 7.5 g (~80% yield) of the title N-methylglucamine salt (homogeneity idex as determined by HPLC was 98.6%); mp.: >154° C. with decomposition.

Elemental analysis calculated for $C_{58}H_{75}N_2O_{25}P.5.0$ $H_2O$: C, 52.72; H, 6.48; N, 2.12; KF ($H_2O$), 6.82. Found: C, 53.09; H, 6.50; N, 2.08; KF ($H_2O$), 7.12.

Example 4

2'-O-(Phosphonooxymethyl)paclitaxel (a) Preparation of 2'-O-(methylthiomethyl)-7-O-(triethylsilyl)paclitaxel

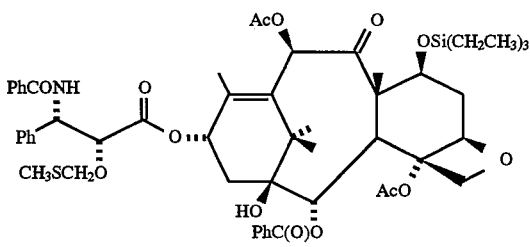

To a cooled (0° to −5° C.) solution of 7-O-(triethylsily) paclitaxel (2.46 g; 2.5439 mmol) in dry acetonitrile (100 ml) was added dimethylsulfide (1.348 g; 1.59 ml; 21.6976 mmol) followed by benzoyl peroxide (2.628 g; 10.8488 mmol). The heterogeneous mixture was stirred at 0° C. for 1 h and kept at 5° C. for 18 h. A yellow solution was observed. This was evaporated to dryness and purified by silica gel column (eluting with ethyl acetate: hexane, 1:4; 1:3 and 1:2) to give the title compound (1.0 g, 38%). This was used as such for next step.

MS: $[M+H]^+$, 1028; $[M+Na]^+$, 1050; $[M+K]^+$, 1066

(b) Preparation of 2'-O-(methylthiomethyl)paclitaxel

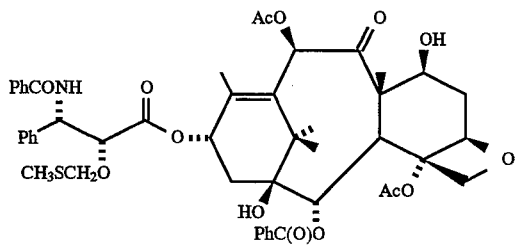

To a cooled (~15° C.) solution of the product of step (a) (1.0 g; 0.9737 mmol) in dry acetonitrile (30 ml) was added dropwise 0.5N HCl (3 ml). The resulting solution was stirred at −15° C. for 1 h and at 5° C. for 18 h. This was diluted with ethyl acetate (20 ml) and washed with cold 6% $NaHCO_3$ solution and brine. It was dried ($MgSO_4$) and evaporated to dryness. This was purified by silica gel plate (methylene chloride: 15% acetonitrile) to give pure title compound (280 mg, 31.4%).

IR (KBr): 3446, 3064, 2940, 1726, 1666, 1582, 1516, 1486.

NMR ($CDCl_3$): δ1.118 (s, 3H), 1.229 (s, 3H), 1.662 (s, 3H), 1.689 (s, 3H), 1.871 (s, 3H), 2.209 (s, 3H), 2.450 (s, 3H), 3.800 (d, H), 4.119 (d, H), 4.305 (d, H), 4.413 (m, H), 4.563 (d, H), 4.703 (d, H), 4.940 (d, H), 4.958 (dd, H), 5.667 (d, H), 5.822 (dd, H), 6.263 (m, 2H), 7.019 (d, NH), 7.293–8.127 (m, 15H).

MS: $[M+H]^+$, 914; $[M+Na]^+$, 936; $[M+K]^+$, 952

HRMS: $MH^+$: 914.3394 (calculated=914.3422).

(c) Preparation of 2'-O-(dibenzylphosphonooxymethyl)paclitaxel

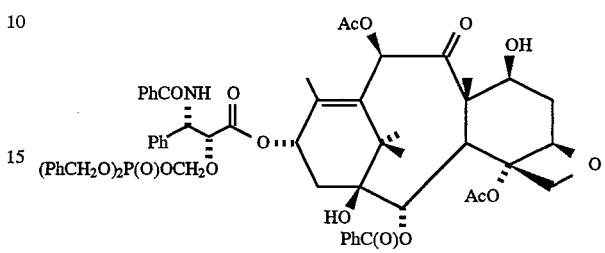

To a stirred solution of the product of step (b) (0.89 g; 0.9748 mmol) in dry 1,2-dichloroethane (12 ml) was added powdered 4A molecular sieves (1.0 g) followed by dropwise addition of a solution mixture of N-iodosuccinimide (0.33 g; 1.4622 mmol) and dibenzyl phosphate (0.41 g; 1.4622 mmol) in dry tetrahydrofuran (8 ml). The resulting mixture was stirred at room temperature for 1 h., then filtered over Celite. The filtrate was evaporated to dryness and the red residue was taken up in ethyl acetate (50 ml) and washed with cold 6% $NaHSO_3$, cold 6% $NaHCO_3$ and brine. It was dried ($MgSO_4$) and evaporated to give a foam. This was purified by silica gel plate (methylene chloride:20% acetonitrile) to give pure product (0.77 g, 69%).

IR (KBr): 3854, 3744, 3362, 3066, 1960, 1722, 1602, 1580.

NMR ($CDCl_3$): δ1.075 (s, 3H), 1.167 (s, 3H), 1.651 (s, 3H), 1.799 (s, 3H), 2.209 (s, 3H), 2.296 (s, 3H), 2.464 (m, H), 3.686 (d, H), 4.121 (d, H), 4.240 (d, H), 4.293 (m, H), 4.808–4.957, (m, 6H), 5.006 (m, H), 5.565–5.649 (m, 2H), 6.034 (t, H), 6.194 (3, H), 7.100–8.132, (m, 26H).

MS: $[M+H]^+$, 1144; $[M+Na]^+$, 1166; $[M+K]^+$, 1182

(d) Preparation of 2'-O-(phosphonooxymethyl) paclitaxel

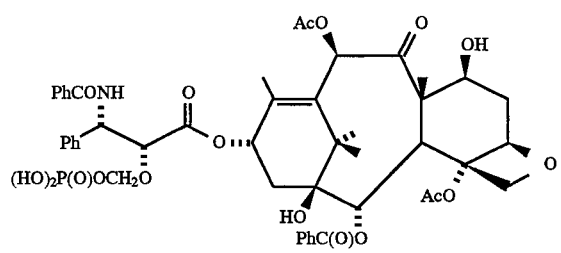

A mixture of the product of step (c) (0.9 g; 0.7874 mmol) and 10% Pd/C (1.0 g) in ethyl acetate (20 ml) was hydrogenated at 60 psi (400 kPa) for 24 h. The reaction mixture was filtered over Celite and the filtrate evaporated to dryness. The residue was purified by silica gel plate (methylene chloride: 40% methanol) to give the title product (0.254 g, 33.4%). MP 202°–205° C. (d).

IR (KBr): 3438, 3066, 2942, 1722, 1652, 1602 $cm^{-1}$.

NMR (acetone-$d_6$/$D_2O$): δ1.081 (s, 6H), 1.571 (s, 3H), 1.847 (s, 3H), 2.115 (s, 3H), 2.357 (s, 3H), 3.707 (d, H), 4.08 (m, 2H), 4.275 (m, H), 4.941–5.085 (m, 4H), 5.231 (t, H), 5.430 (d, H), 5.544 (d, H), 5.970 (t, H), 6.376 (s, H), 6.961–8.017 (m, 16H).

MS: [M+Na]+, 986; [M+K]+, 1002; [M+2Na-H]+, 1008; [M+Na+K-H]+, 1024; [M+2K-H]+, 1040

(b) Preparation of 2',7-O-bis (dibenzylphosphonooxymethyl)paclitaxel

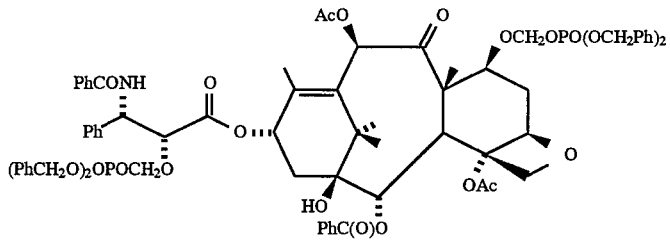

HRMS: MNa+, 986.2955 (Calculated=986.2976).

Example 5

2',7-O-bis(phosphonooxymethyl)paclitaxel sodium salt (a) Preparation of 2',7-O-bis(methylthiomethyl) paclitaxel

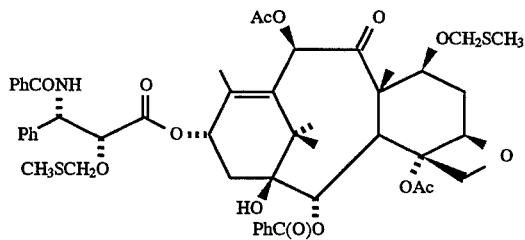

Solid benzoyl peroxide (1.995 g, 8 mmol) was added to a stirred solution of paclitaxel (0.853 g, 1 mmol) and dimethyl sulfide (1.465 g, 20 mmol) acetonitrile (20 mL) at 0° C. The reaction mixture was stirred vigorously at 0° C. for 3 hours. Its progress was monitored by TLC in hexane:ethyl acetate (1:1, v/v), $R_{f\ paclitaxel}$=0.24, $R_{f\ product}$=0.60. When starting material disappeared (ca. after 3 hrs) the reaction was quenched by evaporation of solvents to dryness at 25° C. using house vacuum. The dry residue was separated using silica gel column (EM Science, 40–63 µm), 100 mL of dry silica gel, column size: Φ=¾ in., solvent system: hexane-:ethyl acetate (3:2, v/v), volume of each fraction: ca. 25 mL. The title compound (0.515 g, 53% yield) was recovered from fractions 15 to 19.

MS (FAB/matrix NOBA,NaI KI): [M+H]+, m/z 974; [M+Na]+, m/z 996; [M+K]+, m/z 1012

UV (MeOH): λmax=204 nm, E(1%/1 cm)=243.45; λmax=28 nm, E(1%/1 cm)=313.99

IR (KBr): 3440, 3064, 2926, 1724, 1668, 1602, 1582, 1514, 1484, 1452, 1372, 1314, 1266, 1242, 1178, 1142, 1068, 1026, 990, 916, 886, 848, 800, 774, 710, 646, 606, 570, 540, 480 cm⁻¹.

$^1$H-NMR (CDCl₃) δ: 1.17 (3H, s), 1.20 (3H, s), 1.68 (3H, s), 1.74 (3H, s), 1.84 (H, dd), 2.04 (3H, d), 2.09 (3H, s), 2.15 (3H, s) overlaps with (H, m), 2.37 (H, dd), 2.51 (3H, s), 2.79 (H, ddd), 3.78 (H, d), 4.18 (H, d), 4.28 (H, m), 4.31 (H, d), 4.53–4.74 (4H, two overlapping AB m), 4.93 (H,d), 4.95 (H, d), 5.68 (H, d), 5.82 (H, dd), 6.24 (H, dd), 6.54 (H, s), 7.05 (H, d), 7.28–7.59 (10H, overlapping m), 7.57 (H, m), 7.76 (2H, d), 8.09 (2H, d).

A solution of N-iodosuccinimide, (135 mg, 0.5 mmol) and dibenzylphosphate, (167 mg, 0.5 mmol) in dry tetrahydrofuran (8 mL) was added to a mixture of 2',7-O-bis (methylthiomethyl)paclitaxel (198 mg, 0.2 mmol) and 5 Å molecular sieves (ca. 200 mg) in methylene chloride (12 mL) at room temperature. The reaction mixture was stirred for 1.5 hours, then the molecular sieves were filtered off on celite, washed with methylene chloride (10 mL) and the solvents were evaporated to dryness at room temperature using house vacuum. The residue was dissolved in ethyl acetate (100 ml) and washed in a separation funnel with 1% sodium thiosulfate (50 mL), with 0.5m sodium bicarbonate (50 mL), and twice with water (2×50 mL). The organic phase was dried over magnesium sulfate, evaporated to dryness and re-dissolved in ethyl acetate (1 mL). The product was precipitated with 50 mL of ethyl ether: hexane (1:1) and washed twice with the same solvent system (2×50 mL). A crude product (218 mg) was obtained in 74% yield. Purification of this product was performed by loading its methylene chloride solution (3 mL) on silica gel (=101 =¾ in.×L=1 in.) and eluting the product with 50 mL of methylene chloride:ethyl acetate (3:1) solvent system. The title compound (172.7 mg) was obtained in 59.3% yield.

MS (FAB, matrix NOBA/NaI, KI): [M+Na]+, m/z 1456; [M+K]+, m/z 1472

UV (MeCN): λmax=194 nm, E(1%/1 cm)=1078.36; λmax=228 nm, E(1%/1 cm)=311.95

IR (KBr): 3430, 3066, 3032, 2958, 1744, 1726, 1664, 1602, 1582, 1532, 1488, 1456, 1372, 1270, 1244, 1158, 1108, 1068, 1016, 1000, 952, 886, 800, 776, 738, 698, 604, 498 cm⁻¹.

$^1$H-NMR (CDCl₃) δ: 1.12 (3H, s), 1.14 (3H, s), 1.56 (H, m), 1.67 (3H, s), 1.84 (3H, d), 1.90 (H, m), 2.17 (3H, s), 2.29 (3H, s), 2.73 (H, m), 3.73 (H, d), 4.08 (H, d), 4.15 (H, m), 4.20 (H, d), 4.77 (H, m), 4.79 (H, d), 4.91–5.04 (10H overlapping m), 5.25 (H, dd), 5.38 (H, dd), 5.54–5.64 (2H, overlapping m), 5.99 (H, br. dd), 6.25 (H, s), 7.11–7.14 (2H, m), 7.24–7.64 (28H, overlapping m), 7.94 (2H, dd), 8.04 (2H, dd), 8.30 (H, d).

(c) Preparation of 2',7-O-bis(phosphonooxymethyl) paclitaxel sodium salt

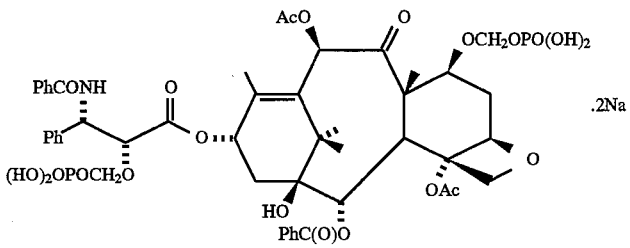

A sample of 2',7-O-bis(dibenzylphosphonooxymethyl) paclitaxel (112 mg, 0.078 mmol) was dissolved in ethyl acetate (7 ml) and hydrogenated over 10% palladium on charcoal (50 mg) at room temperature, 60 PSI (400 kPa), for 2 hours. The catalyst was removed by filtration over Celite. The Celite was rinsed with ethyl acetate (10 mL). The filtrate was treated with solid sodium bicarbonate (20 mg, 3 eq.) and then the solvent was evaporated to dryness. A dry residue was re-dissolved in 5 mL of water: acetone (4:1, v/v) and purified by C-18 reverse phase column chromatography (55–105µ C-18, Waters, 50 mL of dry C-18, Φ=¾ in. in water: acetone (4:1, v/v). Eluant was monitored on analytical HPLC Jones C-18 column (15 cm, 1 mL/min., λ=230 nm) in acetonitrile:phosphate buffer pH 6 (50/50, v/v) with the addition of Q12 ion pair cocktail (Regis), Rt=4.7 min. Fractions containing the title product were combined, acetone was evaporated under house vacuum at 20° C., and the solution was lyophilized. The title product (44.2 was obtained in 58.8% yield.

MS (FAB,matrix NOBA/NaI, KI): [M+H]$^+$, m/z 1118; [M+Na]$^+$, m/z 1140

UV (MeCN): λmax=192 nm, E(1%/1 cm)=129.73; λmax=230 nm, E(1%/1 cm)=26.43

IR (KBr): 3430, 3066, 2956, 1724, 1658, 1604, 1582, 1520, 1486, 1452, 1374, 1316, 1256, 1152, 1110, 1070, 1026, 966, 914, 802, 772, 710, 538 cm$^{-1}$.

$^1$H-NMR (acetone-d$_6$/D$_2$O) δ: 0.97 (3H, s), 1.02 (3H, S), 1.47 (H, m), 1.54 (3H, s), 1.70 (H, m), 1.75 (3H, s), 1.85 (H, m), 2.11 (3H, s), 2.30 (3H, s), 2.88 (H, m), 3.64 (H, d), 4.03 (H, m), 4.06 (H, d), 4.16 (H, d), 4.74 (H, m), 4.86 (H, m), 5.11 (H, br. t), 5.22 (H, d), 5.42 (H, d), 5.90 (H, br. t), 6.21 (H, s), 7.06 (H, br.t), 7.32–7.69 (10H, ovelapping m), 7.80 (2H, d), 7.93 (2H, d).

Example 6

7-O-methylthiomethylbaccatin III (7-MTM baccatin III)

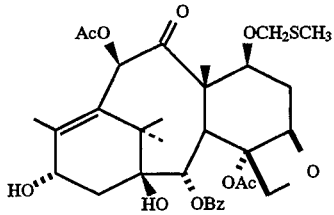

To a solution of 2'-O-ethyloxycarbonyl-7-O-methylthiomethylpaclitaxel (compound of Example 3(b), 27 g, 27.4 mmol) in 100 mL of THF and 500 mL of methanol was added freshly ground K$_2$CO$_3$ (2.7 g, 19 mmol). The solution was stirred for 30 minutes and neutralized with IR-120 (H$^+$) resin, filtered and concentrated. The crude filtrate was then dissolved in 200 mL of dichloromethane and stirred for 24 hours with tetrabutylammoniumborohydride (10 g). The solution was diluted with dichloromethane and washed with water, saturated bicarbonate and brine. The organic fraction was then dried over MgSO$_4$ and concentrated. The residue was chromatographed over silica gel (1:1 hexane/ethyl acetate) to give 9.4 g of the title compound (53%) with a melting point of 269° C.

FABMS (NOBA) M+H calcd for C$_{33}$H$_{43}$SO$_{11}$: 647. Found: 647.

IR(KBr) 3474, 1746, 1724, 1712, 1270, 1240, 1070 cm$^{-1}$ $^1$H NMR (CDCl$_3$, 300 MHz) δ8.08 (d, J=7.1 Hz, 2H), 7.58 (t, J=7.5 Hz, 1H), 7.45 (t, J=7.8 Hz, 2H), 6.55 (s, 1H), 4.94 (d, J=8.1 Hz, 1H), 4.83 (bq, J=5.1 Hz, 1H), 4.66 (ABq, J=14.7,12.3 Hz, 2H), 4.30 (m, 2H), 4.13 (d, J=8.4 Hz, 1H), 3.91 (d, J=6.6 Hz, 1H), 2.79 (m, 1H), 2.27 (s, 3H), 2.25 (m, 2H), 2.19 (s, 3H), 2.16 (s, 3H), 2.10 (s, 4H), 1.81 (m, 1H), 1.72 (s, 3H), 1.61 (m, 2H), 1.16 (s, 3H), 1.03 (s, 3H).

$^{13}$C NMR (CDCl$_3$, 75.5 Hz) δ202.3, 170.8, 169.3, 167.0, 144.2, 132.6, 132.1, 130.1, 129.4, 128.6, 83.9, 80.9, 78.7, 75.7, 74.5, 73.9, 67.9, 57.6, 47.6, 42.7, 38.3, 26.7, 22.6, 21.0, 20.1, 15.2, 15.0, 10.8.

Example 7

3'-N-debenzoyl-3'-desphenyl-3'-N-(t-butyloxycarbonyl)-3'-(2-furyl)-2'-O-ethyloxycarbonyl-7-O-phosphonooxymethylpaclitaxel triethanolamine salt (a) Preparation of 3'-N-debenzoyl-3'-desphenyl-3'-N-(t-butyloxycarbonyl)-3'-(2-furyl)-7-O-methylthiomethylpaclitaxel

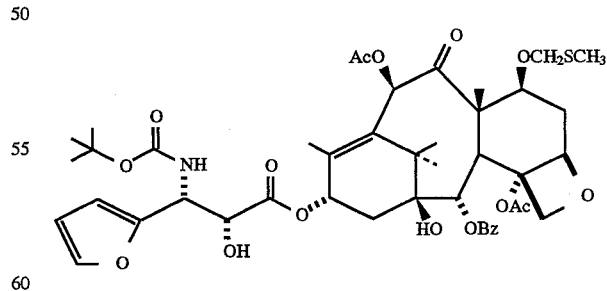

To a solution of HMDS (0.40 mL, 1.90 mmol) in 15 mL of THF was added a solution of n-BuLi (0.75 mL, 2.5M in hexanes, 1.88 mmol) and stirred 5 minutes at −55° C. To this solution was added 7-MTM baccatin III (compound of example 6, 1.03 g, 1.59 mmol) in 10 mL of THF and stirred for 10 minutes before addition of an 10 mL solution of (3R,4R)-1-(t-butyloxycarbonyl)-4-(2-furyl)-3-(triethylsilyloxy)-2-azetidinone (883 mg, 2.40 mmol). The cold bath was removed and replaced with a 0° C. bath and the reaction mixture was stirred for 30 minutes. The solution was diluted with ethyl acetate and washed with saturated NH₄Cl solution, dried over MgSO₄ and concentrated. The residue was chromatographed over silica gel (2.5:1 hexane/ethyl acetate) to give 1.5 g of the coupling product 3'-N-debenzoyl-3'-desphenyl-3'-N-(t-butyloxycarbonyl)-3'-(2-furyl)-7-O-methylthiomethyl-2'-O-triethylsilylpaclitaxel (93%).

FABMS (NOBA) M+Na calcd for $C_{50}H_{71}NSSiO_{16}$: 1036. Found: 1036.

IR(film) 3446 (s), 1720, 1368, 1242, 1166, 1144, 1124, 1066 cm$^{-1}$ $^1$H NMR (CDCl₃, 300 MHz) δ8.07 (d, J=7.2 Hz, 2H), 7.56 (m, 1H), 7.46 (t, J=7.5 Hz, 2H), 7.36 (m, 1H), 6.56 (s, 1H), 6.33 (m, 1H), 6.20 (m, 2H), 5.67 (d, J=6.9 Hz, 1H), 5.29 (bs, 2H), 4.94 (d, J=7.8 Hz, 1H), 4.75 (s, 1H), 4.65 (s, 2H), 4.28 (m, 2H), 4.16 (d, J=8.1 Hz, 1H), 3.89 (d, J=6.9 Hz, 1H), 2.80 (m, 1H), 2.46 (s, 3H), 2.37 (m, 1H), 2.22 (m, 1H), 2.16 (s, 3H), 2.10 (s, 3H), 2.04 (s, 3H), 1.84 (m, 1H), 1.74 (s, 3H), 1.65 (m, 1H), 1.33 (s, 9H), 1.20 (s, 3H), 1.19 (s, 3H), 0.81 (t, J=7.8 Hz, 9H), 0.47 (m, 6H).

$^{13}$C NMR (CDCl₃, 75.5 Hz) δ202.0, 171.2, 170.3, 169.3, 167.1, 155.3, 152.0, 141.9, 141.0, 133.6, 132.9, 130.2, 129.2, 128.7, 110.7, 107.3, 84.0, 81.1, 80.2, 78.7, 76.1, 75.7, 74.7, 74.1, 72.4, 71.1, 57.4, 52.8, 47.1, 43.3, 35.2, 33.0, 28.1, 26.3, 22.9, 21.2, 21.0, 15.0, 14.5, 10.9, 6.5, 4.3.

To a solution of the 2'-triethylsilyl ether obtained above (330 mg, 0.32 mmol) in 7 mL of THF was added tetrabutylammonium fluoride (0.35 mL, 1.0M in THF, 0.35 mmol) and stirred 10 minutes. The solution was diluted with ethyl acetate and washed with brine, dried over MgSO₄ and concentrated and the residue was chromatographed over silica gel (2:1 hexane/ethyl acetate) to give 301 mg of the title compound (95%).

FABMS (NOBA) M+H calcd for $C_{45}H_{59}NO_{16}S$: 900. Found: 900.

IR(film) 3442, 1720, 1242, 1066, 1026 cm$^{-1}$ $^1$H NMR (CDCl₃, 300 MHz) δ8.07 (d, J=7.3 Hz, 2H), 7.57 (t, J=7.3 Hz, 1H), 7.45 (t, J=7.8 Hz, 2H), 7.38 (s, 1H), 6.53 (s, 1H), 6.34 (d, J=3.2 Hz, 1H), 6.29 (d, J=3.2 Hz, 1H), 6.17 (t, J=8.1 Hz, 1H), 5.65 (d, J=6.9 Hz, 1H), 5.29 (m, 2H), 4.92 (d, J=8.0 Hz, 1H), 4.70 (m, 1H), 4.64 (d, J=4.6 Hz, 2H), 4.29 (m, 2H), 4.14 (d, J=8.3 Hz, 1H), 3.86 (d, J=6.8 Hz, 1H), 3.37(d, J=5.8 Hz, 1H), 2.77 (m, 1H), 2.38 (s, 3H), 2.32 (m, 2H), 2.16 (s, 3H), 2.10 (s, 3H), 2.02 (s, 3H), 1.77 (m, 3H), 1.73 (s, 3H), 1.33 (s, 9H), 1.17 (s, 3H), 1.12 (s, 3H).

$^{13}$C NMR (CDCl₃, 75.5 Hz) δ202.0, 172.6, 170.3, 169.2, 167.0, 155.2, 151.3, 142.4, 140.4, 133.7, 133.2, 130.2, 129.1, 128.7, 110.7, 107.4, 83.9, 81.2, 80.5, 78.6, 76.5, 76.1, 75.4, 74.6, 74.0, 72.5, 71.8, 57.4, 51.7, 47.2, 43.2, 35.2, 32.8, 28.1, 26.4, 22.6, 20.9, 15.2, 14.6, 10.9, 8.3.

(b) Preparation of 3'-N-debenzoyl-3'-desphenyl-3'-N-(t-butyloxycarbonyl)-3'-(2-furyl)-2'-O-ethyloxycarbonyl-7-O-methylthiomethylpaclitaxel

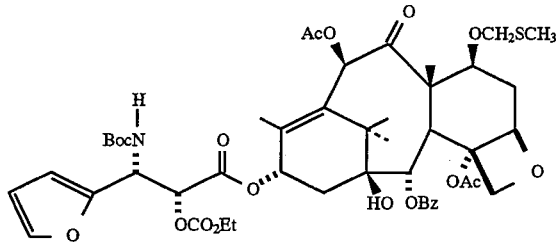

To a solution of the product of step (a) (864 mg, 0.96 mmol) in 50 mL of dichloromethane at 0° C. was added diisopropylethyl amine (2.0 mL, 11.5 mmol) and ethyl chloroformate (0.50 mL, 5.25 mmol) and stirred for 4 hours. The solution was diluted with dichloromethane and washed with saturated bicarbonate and dried over MgSO₄ and concentrated. The residue was chromatographed over silica gel (1:1 hexane/ethyl acetate) to give 884 mg of the 2' ethyl carbonate title compound (95%).

FABMS (NOBA) M+H calcd for $C_{49}H_{62}NO_{18}S$ 972.3688. Found: 972.3654.

IR(film) 1752, 1720, 1370, 1244, 1196, 1176, 1064 cm$^{-1}$ $^1$H NMR (CDCl₃, 300 MHz) δ8.09 (d, J=7.8 Hz, 2H), 7.57 (t, J=7.5 Hz, 1H), 7.46 (t, J=7.8 Hz, 2H), 7.38 (s, 1H), 6.55 (S, 1H), 6.35 (m, 1H), 6.27 (m, 1H), 6.22 (t, J=7.8 Hz, 1H), 5.67 (d, J=7.2 Hz, 1H), 5.51 (d, J=9.9 Hz, 1H), 5.34 (d, J=2.4 Hz, 1H), 5.25 (d, J=10.2 Hz, 1H), 4.95 (d, J=8.1 Hz, 1H), 4.65 (s, 2H), 4.30 (m, 2H), 4.22 (m, 2H), 3.88 (d, J=7.2 Hz, 1H), 2.81 (m, 1H), 2.41 (s, 3H), 2.36–2.21 (m, 2H), 2.16 (s, 3H), 2.11 (s, 3H), 2.09 (s, 3H), 1.83 (m, 1H), 1.74 (s, 3H), 1.67 (s, 1H), 1.59 (s, 1H), 1.34 (s, 9H), 1.29 (t, J=7.2 Hz, 3H), 1.20 (s, 3H), 1.18 (s, 3H).

$^{13}$C NMR (CDCl₃, 75.5 Hz) δ202.1, 169.9, 169.1, 167.6, 167.0, 154.0, 150.1, 142.6, 141.0, 133.6, 132.9, 130.2, 129.2, 128.7, 110.7, 107.5, 83.9, 81.1, 80.7, 78.7, 76.0, 75.7, 75.1, 74.7, 74.2, 71.8, 65.1, 57.4, 49.7, 47.1, 43.2, 35.0, 33.0, 28.1, 26.3, 22.6, 21.1, 20.9, 15.1, 14.5, 14.1, 10.9.

(c) Preparation of 3'-N-debenzoyl-3'-desphenyl-3'-N-(t-butyloxycarbonyl)-3'-(2-furyl)-2'-O-ethyloxycarbonyl-7-O-dibenzylphosphonooxymethylpaclitaxel

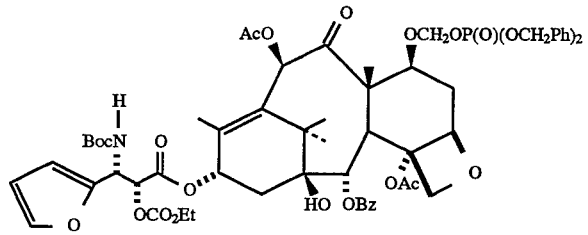

To a solution of the product of step (b) (230 mg, 0.236 mmol) in 10 mL of anhydrous THF was added 300 mg of 4A sieves, dibenzylphosphate (270 mg, 0.98 mmol) and recrystallized NIS (62 mg, 0.28 mmol). To this solution was added silver trifluoromethanesulfonate (45 mg, 0.17 mmol) and the solution stirred for 3 hours. The solution was filtered through Celite and diluted with ethyl acetate and washed with 10% NaS₂O₈, sautruated bicarbonate, and brine, dried over MgSO₄ and concentrated. The residue was chromatographed over silica gel (15% acetonitrile/chloroform) to give 219 mg of the dibenzyl phosphate title compound (77%).

FABMS (NOBA) M+Na calcd for $C_{61}H_{72}NPO_{22}Na$ 1224. Found: 1224.

IR(film) 3422 (br), 1750, 1722, 1370, 1244, 1160, 1036, 1016, 1000, 976, 944 cm⁻¹

¹H NMR (CDCl₃, 300 MHz) δ8.08 (d, J=6.9 Hz, 2H), 7.58 (t, J=7.2 Hz, 1H), 7.46 (t, J=7.8 Hz, 2H), 7.39 (s, 1H), 7.31 (m, 10), 6.35 (m, 2H), 6.28 (s, 1H), 6.21 (t, J=7.8 Hz, 1H), 5.64 (d, J=6.9 Hz, 1H), 5.50 (d, J=10.5 Hz, 1H), 5.39 (d, J=6.6 Hz, 1H), 5.32 (d, J=2.4 Hz, 1H), 5.25 (d, J=9.9 Hz, 1H), 5.01 (dd, J=8.1, 6.3 Hz, 5H), 4.86 (d, J=8.4 Hz, 1H), 4.29–4.09 (m, 4H), 3.85 (d, J=6.9 Hz, 1H), 2.77 (m, 1H), 2.40 (s, 3H), 2.30 (m, 2H), 2.16 (s, 3H), 1.99 (s, 3H), 1.94 (m, 1H), 1.70 (s, 3H), 1.67 (s, 1H), 1.54 (s, 1H), 1.34 (s, 9H), 1.28 (t, J=7.2 Hz, 3H), 1.20 (s, 3H), 1.17 (s, 3H).

¹³C NMR (CDCl₃, 75.5 Hz) δ201.8, 169.9, 169.2, 167.7, 167.0, 155.1, 154.0, 150.0, 142.74, 141.1, 133.7, 132.9, 130.2, 129.1, 128.7, 128.5, 128.4, 128.0, 110.7, 107.6, 93.8, 84.1, 81.6, 80.8, 80.7, 78.8, 76.3, 75.1, 74.6, 71.8, 69.3, 69.2, 65.1, 57.0, 49.7, 46.7, 43.2, 35.0, 28.1, 26.4, 22.6, 21.2, 20.8, 14.6, 14.1, 10.5.

(d) Preparation of 3'-N-debenzoyl-3'-desphenyl-3'-N-(t-butyloxycarbonyl)-3'-(2-furyl)-2'-O-ethyloxycarbonyl-7-O-phosphonooxymethylpaclitaxel triethanolamine salt

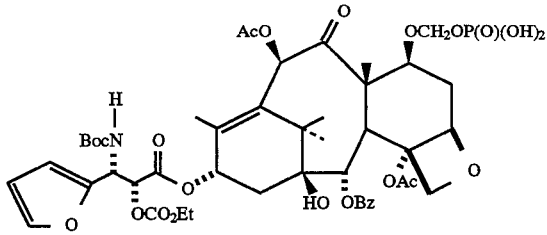

To a solution of the product of step (c) (311 mg, 0.259 mmol) in 25 mL of ethyl acetate was added 60 mg of Pd on carbon (10%) and the solution stirred under an atmosphere of H₂ for 30 minutes. The catalyst was removed by filtration through Celite and the filtrate concentrated in vacuo. The residue was dissolved in 3 mL of ethyl acetate and triethananolamine added (2.3 mL, 0.1M in ethyl acetate, 0.23 mmol). The solution was concentrated and the residue was chromatographed over C₁₈ (40% acetonitrile/water) and lyophilized to give 205 mg of the phosphate triethanolamine salt (67%).

FABMS (NOBA) M+Na calcd for $C_{47}H_{60}HPO_{22}Na$ 1044. Found: 1044.

IR(film) 3432 (br), 1752, 1722, 1372, 1246, 1158, 1108, 1096, 1070, 1002 cm⁻¹

¹H NMR (d6 acetone/D₂O, 300 MHz) δ8.09 (d, J=7.2 Hz, 2H), 7.62 (m, 2H), 7.52 (t, J=7.5 Hz, 2H), 6.48 (d, J=3.3 Hz, 1H), 6.42 (m, 2H), 6.16 (t, J=8.7 Hz, 1H), 5.65 (d, J=6.9 Hz, 1H), 5.46 (d, J=3.6 Hz, 1H), 5.30 (d, J=3.6 Hz, 1H), 5.17 (bs, 1H), 5.01 (bd, J=9.0 Hz, 1H), 4.19 (bs, 1H), 4.18 (m, 5H), 3.95 (m, 4H), 3.87 (d, J=6.9 Hz, 1H), 3.68 (s, 10H), 3.50 (bt, J=4.8 Hz, 4H), 2.95 (m, 1H), 2.44 (s, 3H), 2.41 (m, 2H), 2.16 (s, 3H), 1.99 (s, 3H), 1.94 (m, 1H), 1.68 (s, 3H), 1.34 (s, 9H), 1.24 (t, J=6.9 Hz, 3H), 1.17 (s, 6H).

Example 8

3'-N-debenzoyl-3'-desphenyl-3'-N-(t-butyloxycarbonyl)-3'-(2-thienyl)-2'-O-ethyloxycarbonyl-7-O-phosphonooxymethylpaclitaxel triethanolamine salt (a) Preparation of 3'-N-debenzoyl-3'-desphenyl-3'-N-(t-butyloxycarbonyl)-3'-(2-thienyl)-7-O-methylthiomethylpaclitaxel

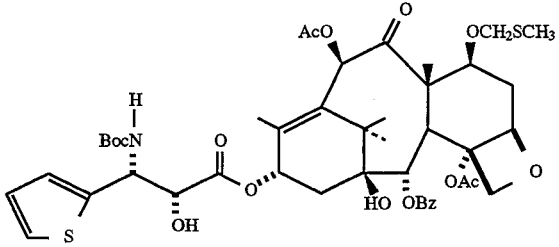

To a solution of HMDS (0.5 mL, 2.4 mmol) in 18 mL of THF at −55° C. was added n-BuLi (0.85 mL, 2.5M in hexanes, 2.1 mmol). After 10 minutes 7-MTM baccatin III (1.15 g, 1.78 mmol) in 18 mL of THF was added dropwise and stirred in the cold for 10 minutes. (±)cis-1-(t-Butyloxycarbonyl)-4-(2-thienyl)-3-(triethylsilyloxy)-2-azetidinone (2.80 g, 7.3 mmol) in 18 mL of THF was added and the cold bath allowed to slowly warm to 0° C. over 30 minutes. The solution was diluted with ethyl acetate and washed with saturated NH₄Cl solution, dried over MgSO₄ and concentrated. The residue was chromatographed over silica gel (5:1 hexane/ethyl acetate) to give 1.87 g of recovered lactam (3:1 hexane/ethyl acetate) to give 1.44 g of the coupling product 3'-N-debenzoyl-3'-desphenyl-3'-N-(t-butyloxycarbonyl)-3'-(2-thienyl)-7-O-methylthiomethyl-2'-O-triethylsilylpaclitaxel (78%).

FABMS (NOBA) M+Na calcd for $C_{51}H_{71}NO_{15}S_2SiNa$ 1052. Found: 1052.

IR(film) 3442 (br), 1720, 1490, 1368, 1270, 1242, 1162, 1110, 1064, 1024, 984, 754 cm⁻¹

¹H NMR (CDCl₃, 300 MHz) δ8.09 (d, J=7.2 Hz, 2H), 7.57 (t, J=7.6 Hz, 1H), 7.47 (t, J=7.8 Hz, 2H), 7.22 (m, 1H), 6.95 (m, 2H), 6.55 (s, 1H), 6.21 (t, J=9.3 Hz, 1H), 5.68 (d, J=6.9 Hz, 1H), 5.49 (bd, 1H), 5.39 (bd, J=9.6 Hz, 1H), 4.94 (d, J=7.8 Hz, 1H), 4.65 (s, 2H), 4.57 (s, 1H), 4.28 (m, 2H), 4.17 (d, J=8.4 Hz, 1H), 3.88 (d, J=6.9 Hz, 1H), 2.80 (m, 1H), 2.46 (s, 3H), 2.37 (m, 1H), 2.20 (m, 1H), 2.17 (s, 3H), 2.10 (s, 3H), 2.03 (s, 3H), 1.84 (m, 1H), 1.74 (s, 3H), 1.68 (s, 1H), 1.62 (s, 1H), 1.31 (s, 9H), 1.20 (s, 6H), 0.84 (t, J=7.8 Hz, 9H), 0.50 (m, 6H).

¹³C NMR (CDCl₃, 75.5 Hz) δ201.9, 171.1, 170.7, 170.1, 169.3, 167.0, 155.1, 142.8, 140.9, 133.6, 132.9, 130.2, 129.2, 128.7, 126.9, 124.6, 83.9, 81.2, 80.1, 78.8, 77.4, 76.0, 75.7, 75.2, 74.8, 74.1, 71.3, 57.4, 53.8, 47.0, 43.3, 35.3, 33.3, 28.1, 26.3, 23.0, 21.3, 20.9, 14.9, 14.4, 10.9, 6.6, 4.5.

To a solution of the 2'-triethylsilyl ether obtained above (1.41 g, 1.37 mmol) in 14 mL of THF was added tetrabutylammonium fluoride (1.4 mL, 1.0M in THF, 1.40 mmol). The solution was stirred for 30 minutes, diluted with ethyl acetate and washed with brine, dried over MgSO₄ and concentrated. The residue was chromatographed over silica gel (1:1 hexane/ethyl acetate) to give 1.16 g of the title compound (92%).

FABMS (NOBA) M+Na calcd for $C_{45}H_{57}NO_{15}S_2Na$ 938. Found: 938.

IR(film) 3440 (br), 1720, 1368, 1242, 1168, 1106, 1066, 710 cm$^{-1}$ $^1$H NMR (CDCl$_3$, 300 MHz) δ8.08 (d, J=7.2 Hz, 2H), 7.59 (m, 1H), 7.47 (t, J=7.8 Hz, 2H), 7.24 (m, 1H), 7.07 (m, 1H), 6.99 (m, 1H), 6.53 (s, 1H), 6.18 (t, J=8.1 Hz, 1H), 5.66 (d, J=6.9 Hz, 1H), 5.49 (d, J=9.6 Hz, 1H), 5.32 (d, J=9.6 Hz, 1H), 4.92 (d, J=7.8 Hz, 1H), 4.63 (m, 3H), 4.28 (m, 2H), 4.15 (d, J=8.4 Hz, 1H), 3.86 (d, J=6.9 Hz, 1H), 3.47 (d, J=5.4 Hz, 1H), 2.78 (m, 1H), 2.36 (s, 3H), 2.34 (, 2H), 2.17 (s, 3H), 2.10 (s, 3H), 2.00 (s, 3H), 1.83 (m, 1H), 1.74 (s, 3H), 1.72 (s, 1H), 1.61 (s, 1H), 1.33 (s, 9H), 1.21 (s, 3H), 1.18 (s, 3H).

$^{13}$C NMR (CDCl$_3$, 75.5 Hz) δ201.9, 172.3, 170.3, 169.2, 167.0, 154.0, 141.5, 140.2, 133.7, 133.3, 130.2, 129.1, 128.7, 127.0, 125.4, 125.4, 83.9, 81.3, 80.4, 78.6, 76.1, 75.4, 74.5, 74.0, 73.4, 72.5, 57.5, 52.8, 47.2, 43.2, 35.3, 32.9, 28.2, 26.4, 22.6, 20.9, 15.1, 14.7, 10.8.

(b) Preparation of 3'-N-debenzoyl-3'-desphenyl-3'-N-(t-butyloxycarbonyl)-3'-(2-thienyl)-2'-O-ethyloxycarbonyl-7-O-methylthiomethylpaclitaxel

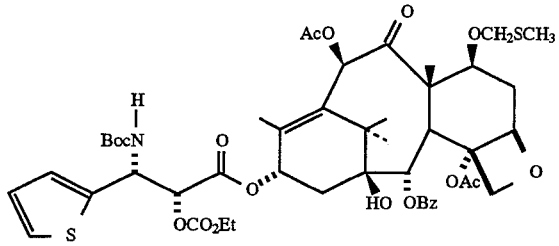

To a solution of the product of step (a) (621 mg, 0.677 mmol) in 35 mL of dichloromethane at 0° C. was added diisopropylethyl amine (1.20 mL, 6.89 mmol) and ethyl chloroformate (0.35 mL, 3.7 mmol) and stirred for 1 hour. The cold bath was removed and the solution stirred for 2 hours and was diluted with dichloromethane and was washed with saturated bicarbonate and dried over MgSO$_4$ and concentrated. The residue was chromatographed over silica gel (1:1 hexane/ethyl acetate) to give 528 mg of the title compound (79%).

FABMS (NOBA) M+Na calcd for C$_{48}$H$_{61}$NO$_{17}$S$_2$Na 1010. Found: 1010.

IR(film) 3510, 3440, 1752, 1720, 1370, 1244, 1198, 1170, 1026, 988, 756 cm$^{-1}$ $^1$H NMR (CDCl$_3$, 300 MHz) δ8.09 (d, J=7.2 Hz, 2H), 7.58 (m, 1H), 7.48 (t, J=7.8 Hz, 2H), 7.26 (m, 1H), 6.99 (, 2H), 6.55 (s, 1H), 6.23 (t, J=9.0 Hz, 1H), 5.68 (d, J=6.9 Hz, 2H), 5.33 (d, J=9.9 Hz, 1H), 5.25 (d, J=2.4 Hz, 1H), 4.94 (d, J=7.8 Hz, 1H), 4.65 (s, 2H), 4.33–4.08 (m, 5H), 3.88 (d, J=6.9 Hz, 1H), 2.80 (m, 1H), 2.40 (s, 3H), 2.40–2.20 (m, 2H), 2.16 (s, 3H), 2.11 (s, 3H), 2.07 (s, 3H), 1.83 (m, 1H), 1.74 (s, 3H), 1.69 (s, 1H), 1.60 (s, 1H), 1.33 (s, 9H), 1.31 (t, J=7.2 Hz, 9H), 1.20 (s, 3H), 1.19 (s, 3H).

$^{13}$C NMR (CDCl$_3$, 75.5 Hz) δ202.0, 169.7, 169.1, 167.5, 167.1, 154.0, 140.9, 133.6, 132.9, 130.2, 129.2, 128.7, 127.2, 125.4, 125.3, 83.9, 81.2, 80.6, 78.8, 76.9, 76.0, 75.7, 74.7, 74.2, 72.8, 72.0, 65.2, 57.4, 50.9, 47.1, 43.3, 35.1, 33.0, 28.1, 26.4, 22.7, 21.2, 20.9, 15.1, 14.5, 14.1, 10.9.

(c) Preparation of 3'-N-debenzoyl-3'-desphenyl-3'-N-(t-butyloxycarbonyl)-3'-(2-thienyl)-2'-O-ethyloxycarbonyl-7-O-dibenzylphosphonooxymethylpaclitaxel

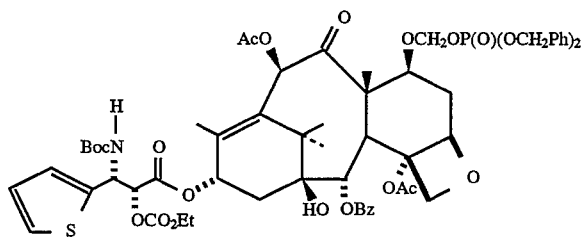

To a solution of the product of step (b) (516 mg, 0.522 mmol) in 15 mL of anhydrous THF was added 530 mg of 4A sieves, dibenzylphosphate (576 mg, 2.09 mmol) and recrystalized NIS (136 mg, 0.604 mmol). To this solution was added silver trifluoromethanesulfonate (50 mg, 0.194 mmol) and the solution stirred for 1 hour. The solution was filtered through Celite and diluted with ethyl acetate and washed with 10% NaS$_2$O$_8$, saturated bicarbonate and brine, dried over MgSO$_4$ and concentrated. The residue was chromatographed over silica gel (15% acetonitrile/chloroform) to give 535 mg of the title compound (84%).

FABMS (NOBA) M+Na calcd for C$_{61}$H$_{72}$NO$_{21}$PSNa 1240. Found: 1240.

IR(film) 3424 (br), 1750, 1722, 1370, 1244, 1016, 1000, 944 cm$^{-1}$ $^1$H NMR (CDCl$_3$, 300 MHz) δ8.08 (d, J=7.0 Hz, 2H), 7.58 (m, 1H), 7.47 (t, J=7.5 Hz, 2H), 7.28 (m, 11H), 6.99 (m, 2H), 6.33 (s, 1H), 6.22 (t, J=7.8 Hz, 1H), 5.66 (m, 2H), 5.39 (t, J=6.6 Hz, 1H), 5.34 (d, J=12 Hz, 1H), 5.22 (d, J=2.4 Hz, 1H), 5.01 (dd, J=8.1, 6.0 Hz, 5H), 4.86 (d, J=7.8 Hz, 1H), 4.29–4.08 (m, 5H), 3.85 (d, J=6.6 Hz, 1H), 2.76 (m, 1H), 2.39 (s, 3H), 2.35–2.18 (m, 2H), 2.16 (s, 3H), 1.97 (s, 4H), 1.69 (s, 4H), 1.33 (s, 9H), 1.30 (t, J=7.2 Hz, 3H), 1.20 (s, 3H), 1.17 (s, 3H).

$^{13}$C NMR (CDCl$_3$, 75.5 Hz) δ197.4, 165.4, 164.9, 163.3, 162.7, 150.6, 149.7, 136.7, 136.0, 129.4, 128.6, 125.9, 124.7, 124.3, 124.2, 124.1, 123.6, 122.9, 121.1, 121.0, 89.4, 79.8, 77.3, 76.5, 76.3, 74.4, 72.0, 70.7, 70.3, 67.7, 64.9, 64.9, 60.9, 52.7, 46.5, 42.3, 38.9, 30.7, 23.8, 22.0, 18.3, 17.0, 16.4, 10.3, 9.8, 6.2.

(d) Preparation of 3'-N-debenzoyl-3'-desphenyl-3'-N-(t-butyloxycarbonyl)-3'-(2-thienyl)-2'-O-ethyloxycarbonyl-7-O-phosphonooxymethylpaclitaxel triethanolamine salt

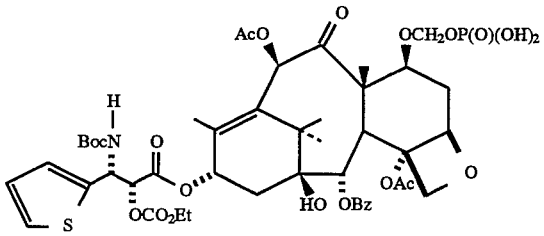

To a solution of the product of step (c) (512 mg, 0.42 mmol) in 30 mL of ethyl acetate was added 53 mg of Pd on carbon (10%) and the solution stirred under an atmosphere of H$_2$ for 3 hours. The catalyst was removed by filtratation through Celite and the filtrate concentrated in vacuo. The residue was dissolved in 2 mL of ethyl acetate and triethanolamine added (4.0 mL, 0.1M in ethyl acetate, 0.40 mmol). The solution was concentrated and the residue was chromatographed over $C_{18}$ (40% acetonitrile/water) and lyophilized to give 280 mg of the phosphate triethanolamine salt (56%). HPLC analysis showed the purity of the salt to be 96%.

FABMS (NOBA) M+Na calcd for $C_{47}H_{60}NO_{21}PS$ 1060. Found: 1060.

IR(KBr) 3422 (br), 1750, 1720, 1372, 1246, 1162, 1096, 1068, 1000 $cm^{-1}$ $^1$H NMR ($d_6$ acetone/$D_2O$, 300 MHz) δ8.06 (d, J=7.2 Hz, 2H), 7.63 (t, J=7.2 Hz, 1H), 7.52 (t, J=7.8 Hz, 2H), 7.38 (d, J=4.2 Hz, 1H), 7.16 (d, J=3.5 Hz, 1H), 7.01 (dd, J=5.1, 3.6 Hz, 1H), 6.37 (s, 1H), 6.11 (t, J=8.7 Hz, 1H), 5.61 (d, J=6.9 Hz, 1H), 5.60 (s, 1H), 5.26 (d, J=4.5 Hz, 1H), 5.14 (t, J=6.6 Hz, 1H), 5.00 (d, J=8.4 Hz, 1H), 4.86 (dd, J=12.0, 6.3 Hz, 1H), 4.17 (m, 5H), 4.00 (s, 7H), 3.92 (t, J=4.8 Hz, 6H), 3.84 (d, J=6.9 Hz, 1H), 3.48 (t, J=5.4 Hz, 6H), 2.94 (m, 1H), 2.42 (s, 3H), 2.36 (m, 1H), 2.27 (m, 1H), 2.15 (s, 3H), 1.95 (s, 4H), 1.66 (s, 3H), 1.30 (s, 9H), 1.23 (t, J=7.2 Hz, 3H), 1.14 (s, 6H).

Example 9

10-Desacetyl-3'-N-desbenzoyl-3'-N-(t-butyloxycarbonyl)-10-O-(phosphonooxymethyl) paclitaxel (a) Preparation of 10-desacetyl-10-O-benzyloxycarbonyl-7-O-triethylsilylbaccatin III

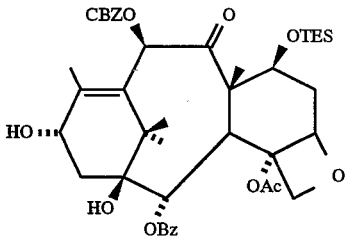

To a dry flask under an argon atmosphere containing 7-O-triethylsilyl-10-desacetyl baccatin III (2.093 g, 3.177 mmol) was added dry THF (30 mL) and cooled to –70° C. To this was added 1.6M n-butyllithium (2.38mL, 3.81 mmol) in a dropwise fashion. After stirring for 15 min, benzyl chloroformate (0.91 mL, 6.35 mmol) was added dropwise. The resulting mixture was stirred for 3 h with gradual warming to ambient temperature. The reaction was quenched with 25 mL of sat. $NH_4Cl$, washed with brine, and dried with $MgSO_4$. Flash chromatography (silica gel, 30–45% ethyl acetate/hexane) furnished 2.24 g (89%) of the title compound as a white foam.

$^1$H NMR (300 MHz, $CDCl_3$) δ8.10 (d, J=8.0, 2H); 7.63–7.58 (m, 1H) 7.47 (t, J=8.0, 2H); 7.41–7.26 (m, 5H); 6.29 (s, 1H); 5.61 (d, J=7.0, 1H); 5.20 (q, J=12.2, 2H); 4.96 (d, J=9.0, 1H); 4.87–4.84 (m, 1H); 4.48 (dd, J=6.7, J=10.4, 1H); 4.30 (d, J=8.5, 1H); 4.14 (d, J=8.5, 1H); 3.84 (d, J=7.0, 1H); 2.58–2.48 (m, 1H); 2.29 (m, 4H); 2.20 (s, 3H); 2.03 (d, J=5.0, 1H); 1.92– 1.83 (m, 1H); 1.68 (s, 3H); 1.17 (s, 3H); 1.04 (s, 3H); 0.91 (t, J=7.5, 9H); 0.57 (q, J=7.4, 6H).

(b) Preparation of 10-desacetyl-10-O-benzyloxycarbonyl-3'-N-debenzoyl-3'-N-(t-butyloxycarbonyl)-2',7-bis-O-triethylsilylpaclitaxel

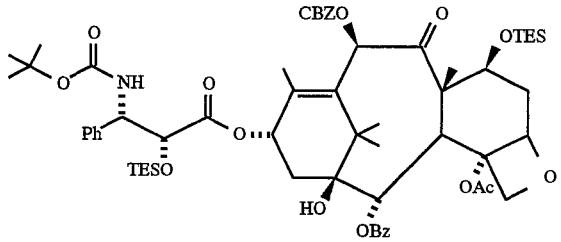

To a dry flask containing the product of step (a) (3.50 g, 4.42 mmol) was added a small amount of toluene and the solution was then concentrated under vacuum. This flask was placed under an argon atmosphere and 100 mL of dry THF was added. The flask was cooled to –70° C. and 1.0M lithium hexamethyldisilazide (6.19 mL, 6.19 mmol) was added in a dropwise fashion. After stirring for 20 min, a solution of (3R,4S)-1-(t-butyloxycarbonyl)-4-phenyl-3-triethylsilyloxy-2-azetidinone (2.58 g, 7.07 mmol) in 10 mL dry THF was added dropwise. The reaction mixture was stirred for 3.5 h, gradually warming to ambient temperature. It was then quenched with 70 mL of sat. $NH_4Cl$, washed with brine and dried with $MgSO_4$. Flash chromatography (silica gel, 5–15% ethyl acetate/hexanes) provided 5.12 g (99%,) of the title compound as a white foam.

$^1$H NMR (300MHz, $CDCL_3$) δ8.11 (d, J=8.0, 2H); 7.60–7.58 (m, 1H); 7.48 (t, J=8.0, 2H); 7.24–7.26 (m, 10H); 6.32–6.26 (m, 2H); 5.69 (d, J=7.0, 1H); 5.47 (bd, J=9.7, 1H); 5.31–5.10 (m, 3H); 4.94 (d, J=8.5, 1H); 4.56 (s, 1H); 4.46 (dd, J=6.9, J=10.6, 1H); 4.31 (d, J=8.3, 1H); 4.17 (d, J=8.3, 1H); 3.81 (d, J=7.0, 1H); 2.53 (s, 3H); 2.48–2.33 (m, 1H); 2.22–2.17 (m, 1H); 2.09 (s, 3H); 1.95–1.86 (m, 1H); 1.70 (s, 3H); 1.65 (s, 1H); 1.52 (s, 1H); 1.30 (s, 9H); 1.26–1.19 (m, 6H); 0.94–0.87 (m. 9H); 0.80–0.75 (m, 9H); 0.61–0.53 (m, 6H); 0.48–0.30 (m, 6H).

(c) Preparation of 10-desacetyl-3'-N-debenzoyl-3'-N-(t-butyloxycarbonyl)-7-O-triethylsilylpaclitaxel

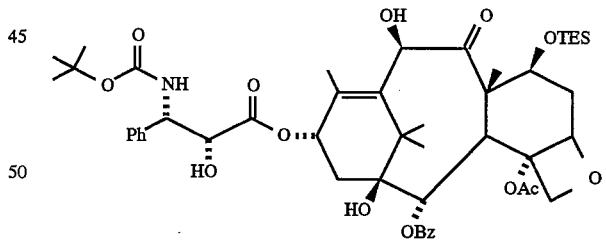

The product of step (b) (5.12 g, 4.40 mmol) was dissolved into 100 mL of ethyl acetate, transferred to a Parr bottle and placed under a blanket of argon. To this was added 10% palladium on carbon (2.4 g) and the reaction mixtre was placed on a Parr hydrogenation apparatus (55 psi) for a period of 8 h. The reaction mixture was filtered through a plug of Celite and concentrated. Flash chromatography (silica gel, 15–20% ethyl acetate/hexane) provided 3.24 g (79%) of the title compound as a white foam. Hydrolysis of the 2'-triethylsilyl group of the product of step (b) was a result of trace acidic residues in the Parr equipment.

$^1$H NMR (300 MHz, $CDCl_3$) δ8.10 (d,J=8.0, 2H); 7.63–7.58 (m, 1H); 7.49 (d, J=8.0, 2H); 7.39–7.26 (m. 5H);

6.27–6.17 (m, 1H); 5.64 (d, J=7.2); 5.42 (d, J=9.4, 1H); 5.28–5.25 (m, 1H); 5.12 (s, 1H); 4.92 (d, J=8.6, 1H); 4.62 (bs, 1H); 4.38–4.28 (m, 3H); 4.17 (d, J=8.5, 1H); 3.85 (d, J=6.7, 1H); 3.36 (d, J=5.3, 1H); 2.49–2.40 (m, 1H); 2.36 (s, 3H); 2.25 (bd, J=8.7, 2H); 1.99–1.91 (m, 1H); 1.85 (s, 3H); 1.74 (s, 3H); 1.69 (s, 1H), 1.67 (s, 1H); 1.35 (s, 9H); 1.22 (s, 3H); 1.11 (s, 3H); 0.93 (t, J=7.5 9H); 0.61–0.49 (m, 6H).

(d) Preparation of 10-desacetyl-2'-O-benzyloxycarbonyl-3'-N-debenzoyl-3'-N-(t-butyloxycarbonyl)-7-O-triethylsilylpaclitaxel

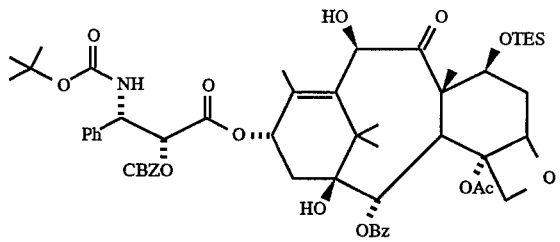

To a flask containing the product of step (c) (3.24 g, 3.51 mmol) was added 30 mL of dry dichloromethane. The flask was placed under argon and cooled to 0° C. N,N-diisopropylethylamine (1.22 mL, 7.02 mmol) was added to the reaction mixture, followed by addition of benzyl chloroformate (1.00 mL, 7.02 mmol) in a dropwise manner. After 15 min, the cooling bath was removed and the reaction allowed to stir at ambient temperature for 7 h. The mixture was quenched with 30 mL sat. NH$_4$Cl, washed with brine and dried with MgSO$_4$. Flash chromatography (silica gel, 7–20% ethyl acetate/hexane) provided 3.24 g (89%) of the title compound as a white solid.

$^1$H NMR (300 MHz, CDCl$_3$) δ8.10 (d, J=8.0, 2H); 7.62–7.57 (m, 1H); 7.48 (t, J=8.0, 2H); 7.40–7.26 (m, 10H); 6.33–6.27 (m, 1H); 5.66 (d, J=7.0, 1H); 5.49–5.42 (m, 2H); 5.31 (s, 1H); 5.22–5.13 (m , 3H); 4.93 (d, J-9.4, 1H); 4.38 (dd, J=6.5, J=10.7, 1H); 4.34–4.28 (m, 2H); 4.18 (d J=8.3, 1H); 3.90 (d, J=6.7, 1H); 2.52–2.30 (m, 4H); 2.24–2.20 (m, 1H); 1.97–1.87 (m, 3H); 1.74 (s, 3H); 1.59 (s, 3H); 1.32 (s, 9H); 1.26, (s, 3H); 1.11 (s, 3H); 0.96–0.88 (m, 9H); 0.61–0.48 (m, 6H).

(e) Preparation of 10-desacetyl-2'-O-benzyloxycarbonyl-3'-N-debenzoyl-3'-N-(t-butyloxycarbonyl)-10-O-(dibenzylphosphonooxymethyl)-7-triethylsilylpaclitaxel

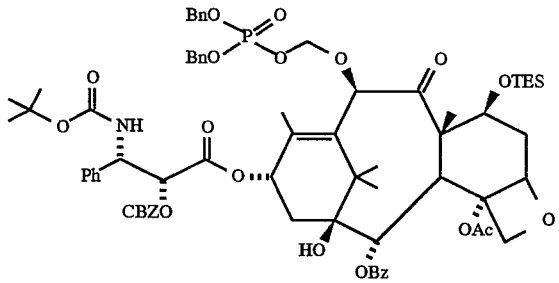

The product of step (d) was dissolved into 13.5 mL (54%) of DMSO, 8.75 mL (35%) acetic anhydride and 2.75 mL (11%) glacial acetic acid and placed under an atmosphere of argon. The reaction mixture stirred for 56 h, after which it was diluted with ethyl acetate to a volumn of 60 mL. The solution was washed with sat. NaHCO$_3$ until neutral by pH paper and then washed with brine. The organic fraction was dried with MgSO$_4$ and concentrated. Flash chromatography with 15–20% EtOAc/hexane provided 3.12 g of crude white foam with the desired thiomethyl acetal product (i.e. 10-desacetyl-2'-O-benzyloxycarbonyl-3'-N-debenzoyl-3'-N-(t-butyloxycarbonyl)-10-O-(methylthiomethyl)-7-O-triethylsilylpaclitaxel accounting for 70% of the material by NMR.

The above crude mixture (3.12 g) was then dissolved in 1,2-dichloroethane (61 mL) and placed under a blanket of argon. 4 Å powdered molecular sieves (3.12 g) were added and the resulting heterogeneous mixture was stirred vigorously. To this was added a solution of recrystallized N-iodosuccinimide (0.830 g, 3.69 mmol) and dibenzyl phosphate (1.027 g, 3.69 mmol) in dry THF (46 mL) via cannula. The resulting mixture was stirred for 5 h, filtered through a plug of Celite, and diluted to a volume of 250 mL with ethyl acetate It was washed with (2×125 mL) of cold 2% NaHSO$_3$, cold 6% NaHCO$_3$ (2×125 mL) and brine. The organic phase was dried with MgSO$_4$ and concentrated. Flash chromatography (silica gel, 25–35% ethyl acetate/hexane) provided 1.52 g (40%) of title compound as a white solid.

$^1$H NMR (CDCl$_3$, 300 MHz) δ8.08 (d, J=7.0, 2H); 7.59–7.55 (m, 1H); 7.46 (t, J=7.2, 2H); 7.38–7.25 (m, 20H); 6.30 (t, J=8.5, 1H); 5.65 (d, J=6.8, 1H); 5.49–5.39 (m, 4H); 5.32 (s, 1H); 5.18–4.19 (m, 4H); 4.93 (d, J=9.2, 1H); 4.44 (dd, J=6.6, J=10.2, 1H); 4.31 (d, J=8.4, 1H); 4.16 (d, J=8.5, 1H); 3.80 (d, J=6.9, 1H); 2.69–2.39, (m, 4H), 2.33–2.23 (m, 3H); 2.03 (s, 3H); 1.90 (t, J=12.6, 1H); 1.68–1.63 (m, 6H); 1.28 (s, 9H); 1.16–1.10 (m, 6H); 0.93 (t, J=7.4, 9H); 0.55 (q, J=7.8, 6H).

$^{13}$C NMR (CDCl$_3$, 75.5 MHz) δ204.1, 169.7, 167.9, 167.1, 151.1, 140.7, 135.7, 133.6, 130.2, 129.2, 128.9, 128.8, 128.7, 128.6, 128.5, 128.4, 128.3, 128.2, 128.0, 127.8, 126.4, 90.4, 84.2, 81.1, 80.4, 79.3, 78.8, 74.9, 72.8, 72.0, 70.5, 69.2, 69.1, 69.0, 58.1, 46.8, 43.2, 37.1, 35.0, 28.1, 26.5, 22.8, 21.0, 14.1, 10.0, 6.9, 5.5.

M. S. (FAB) m/z+: 1345

(f) Preparation of 10-desacetyl-2'-O-benzyloxycarbonyl-3'-N-debenzoyl-3'-N-(t-butyloxycarbonyl)-10-O-(dibenzylphosphonooxymethyl)paclitaxel

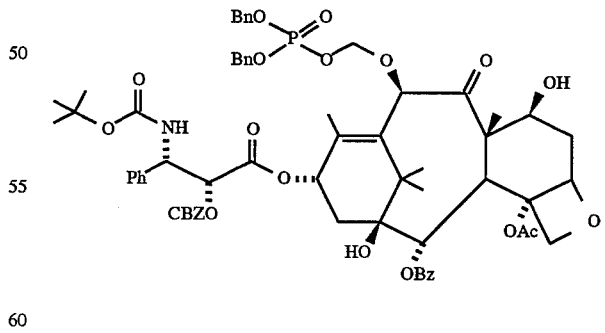

A solution of the product of step (e) (50.8 mg, 0.038 mmol) in dry THF (2.5 mL), under argon was cooled to –40° C. To this solution was added tetrabutylammonium fluoride (0.057 mL, 0.057 mmol) in THF (1.0M) in a dropwise manner. The reaction mixture stirred for 1.5 h with gradual warming to –20° C. The mixture was quenched with 15 mL sat. NH$_4$Cl and diluted with 30 mL EtOAc. The organic phase was washed with 2×15 mL NaHCO₃, and brine. It was dried with MgSO₄ and concentrated. Preparative layer chromatography (silica gel, 50% ethyl acetate/hexane) provided 36 mg (77%) of title compound as a white powder.

¹H NMR (CDCl₃, 300 MHz) δ8.10 (d, J=8.5, 2H); 7.60–7.55 (m, 1H); 7.49–7.44 (m, 2H); 7.36–7.18 (m, 20H); 6.27–6.22 (m, 1H); 5.78 (s, 1H); 5.67 (d, J=7.0, 1H); 5.44–5.34 (m, 3H); 5.27 (d, J=2.2, 1H); 5.24–5.05 (m, 4H); 5.01–4.91 (m, 4H); 4.39–4.28 (m, 2H); 4.17 (d, J=8.2, 1H); 3.87 (d, J=7.0, 1H); 2.58–2.51 (m, 1H); 2.41 (s, 3H); 2.40–2.18 (m, 2H), 2.00–1.87 (m, 5H); 1.73–1.69 (m, 4H); 1.30 (s, 9H); 1.22–1.15 (m, 6H).

M.S. (FAB) m/z+: 1231

(g) Preparation of 10-desacetyl-3'-N-desbenzoyl-3'-N-(t-butyloxycarbonyl)-10-O-(phosphonooxymethyl)paclitaxel triethanolamine salt

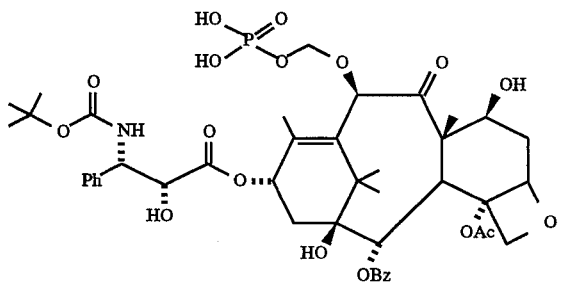

A 500 mL Parr bottle was charged with 10-desacetyl-2'-O-benzyloxycarbonyl-3'-N-debenzoyl-3'-N-(t-butyloxycarbonyl)-10-O-(dibenzylphosphonooxymethyl) paclitaxel (264.9 mg, 0.215 mmol) and ethyl acetate (20 mL). The flask was then flushed with argon and 10% Pd/C (318 mg) was added. The resulting mixture was placed on a Parr apparatus with a 55 pounds per square inch (psi) hydrogen atmosphere. The reaction was monitored by HPLC (70:30 CH₃CN/Q8 buffer pH 6.0, 1.00 mL/min., Zorbax C-18 column, 25.0 cm, λ=230 nm) until no starting material was evident (12.5 hours). The mixture was filtered through a plug of Celite, which was washed with ethyl acetate and a small amount of dichloromethane. The resulting filtrate was concentrated and the residue was taken up in 5 dichloromethane (5 mL). Addition of hexane caused a white precipitate to form, of which 140.3 mg of the free acid (80% purity by HPLC) was isolated as a white solid. This material was passed directly on to the next step.

To a flask containing the above free acid (140 mg, 0.153 mmol) was added dichloromethane (10 mL). The resulting solution was then treated with 0.100M triethanolamine solution in ethyl acetate (1.16 mL, 0.116 mmol) which caused the solution to become turbid. Approximately 2 mL of hexane was added and the mixture was placed at −20° C. overnight. The resulting precipitate was filtered through a 4.0–5.5 μm fritted glass funnel. The solid was removed and placed under vacuum for 4 h to yield 69.9 mg (42%) the title triethanolamine salt as a gray powder, which was determined to be 95–96% pure by HPLC analysis. (T_R=2.05 min, 70:30 CH₃CN/Q8 Buffer pH 6.0, 1.00 mL/min, Zorbax C-18 25.0 cm, λ=230 nm).

¹H-NMR (d₆-acetone/D₂O, 300 MHz): δ8.03 (d, J=7.4, 2H); 7.65 (t, J=7.3, 1H); 7.54 (t, J=7.6, 2H); 7.42–7.33 (m, 5H); 7.21 (t, J=7.0, 1H); 6.09 (t, J=9.0, 1H); 5.81 (s, 1H); 5.59 (d, J=7.0, 1H); 5.12 (bs, 2H); 4.93 (d, J=8.4, 2H), 4.56 (d, J=4.9, 1H); 4.31–4.26 (m, 1H); 4.11 (s, 2H); 3.41–3.37 (m, 6H); 2.42–2.32 (m, 5H); 2.15 (bs, 1H); 1.97 (s, 3H); 1.77–1.64 (m, 2H); 1.58 (s, 3H); 1.13 (s, 9H); 1.15–1.07 (m, 6H).

¹³C NMR (d₆-acetone, D₂O, 75.6 MHz): δ171.6, 166.9, 156.6, 141.8, 135.1, 134.2, 131.0, 130.7,129.4, 129.3, 128.4, 128.1, 88.3, 85.4, 81.9, 79.7, 78.6, 78.1, 76.8, 76.0, 74.8, 71.9, 71.2, 47.4, 44.0, 37.1, 36.3, 28.5, 27.0, 23.1, 22.0, 14.7, 10.4.

HRMS: MNa⁺, 940.3142 (Calculated for C₄₄H₅₆NO₁₈PNa=940.3133)

Example 10

2'-O-Phosphonooxymethoxymethylpaclitaxel (a) Preparation of 2'-O-(methylthiomethoxymethyl)-7-O-triethysilylpaclitaxel

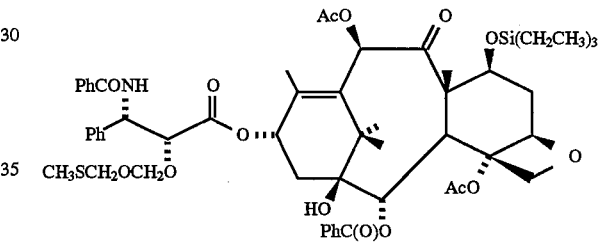

To a solution of 7-O-triethylsilylpaclitaxel (70.0 mg, 72.2 mmol), bis(methylthiomethyl)ether (90 mg, 72.2 mmol), molecular seives (70 mg), and N-iodosuccinimide (160 mg, 72.2 mmol) in THF (2.0 ml) at room temperature was added silver triflate (5.0 mg, 19.5 mmol) and the resulting solution was stirred for 2 h. The reaction mixture was then diluted with ethyl acetate and filtered through a pad of celite. The filtrate was washed with saturated aqueous sodium bicarbonate solution, followed by a 1:1 (v:v) mixture of saturated aqueous sodium bicarbonate and 5% aqueous sodium thiosulfate solution and finally brine. The organics were then dried over sodium sulfate and concentrated in vacuo. The residual oil was purified via flash chromatography (3:1, hexanes:ethyl acetate) to provide 22.0 mg (29%) of the title compound as a white solid:

¹H NMR (300 MHz, CDCl₃) δ8.12–7.20 (15H, m), 7.04 (1H, d, J=8.9 Hz), 6.41 (1H, s), 6.25 (1H, m), 5.81 (1H, dd, J=8.9, 2.4 Hz), 5.68 (1H, d, J=7.0 Hz), 4.93 (1H, d, 8.0 Hz), 4.79 (2H, m), 4.71 (1H, d, 2.4 Hz), 4.45 (1H, dd, J=10.5, 6.6 Hz), 4.30 (1H, d, J=8.3 Hz), 4.28 (1H, d, J=11.7 Hz), 4.17 (1H, d, J=8.3 Hz), 4.04 (1H, d, J=11.7 Hz), 3.80 (1H, d, J=6.9 Hz), 2.48–1.13 (25H, m, incl. singlets at 2.51, 2.13, 2.05, 2.01, 1.69, 1.19, 1.16), 0.98–0.85 (9H, m), 0.65–0.50 (6H, m).

(b) Preparation of 2'-O-(dibenzylphosphonooxymethoxymethyl)-7-triethylsilylpaclitaxel

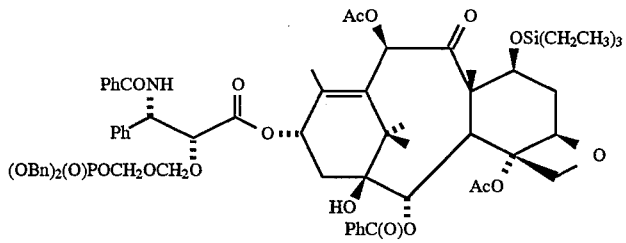

To a solution of the product obtained in step (a) (15 mg, 0.0141 mmol) and molecular sieves (15 mg) in THF (0.5 ml) at room temperature was added dibenzyl phosphate (20.0 mg, 0.089 mmol) followed by N-iodosuccinimide (4.2 mg, 0.0187 mmol) and the solution was stirred for 1 h. A TLC analysis of the reaction mixture at this time indicated the presence of starting material only. Silver triflate (5.0 mg, 0.019 mmol) was then added in three portions over 2 h and the reaction was stirred for an additional 1 h. The reaction mixture was then diluted with ethyl acetate and the resulting solution filtered through a pad of celite. The filtrate was treated with a 1:1 (v:v) solution of saturated aqueous sodium bicarbonate and 5% aqueous sodium thiosulfate solution. The organic extract was then washed with brine, dried over sodium sulfate and concentrated in vacuo. The residual oil was purified via flash chromatography (1:1, hexanes:ethyl acetate) to provide 5.0 mg (33%) of the title compound:

$^1$H NMR (300 MHz, CDCl$_3$) δ8.08–7.16 (25H, m), 7.18 (1H, d, J=8.8 Hz), 6.41 (1H, s), 6.21(1H, m), 5.82 (1H, dd, J=9.0, 3.1 Hz), 5.66 (1H, d, 7.0 Hz), 5.01–4.65 (10H, m), 4.56 (1H, dd, J=14.7, 5.6 Hz), 4.43(1H, dd, J=10.4, 6.7 Hz), 4.29 (1H, d, J=8.3 Hz), 4.16 (1H, d, J=8.3 Hz), 3.78 (1H, d, J=7.0 Hz), 2.60–1.13 (22H, m, incl. singlets at 2.49, 2.15, 1.93, 1.66, 1.15, 1.13, 3H each), 0.95–0.84 (9H, m), 0.63–0.45 (6H,m).

(c) Preparation of 2'-O-phosphonooxymethoxymethylpaclitaxel

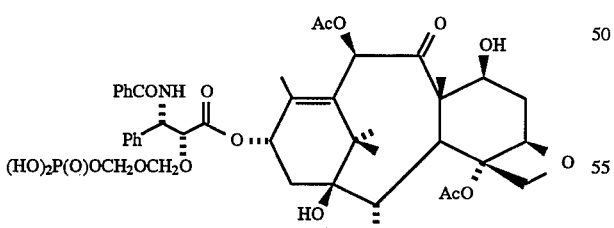

The product of step (b) is treated with tetrabutylammonium fluoride according to the procedure given in Example 9(f) to remove the 7-O-triethylsilyl protecting group. The compound thus obtained is subject to catalytic hydrogenation according to the procedure described in previous examples to provide the title compound.

Example 11

2'-O-Phosphonooxymethoxymethylpaclitaxel
(Alternate route)

(a) Preparation of 2'-O-triethylsilylpaclitaxel

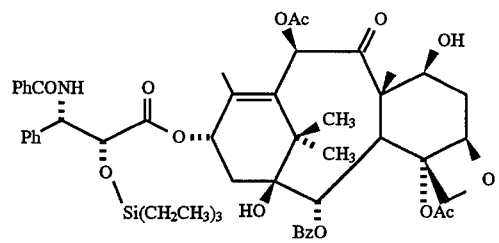

To a solution of paclitaxel (20.0 g, 0.0234 mol) and imidazole (3.59 g, 0.052 mol) in 150 mL of DMF (dimethylformamide) at 0° C. was added triethylsilyl chloride (6.0 mL, 0.053 mol) in 2.0 mL quantities over 20 min. The reaction mixture was then stirred at 0° C. for 1 h. The mixture was then diluted with ethyl acetate and saturated aqueous ammonium chloride. The organic layer was removed, washed with brine, dried over sodium sulfate and concentrated in vacuo to provide a yellow oil. Purification of the crude product via flash chromatography (hexanes:ethyl acetate: 1:3 then 1:1) provided 21.07 g (98% yield) of the desired title compound as a colorless white solid.

$^1$H-NMR (300 MHz, CDCl$_3$) δ8.15 (2H, m), 7.70 (2H, m), 7.65–7.30 (11H, m) 7.15 (1H, d, J=8.9 Hz), 6.30 (1H, s), 6.25 (1H, m), 6.70–6.10 (2H, m), 4.94 (1H, d, J=7.9 Hz), 4.67 (1$_{H'}$, d, 2.0 Hz), 4.40 (1H, m), 4.29 (1H, d, J=8.4 Hz), 4.18 (1H, d, J=8.4 Hz), 3.81 (1H, d, J=7.1 Hz), 2.65–1.10 (22H, including singlets at 2.55, 2.20, 1.88, 1.69, 1.22, 1.13, 3H each).

(b) Preparation of 2'-O-triethylsilyl-7-O-benzyloxycarbonylpaclitaxel

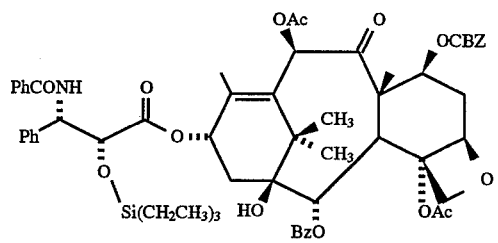

Butyllithium (1.6M in hexanes, 12.9 mL, 8.06 mmol) was added dropwise over 10 min to a solution of 2'-O- triethylsilylpaclitaxel (22.3 g, 24.1 mmol) in THF (250 mL) cooled to −50° C. The resulting solution was stirred for 20 min and the temperature maintained between −50° C. and −35° C. The reaction mixture was then cooled to −50° C. and benzyl chloroformate (5.08 mL, 29.8 mmol) was added dropwise over 5 min. The reaction mixture was maintained at −40° C. for 30 min then equilibrated to 0° C. over approximately 30 min. The mixture was then diluted with ethyl acetate and saturated aqueous ammonium chloride and the resulting organic layer washed with brine, dried over sodium sulfate and concentrated in vacuo. A $^1$H-NMR analysis of the crude reaction mixture showed the presence of desired 2'-O-triethylsilyl-7-O-benzyloxycarbonylpaclitaxel as well as 2'-O-triethylsilyl-7-epihydroxypaclitaxel (3:1 ratio, respectively). This product mixture was used in the next step without further purification and the isomers subsequently separated. An analytical sample of the major product 2'-O-triethylsilyl-7-O-benzyloxycarbonylpaclitaxel was purified via flash chromatography; $^1$H-NMR (300 MHz, CDCl$_3$) δ8.12 (2H, m), 7.72 (1H, m), 7.65–7.27 (1H, d, J=8.8 Hz), 6.41 (1H, m), 6.20 (1H, m), 5.72–5.65 (2H, m), 5.52 (1H, m), 5.24 (1H, d, J=12.3 Hz), 5.16 (1H, d, J=12.3 Hz), 4.95 (1H, d, J=8.7 Hz), 4.69 (1H, s), 4.35 (1H, d, J=8.3 Hz), 4.25 (1H, d, J=8.3 Hz), 3.94 (1H, d, J=6.8 Hz), 2.70–1.12 (22H, including singlets at 2.54, 2.14, 2.01, 1.80, 1.20, 1.15, 3H each), 0.81–0.73 (9H, m), 0.55–0.31 (6H, m).

(c) Preparation of 7-O-benzyloxycarbonylpaclitaxel

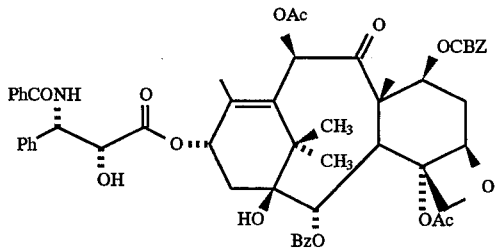

Hydrochloric acid (6N, 1.0 mL, 6.0 mmol) was added to a solution the product from Step (b) (24.0 g, 22.6 mmol) in acetonitrile (250 mL) cooled to 0° C. After 10 min a TLC analysis (hexanes:ethyl acetate, 1:1) indicated the reaction was complete. The reaction mixture was diluted with saturated aqueous sodium bicarbonate followed by ethyl acetate and the organic layer was removed, washed with brine, dried using sodium sulfate and concentrated in vacuo. The residual oil was purified using flash chromatography (hexanes:ethyl acetate, 1:3, then 1:1) to provide 11.4 g (48% over 2 steps) of the title compound and 4.8 g (20%) of 7-epihydroxypaclitaxel.

$^1$H-NMR (300 MHz, CDCl$_3$) δ8.09 (2H, m), 7.71 (2H, m), 7.65–7.27 (16H, m), 7.10 (1H, d, 8.9 Hz), 6.39 (1H, s), 6.16 (1H, m), 5.81 (1H, d, J=8.9, 2.4 Hz), 5.65 (1 H, d, J=6.9 Hz), 5.49 (1H, dd, J=10.6, 7.2 Hz), 5.20 (1H, d, J=11.9 Hz), 5.12 (1H, d, J=11.9), 4.91 (1H, d, J=8.4 Hz), 4.78 (1H, m), 4.30 (1H, d, J=8.4 Hz), 4.15 (1H, d, J=8.4 Hz), 3.91 (1H, d, J=6.8 Hz), 3.69 (1H, d, J=4.9 Hz), 2.65–1.10 (22H, including singlets at 2.39, 2.18, 1.81, 1.75, 1.21, 1.15, 3H each).

(d) Preparation of 2'-O-(methylthiomethoxymethyl)-7-O-benzyloxycarbonylpaclitaxel

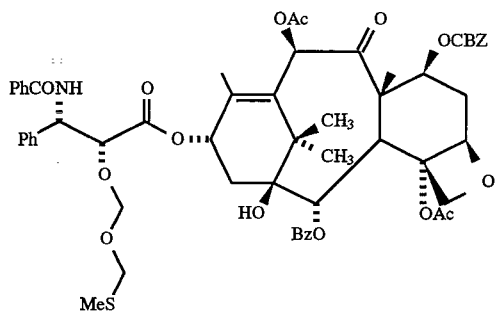

Silver triflate (300 mg, 1.17 mmol) was added to a solution 7-O-benzyloxycarbonylpaclitaxel (5.53 g, 5.71 mmol), 1, 1'-dithiomethyldimethyl ether (7.8 g, 57.1 mmol), N-iodosuccinimide (6.35 g, 28.3 mmol) and oven dried, powdered molecular sieves (5.0 g) in THF (110 mL) at room temperature. A TLC analysis (hexanes:ethyl acetate, 1:1) of the reaction mixture after 20 min indicated the conversion of approxiately 40% of the starting material to a higher running product. Silver triflate (150 mg, 0.585 mmol) was then added and the reaction was monitored by TLC which indicated after 30 min the reaction was appoximately 65% complete. The mixture was diluted with ethyl acetate (100 mL), filtered using a pad of celite and the filtrate was poured into a separatory funnel containing 200 mL of a saturated aqueous solution of sodium bicarbonate and 50 mL of a 5% aqueous sodium thiosulfate solution. The organic layer was removed, washed with brine, dried over sodium sulfate and concentrated in vacuo. The residual oil was purified via flash chromatography (hexanes:ethyl acetate, gradient elution 4:1 to 3:2) to provide 3.0 g (54% yield) of the title product as a light yellow solid.

$^1$H-NMR (300 MHz, CDCL$_3$) δ8.10 (2H, m), 7.74 (2H, m), 7.66–7.25 (18H, m), 7.05 (1H, d, J=8.9 Hz), 6.40 (1H, s), 6.26 (1H, m), 5.77 (1H, dd, J=8.8, 2.5 Hz), 5.71 (1H, d, J=6.9 Hz), 5.51 (1H, dd, J=10.6, 7.1 Hz), 5.21 (1H, d, J=11.9 Hz), 5.14 (1 H, d, J=11.9 Hz), 4.92 (1H, m), 4.79 (2H, m), 4.68 (1H, d, J=2.5 Hz), 4.31 (1H, d, J=11.8 Hz), 4.30 (1H, d, J=8.5 Hz), 4.16 (1H, d, J=8.5 Hz), 4.10 (1H, d, J=11.8 Hz), 3.93 (1H, d, J=6.9 Hz), 2.65–1.10 (25H including singlets at 2.50, 2.15, 2.05, 1.74, 1.72, 1.20, 1.15, 3H each).

(e) Preparation of 2'-O-(dibenzylphosphonooxymethoxymethyl)-7-O-benzyloxycarbonylpaclitaxel

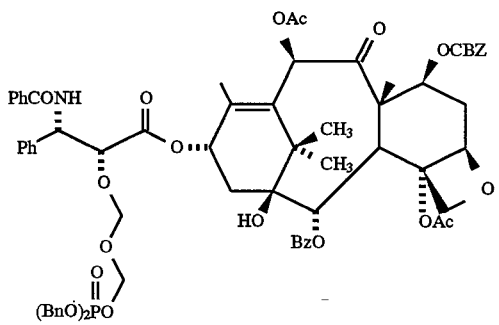

To a solution of 2'-O-(methylthiomethoxymethyl)-7-O-benzyloxycarbonylpaclitaxel (1.06 g, 1.07 mmol) and oven dried, powdered molecular sieves (1.0 g) in THF (20 mL) at room temperature was added dibenzyl phosphate (1.49 g, 5.30 mmol) followed immediately by N-iodosuccinimide (2.65 g, 1.18 mmol). A TLC analysis (hexanes:ethyl acetate 1:1) of the reaction mixture after 2.5 h indicated the reaction was approximately 60% complete. N-iodosuccinimide (175 mg, 0.78 mmol) was then added and the reaction stirred for an additional 30 min, after which time a TLC analysis indicated the reaction was complete. The reaction mixture was then diluted with ethyl acetate (50 mL) and filtered using a pad of celite. The filtrate was poured into a separatory funnel containing 100 mL of a saturated aqueous solution of sodium bicarbonate and 20 mL of a 5% aqueous solution of sodium thiosulfate. The organic layer was removed, washed with brine, dried over sodium sulfate and concentrated in vacuo. The residual oil was purified using flash chromatography (hexanes:ethyl acetate, gradient elution, 3:1 to 1:1) to provide 750 mg (62% yield) of the desired title compound as a white solid.

$^1$H-NMR (360 MHz, CDCl$_3$) δ8.10 (2H, m), 7.79 (2H, m), 7.65–7.24 (26H, m), 7.10 (1H,m), 6.41 (1H, s), 6.20 (1H,m), 5.79 (1H, dd, J=8.8, 3.6 Hz), 5.65 (1H, d, J=7.0 Hz), 5.52 (1H,m), 5.20 (1H, d, J=11.8 Hz), 5.11 (1H, d, J=11.8 Hz), 5.04–4.85 (6H, m), 4.75–4.60 (4H, m), 4.30 (1H, d, 8.4 Hz), 4.15 (1H, d,J=8.4 Hz), 3.92 (1H, d, J=7.0 Hz) 2.65–1.10 (22H including singlets at 2.48, 2.19, 1.95, 1.80, 1.20, 1.10, 3H each).

(f) Preparation of 2'-O-phosphonooxymethoxymethylpaclitaxel triethanolamine salt Palladium (10%) on carbon was added to a solution of 2'-O-(dibenzylphosphonooxymethoxymethyl)-7-O-benzyloxycarbonylpaclitaxel (500 mg, 0.382 mmol) in ethly acetate (40 mL) housed in a Parr bottle. The vessel was affixed to a Parr apparatus and the reaction mixture subjected to hydrogen at 50 psi. The reaction mixture was shaken for 6.5 h, then filtered using a sintered glass funnel. Triethanolamine (0.1N in ethyl acetate, 4.0 mL) was added to this filtrate and the resulting solution was concentrated in vacuo. The crude solid was suspended in approximately 5.0 mL of ethyl acetate and the solvent decanted. This process was repeated three times and the resulting title triethanolamine salt (300 mg) was obtained with purity of 87% as determined by HPLC analysis. Further purification of this compound via C18 chromatography (water:acetonitrile, 3:1) provided the desired title compound (120 mg, 34%) at 95% purity by HPLC.

$^1$H-NMR (300 MHz, CD$_3$COCD$_3$, D$_2$O) δ9.05 (1H, d, J=8.7 Hz), 8.15–7.12 (21H, m), 6.40 (1H,m), 6.05 (1H, m), 5.69–5.55 (2H, m), 5.01–4.85 (6H, m), 4.35 (1H, m), 4.14 (2H, m), 3.96–3.85 (6H, m), 3.25 (1H, d, J=7.1 Hz), 3.30–3.15 (6H, m) 2.50–1.04 (22H, including singlets at 2.49, 2.15, 2.05, 1.81, 1.60, 3H each).

Example 12

3'-N-debenzoyl-3'-N-(isopropyloxycarbonyl)-7-O-methylthiomethylpaclitaxel

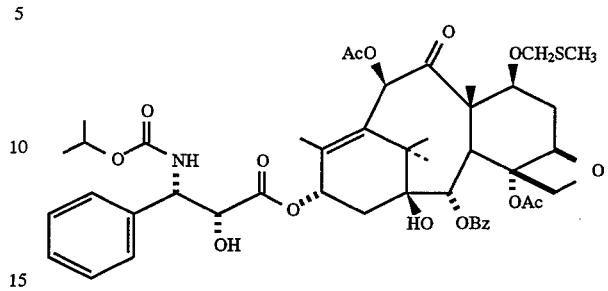

To a solution of 7-O-methylthiomethylbaccatin III (408 mg, 0.630 mmol) in 10 mL of THF at –60° C. was added nBuLi (0.30 mL, 2.5M, 0.75 mmol) and stirred for 10 min. (3R, 4S)-3-Triethylsilyloxy-4-phenyl-N-isopropyloxycarbonylazetidin-2-one (320 mg, 0.88 mmol) in 6 mL of THF was added dropwise and then the reaction brought to 0° C. for 30 min. The solution was quenched with saturated NH$_4$Cl and extracted with ethyl acetate, shaken with Bu$_4$NF (1.0 mL, 1.0M, 1.0 mmol) and then washed with brine, dried over MgSO$_4$ and concentrated. The residue was chromatographed over silica gel (1.5:1 hexane/ethyl acetate) to give 545 mg of a product which was crystalized from acetone/hexane to give 476 mg of the title product as a white solid (84%); IR(KBr) 3460, 1720, 1266, 1244, 1230 cm$^{-1}$; $^1$H-NMR (CDCl$_3$, 300 MHz) δ8.07 (d, J=7.2 Hz, 2H), 7.59 (t, J=7.2 Hz, 1H), 7.47 (t, J=7.5 Hz, 2H), 7.32 (m, 5H), 6.51 (s, 1H), 6.18 (t, J=8.7 Hz, 1H), 5.65 (d, J=6.6 Hz, 1H), 5.50 (d, J=9.3 Hz, 1H), 5.28 (d J=8.4 Hz, 1H), 4.91 (d, J=8.1 Hz, 1H), 4.77 (m, 1H), 4.64 (bs, 3H), 4.26 (m, 2H), 4.15 (d, J=8.4 Hz, 1H), 3.83 (d, J=6.9 Hz, 1H), 3.44 (d, J=5.1 Hz, 1H), 2.78 (m, 1H), 2.34 (s, 3H), 2.25 (d, J=9.0 Hz, 2H), 2.17 (s, 3H), 2.14 (s, 1H), 2.10 (s, 3H), 1.96 (s, 3H), 1.83 (m, 1H), 1.73 (s, 3H), 1.15 (m, 12H); $^{13}$C NMR (CDCl$_3$, 75.5 Hz) δ201.8, 170.4, 169.2, 167.0, 156.3, 140.1, 138.3, 133.7, 133.3, 130.2, 129.1, 128.8, 128.6, 128.1, 126.8, 83.8, 81.4, 78.7, 76.0, 75.5, 74.5, 74.0, 73.6, 72.2, 68.9, 57.5, 56.4, 47.1, 43.2, 35.3, 32.9, 26.6, 22.6, 22.0, 21.9, 20.9, 15.1, 14.6, 10.9

FABMS (NOBA) M+Na calcd for C$_{46}$H$_{57}$NSO$_{15}$: 918. Found: 918.

Anal. calcd for C$_{46}$H$_{57}$NSO$_{15}$: C, 61.66; H, 6.41; N, 1.56. Found: C, 61.63; H, 6.36; N, 1.68.

Example 13

3'-N-Debenzoyl-3'-N-(n-butyloxycarbonyl)-7-O-methylthiomethylpaclitaxel

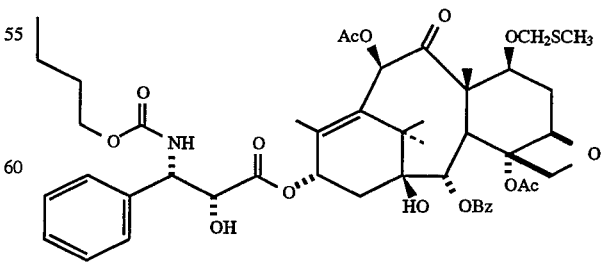

To a solution of 7-O-methylthiomethylbaccatin III (425 mg, 0.66 mmol) in 10 mL of THF at –60° C. was added nBuLi (0.30 mL, 2.5M, 0.75 mmol) and stirred for 10 min. (3R,4S)-3-Triethylsilyloxy-4-phenyl-N-(n-butyloxycarbonyl)azetidin-2-one (350 mg, 0.93 mmol) in 6 mL of THF was added dropwise and then the reaction brought to 0° C. for 30 min. The solution was quenched with saturated NH$_4$Cl and extracted with ethyl acetate, shaken with Bu$_4$NF (1.0 mL, 1.0M, 1.0 mmol) and then washed with brine, dried over MgSO$_4$ and concentrated. The residue was chromatographed over silica gel (1.5:1 hexane/ethyl acetate) to give 581 mg of the title product which was crystalized from toluene/hexane to give 464 mg of a white solid (77%); IR(KBr) 3444, 1722, 1372, 1242, 1108, 1066, 1026, 988 cm$^{-1}$; $^1$H-NMR (CDCl$_3$, 300 MHz) δ8.08 (d, J=7.2 Hz, 2H), 7.59 (t, J=7.5 Hz, 1H), 7.47 (t, J=7.2 Hz, 2H), 7.39–7.11 (m, 5H), 6.51 (s, 1H), 6.20 (t, J=8.7 Hz, 1H), 5.65 (d, J=6.9 Hz, 1H), 5.56 (d, J=9.3 Hz, 1H), 5.29 (d J=8.4 Hz, 1H), 4.91 (d, J=8.1 Hz, 1H), 4.65 (bs, 3H), 4.27 (m, 2H), 4.15 (d, J=8.4 Hz, 1H), 3.97 (m, 2H), 3.84 (d, J=6.9 Hz, 1H), 3.45 (d, J=4.8 Hz, 1H), 2.78 (m, 1H), 2.33 (s, 6H), 2.25 (d, J=8.7 Hz, 2H), 2.17 (s, 3H), 2.10 (s, 3H), 1.96 (s, 3H), 1.83 (m, 1H), 1.74 (s, 3H), 1.62 (s, 1H), 1.48 (m, 2H), 1.19 (m, 5H), 0.83 (t, J=7.2 Hz, 3H); $^{13}$C NMR (CDCl$_3$, 75.5 Hz) δ 201.9, 172.3, 170.5, 169.2, 167.0, 156.3, 140.1, 138.4, 133.8, 133.4, 130.2, 129.2, 129.0, 128.9, 128.7, 128.2, 126.8, 125.3, 83.9, 81.4, 78.8, 77.3, 76.0, 75.6, 74.6, 74.1, 73.7, 72.2, 65.4, 57.5, 56.5, 47.2, 43.2, 35.4, 26.6, 22.6, 21.5, 21.0, 18.9, 15.1, 14.7, 13.7, 10.9.

FABMS (NOBA) M+H calcd for C$_{47}$H$_{60}$NSO$_{15}$: 910. Found: 910.

Anal. calcd for C$_{47}$H$_{59}$NSO$_{15}$: C, 62.03; H, 6.53; N, 1.54. Found: C, 62.16; H, 6.45; N, 1.57.

Example 14

3'-N-debenzoyl-3'-N-(t-butoxycarbonyl)-7-O-methythiomethylpaclitaxel (a) Preparation of 3'-N-debenzoyl-3'-N-(t-butoxycarbonyl)-2-O-triethylsilyl-7-O-methylthiomethylpaclitaxel

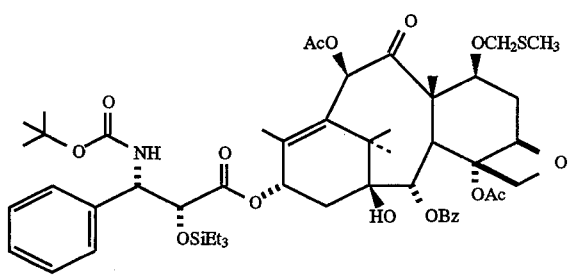

To a solution of HMDS (0.275 mL, 1.30 mmol) in 8 mL of THF was added a solution of n-BuLi (0.48 mL, 2.5 M in hexanes, 1.20 mmol) and stirred 5 minutes at −55° C. To this solution was added methylthiomethylbaccatin III (639 mg, 0.99 mmol) in 8 mL of THF and stirred for 10 minutes before addition of an 8 mL solution of (3R,4S)-3-triethylsilyloxy-4-phenyl-N-(t-butoxycarbonyl)azetidin-2-one (575 mg, 1.52 mmol). The cold bath was removed and replaced with a 0° C. bath and the reaction stirred for 30 minutes. The solution was diluted with ethyl acetate and washed with saturated NH$_4$Cl solution, dried over MgSO$_4$ and concentrated. The residue was chromatographed over silica gel (3:1 hexane/ethyl acetate) to give 1.0 g of the title product (98%); $^1$H-NMR (CDCl$_3$, 300 MHz) δ8.09 (d, J=6.9 Hz, 2H), 7.57 (m, 1H), 7.46 (t, J=7.8 Hz, 2H), 7.35 (m, 2H), 7.26 (m, 3H), 6.55 (s, 1H), 6.25 (t, J=9.6 Hz, 1H), 5.68 (d, J=6.9 Hz, 1H), 5.45 (bd, J=9.3 Hz, 1H), 5.27 (bd, 1H), 4.95 (d, J=7.8 Hz, 1H), 4.65 (s, 2H), 4.53 (s, 1H), 4.29 (m, 2H), 4.17 (d, J=8.4 Hz, 1H), 3.89 (d, J=6.9 Hz, 1H), 2.81 (m, 1H), 2.51 (s, 3H), 2.37 (dd, J=15.3, 9.6 Hz, 1H), 2.17 (S, 3H), 2.10 (S, 3H), 2.03 (s, 3H), 1.85 (m, 1H), 1.74 (s, 3H), 1.63 (d, J=14.1 Hz, 1H), 1.29 (s, 9H), 1.21 (s, 6H), 0.76 (t, J=7.8 Hz, 9H), 0.36 (m, 6H); $^{13}$C-NMR (CDCl$_3$, 75.5 Hz) δ202.0, 171.6, 170.1, 169.3, 167.1, 155.2, 141.0, 139.0, 133.6, 132.8, 130.2, 129.2, 128.7, 128.5, 127.7, 126.4, 83.9, 81.2, 79.9, 78.9, 76.0, 75.7, 75.2, 74.8, 74.2, 71.3, 57.3, 56.7, 47.0, 43.3, 35.3, 33.0, 28.2, 26.4, 23.0, 21.5, 21.0, 15.0, 14.4, 10.9, 6.5, 4.3; IR(film) 3448 (s), 1720, 1242, 1120, 1056 cm$^{-1}$.

FABMS (NOBA) M+H calcd for C$_{53}$H$_{74}$NSSiO$_{15}$: 1024.4549. Found: 1024.4583.

(b) Preparation of 3'-N-debenzoyl-3'-N-(t-butoxycarbonyl)-7-O-methylthiomethylpaclitaxel

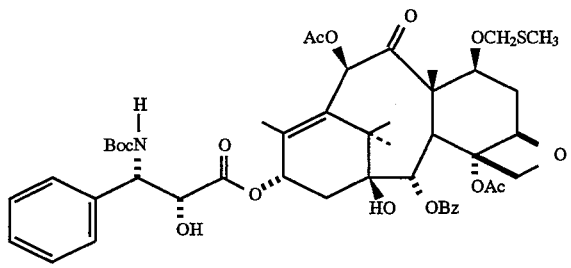

To a solution of the 3'-N-debenzoyl-3'-N-(t-butoxycarbonyl)-2-O-triethylsilyl-7-O-methylthiomethylpaclitaxel (269 mg, 0.26 mmol) in 6 mL of THF was added tetrabutylammonium fluoride (0.3 mL, 1.0M in THF, 0.3 mmol) and stirred 10 minutes. The solution was diluted with ethyl acetate and washed with brine, dried over MgSO$_4$ and concentrated and the residue was chromatographed over silica gel (1:1 hexane/ethyl acetate) to give 240 mg of the title product (95%); IR(film) 3440, 1720, 1370, 1242, 1170, 1108, 1066, 756 cm$^{-1}$; $^1$H-NMR (CDCl$_3$, 300 MHz) δ8.06 (d, J=7.2 Hz, 2H), 7.57 (t, J=7.2 Hz, 1H), 7.46 (t, J=7.8 Hz, 2H), 7.35 (m, 5H), 6.52 (s, 1H), 6.16 (t, J=8.7 Hz,1H), 5.64 (d, J=6.9 Hz, 1H), 5.43 (bd, J=9.3 Hz, 1H), 5.24 (bd, J=8.1 Hz, 1H), 4.91 (d, J=8.1 Hz, 1H), 4.63 (m, 3H), 4.26 (m, 2H), 4.14 (d, J=8.4 Hz, 1H), 3.83 (d, J=6.9 Hz, 1H), 3.46 (d, J=5.4 Hz, 1H), 2.77 (m, 1H), 2.34 (s, 3H), 2.27 (d, J=8.7 Hz, 2H), 2.16 (s, 3H), 2.09 (s, 3H), 1.97 (s, 3H), 1.79 (m, 2H), 1.72 (s, 3H), 1.32 (s, 9H), 1.19 (s, 3H), 1.18 (s, 3H); $^{13}$C-NMR (CDCl$_3$, 75.5 Hz) δ202.0, 172.7, 170.3, 169.2, 167.0, 155.3, 140.3, 138.4, 133.7, 133.2, 130.2, 129.1, 128.8, 128.7, 128.0, 126.7, 83.9, 81.3, 80.2, 78.6, 76.5, 76.1, 75.7, 75.4, 74.6, 74.0, 73.6, 72.3, 57.4, 56.1, 47.1, 43.2, 35.3, 32.8, 28.2, 26.5, 22.6, 21.0, 15.1, 14.6, 10.9.

FABMS (NOBA) M+H calcd for C$_{47}$H$_{60}$NO$_{15}$S: 910.3684. Found: 910.3706.

Example 15

3,-N-debenzoyl-3'-N-(t-butoxycarbonyl)-2'-O-ethyloxycarbonyl-7-O-methylthiomethylpaclitaxel

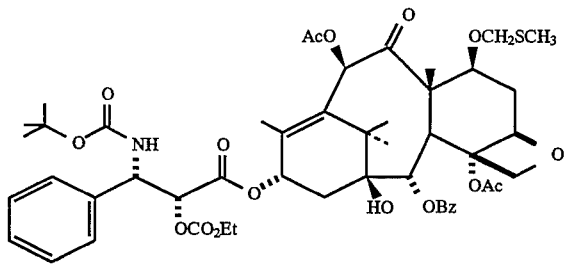

To a solution of 3'-N-debenzoyl-3'-N-(t-butoxycarbonyl)-7-O-methylthiomethylpaclitaxel (428 mg, 0.47 mmol) in 10 mL of dichloromethane was added diisopropylethyl amine (0.85 mL, 4.8 mmol) and DMAP (20 mg) and cooled to 0° C. The ethyl chloroformate (0.25 mL, 2.6 mmol) was then added and stirred for 1 hr. The solution was diluted with ethyl acetate and washed with bicarbonate and brine, dried (MgSO$_4$) and concentrated. The residue so obtained was chromatographed over silica gel (1:1 hexane/ethyl acetate) to give 428 mg of the title ethyl carbonate (92%); IR(film) 3448 (w), 1750, 1720, 1370, 1244, 1064 cm$^{-1}$; $^1$H-NMR (CDCl$_3$, 300 MHz) δ8.09 (d, J=7.2 Hz, 2H), 7.59 (t, J=7.2 Hz, 1H), 7.48 (t, J=7.8 Hz, 2H), 7.39 (m, 2H), 7.31 (m, 3H), 6.55 (s, 1H), 6.25 (t, J=9.0 Hz, 1H), 5.68 (d, J=7.2 Hz, 1H), 5.40 (bm, 2H), 5.25 (s, 1H), 4.95 (d, J=8.1 Hz, 1H), 4.65 (S, 2H), 4.29 (m, 2H), 4.15 (m, 3H), 3.88 (d, J=6.9 Hz, 1H), 2.81 (m, 1H), 2.43 (s, 3H), 2.32 (m, 1H), 2.21 (m, 1H), 2.16 (s, 3H), 2.11 (s, 3H), 2.08 (s, 3H), 1.84 (m, 1H), 1.74 (s, 3H), 1.62 (s, 1H), 1.32 (s, 9H), 1.28 (t, J=7.2 Hz, 3H), 1.20 (s, 6H); $^{13}$C-NMR (CDCl$_3$, 75.5 Hz) δ202.0, 169.7, 169.1, 168.1, 167.0, 155.1, 154.1, 141.0, 137.2, 133.6, 132.9, 130.2., 129.2, 128.9, 128.7, 128.2, 126.4, 83.9, 81.2, 80.4, 78.9, 76.5, 76.0, 75.8, 74.8, 74.2, 72.0, 65.1, 57.4, 47.1, 43.3, 35.1, 33.0, 28.1, 26.4, 22.7, 21.3, 20.9, 15.0, 14.5, 14.1, 10.9.

FABMS (NOBA) M+H calcd for C$_{50}$H$_{64}$NSO$_{17}$: 982.3895. Found: 982.3874.

Example 16

3'-N-Debenzoyl-3'-N-(t-butoxycarbonyl)-7-O-methylthiomethyl-10-deacetyl-10-hydroxymethylcarbonyl(paclitaxel)

(a) Preparation of 7-O-Triethylsilyl-10-deacetyl-10-benzyloxymethylcarbonyl baccatin III

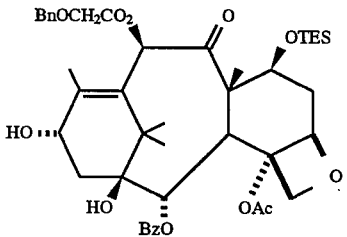

To a solution of 7-O-triethylsilyl-10-deacetylbaccatin III (3.85 g, 5.85 mmol) in 40 mL of THF at –60° C. was added n-BuLi (2.6 mL, 2.5M in hexanes, 6.5 mmol) and stirred for 5 min before addition of benzyloxyacetyl chloride (1.0 mL, 6.5 mmol). After stirring for 30 min at –60° C. and then warming to ambient temperature the solution was diluted with ethyl acetate and washed with bicarbonate. The solution was dried over MgSO$_4$ and concentrated and the residue chromatographed over silica gel (2:1 then 1:1 hexane/ethyl acetate) to give 4.36 g of product (92%); IR(film) 3478 (br), 1724, 1270, 1244, 1136, 1110, 1070 cm$^{-1}$; $^1$H-NMR (CDCl$_3$, 300 MHz) δ8.08 (d, J=7.2 Hz, 2H), 7.60–7.23 (m, 8H), 6.54 (s, 1H), 5.60 (d, J=6.9 Hz, 1H), 4.94 (d, J=7.8 Hz, 1H), 4.79 (bq, 1H), 4.69 (s, 2H), 4.49 (dd, J=10.5, 6.6 Hz, 1H), 4.26 (m, 2H), 4.12 (m, 1H), 3.85 (d, J=6.9 Hz, 1H), 2.52 (m, 1H), 2.26 (s, 3H), 2.23 (m, 2H), 2.18 (s, 3H), 2.10 (m, 1H), 1.86 (m, 1H), 1.66 (s, 3H), 1.14 (s, 3H), 0.99 (s, 3H), 0.91 (t, J=7.5 Hz, 9H), 0.56 (m, 6H).

Anal. Calcd. for C$_{44}$H$_{58}$SiO$_{12}$: C, 65.49; H, 7.24. Found: C, 65.33; H, 7.27.

FABMS (NOBA) M+H calcd for C$_{44}$H$_5$SiO$_{12}$ 807. Found: 807.

(b) 3'-N-debenzoyl-3'-N-(t-butoxycarbonyl)-10-deacetyl-10-benzyloxymethylcarbonyl(paclitaxel)

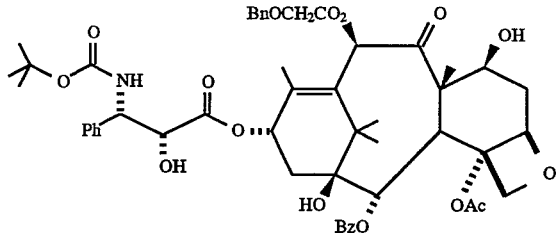

To a solution of 7-O-triethylsilyl-10-deacetyl-10-benzyloxymethylcarbonyl baccatin III (1.21 g, 1.66 mmol) in 50 mL of THF at –60° C. was added n-BuLi (0.7 mL, 2.5M in hexanes, 1.75 mmol) and stirred for 5 min before addition of (3R,4S)-3-triethylsilyloxy-4-phenyl-N-(t-butoxycarbonyl)azetidin-2-one (1.2 g, 3.2 mmol). After stirring for 5 min at –60° C. and then 30 min at 0° C. the solution was diluted with ethyl acetate and washed with saturated NH$_4$Cl. The solution was dried over MgSO$_4$ and concentrated and the residue chromatographed over silica gel (3:1 then 1:1 hexane/ethyl acetate) to give 980 mg of product (53%). This product was dissolved in 6 mL of acetonitrile and cooled to 0° C. and stirred with 0.60 mL of 6N HCl for 19 hrs. The solution was diluted with ethyl acetate and washed with saturated bicarbonate, dried over MgSO$_4$ and chromatographed over silica gel (1:1 hexane/ethyl acetate) to give 570 mg of product (35%); IR(film) 3448 (br), 1716, 1496, 1368, 1316, 1270, 1246, 1176, 1108, 1070, 1026 cm$^{-1}$; $^1$H-NMR (CDCl$_3$, 300 MHz) δ8.08 (d, J=7.5 Hz, 2H), 7.59 (t, J=7.8 Hz, 1H), 7.47 (t, J=7.8 Hz, 2H), 7.36 (m, 10H), 6.38 (s, 1H), 6.20 (t, J=9.0 Hz, 1H), 5.65 (d, J=6.9 Hz, 1H), 5.39 (bd, J=9.3 Hz, 1H), 4.93 (d, J=7.8 Hz, 1H), 4.69 (s, 2H), 4.60 (bs, 1H), 4.39 (m, 1H), 4.28 (m, 3H), 4.15 (d, J=8.4 Hz, 1H), 3.78 (d, J=6.9 Hz, 1H), 3.40 (bs, 1H), 2.54 (m, 1H), 2.43 (m, 1H), 2.36 (s, 3H), 2.28 (m, 2H), 1.84 (s, 4H), 1.72 (m, 1H), 1.67 (s, 3H), 1.31 (s, 9H), 1.23 (m, 1H), 1.21 (s, 3H), 1.10 (s, 3H).

Anal. Calcd. for C$_{52}$H$_{61}$NO$_{16}$: C, 65.33; H, 6.43; N, 1.46. Found: C, 64.97; H, 6.44; N, 1.43.

FABMS (NOBA) M+Na calcd for C$_{52}$H$_{61}$NO$_{16}$Na 978. Found: 978.

(c) Preparation of 3'-N-debenzoyl-3'-N-(t-butoxycarbonyl)-2-O-benzyloxycarbonyl-7-O-methylthiomethyl-10-deacetyl-10-benzyloxymethylcarbonyl(paclitaxel)

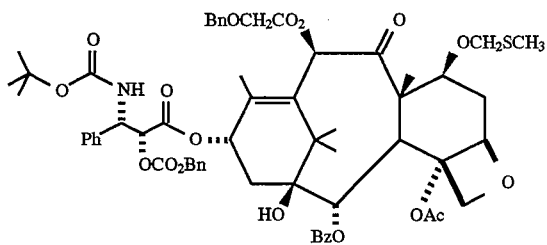

To a solution of 3'-N-debenzoyl-3'-N-(t-butoxycarbonyl)-10-deacetyl-10-benzyloxymethylcarbonyl(paclitaxel) (570 mg, 0.59 mmol) in 10 mL of $CH_2Cl_2$ at 0° C. was added diisopropylethyl amine (0.15 mL, 0.86 mmol) and CbzCl (0.10 mL, 0.70 mmol). The solution was stirred for 1 hr slowly warming to ambient temperature. The solution was washed with bicarbonate and dried over $MgSO_4$ and concentrated. The residue in 10 mL of acetonitrile at 0° C. was stirred with benzoyl peroxide (780 mg, 3.22 mmol) and dimethylsulfide (0.50 mL, 6.8 mmol) slowly warming to ambient temperature over 75 min. The solution was diluted with ethyl acetate and washed with saturated bicarbonate, dried over $MgSO_4$ and chromatographed over silica gel (2:1 hexane/ethyl acetate) to give 412 mg of the title product (65%);

IR(film) 3438, 1754, 1722, 1368, 1272, 1244, 1176, 1110, 1066, 1028 $cm^{-1}$; $^1$H-NMR ($CDCl_3$, 300 MHz) $\delta$8.11 (d, J=7.2 Hz, 2H), 7.61 (t, J=7.2 Hz, 1H), 7.49 (t, J=7.8 Hz, 2H), 7.35 (m, 15H), 6.67 (s, 1H), 6.26 (t, J=8.7 Hz, 1H), 5.69 (d, J=6.6 Hz, 1H), 5.41 (bm, 2H), 5.29 (s, 1H), 5.14 (ABq, J=12, 5.7 Hz, 2H), 4.98 (d, J=8 Hz, 1H), 4.72 (m, 4H), 4.32 (m, 3H), 4.19 (m, 2H), 3.90 (d, J=6.0 Hz, 1H), 2.85 (m, 1H), , 2.45 (m, 1H), 2.44 (s, 3H), 2.34 (m, 1H), 2.24 (m, 1H), 2.15 (s, 3H), 2.12 (s, 3H), 1.87 (m, 1H), 1.77 (s, 3H), 1.33 (s, 9H), 1.19 (s, 6H); $^{13}$C NMR ($CDCl_3$, 75.5 MHz) $\delta$ 201.6, 169.7, 168.7, 168.0, 167.0, 155.1, 154.1, 141.6, 137.1, 134.4, 133.7, 132.5, 130.2, 129.2, 128.9, 128.8, 128.7, 128.5, 128.4, 128.2, 128.0, 128.0, 126.4, 83.9, 81.2, 80.4, 78.8, 77.2, 76.2, 75.8, 74.7, 74.3, 73.4, 72.0, 70.6, 67.1, 57.4, 54.1, 47.1, 43.2, 35.2, 32.9, 28.1, 26.4, 22.7, 21.3, 15.2, 14.6, 10.9.

FABMS (NOBA) M+Na calcd for $C_{62}H_{71}NO_{18}SNa$ 1172. Found: 1172.

(d) Preparation of 3'-N-debenzoyl-3'-N-(t-butoxycarbonyl)-7-O-methylthiomethyl-10-deacetyl-10-hydroxymethylcarbonyl(paclitaxel)

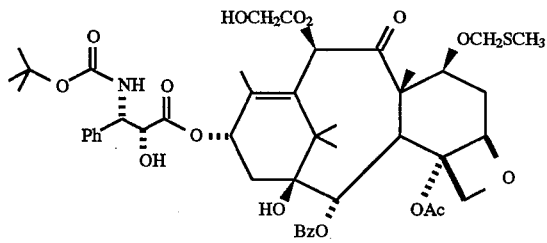

To a solution of 3'-N-debenzoyl-3'-N-(t-butoxycarbonyl)-2-O-benzyloxymethylcarbonyl-7-O-methylthiomethyl-10-deacetyl-10-benzyloxycarbonyl(paclitaxel) (377 mg, 0.35 mmol) in 30 mL of ethanol was added a total of 450 mg of 10% palladium on carbon catalyst and stirred under an atmosphere of hydrogen for 120 hrs. The catalyst was removed by filtration through celite and the solution concentrated. The residue was chromatographed over silica gel (20% $CH_3CN$/79% $CH_2Cl_2$/1% MeOH) to give 190 mg of the title product (65%); IR(film) 3444 (br), 1724, 1368, 1246, 1174, 1096, 1070, 1026, 988 $cm^{-1}$; $^1$H NMR ($CDCl_3$, 300 MHz) $\delta$8.07 (d, J=7.2 Hz, 2H), 7.59 (t, J=7.2 Hz, 1H), 7.47 (t, J=7.8 Hz, 2H), 7.35 (m, 5H), 6.65 (s, 1H), 6.17 (t, J=8.7 Hz, 1H), 5.65 (d, J=6.6 Hz, 1H), 5.39 (bd, J=9.6 Hz, 1H), 5.26 (bd, 1H), 4.93 (d, J=8.4 Hz, 1H), 4.67 (m, 3H), 4.28 (m, 5H), 3.83 (d, J=6.0 Hz, 1H), 3.44 (d, J=5.1 Hz, 1H), 2.77 (m, 1H), , 2.50 (m, 1H), 2.36 (s, 3H), 2.29 (d, J=8.4 Hz, 2H), 2.13 (bs, 3H), 2.01 (s, 3H), 1.82 (m, 2H), 1.74 (s, 3H), 1.33 (s, 9H), 1.18 (s, 3H), 1.16 (s, 3H); $^{13}$C NMR ($CDCl_3$, 75.5 MHz) $\delta$201.5, 171.7, 170.3, 167.0, 155.4, 141.3, 133.7, 132.7, 130.2, 129.0, 128.8, 128.7, 128.1, 126.8, 83.8, 81.3, 80.2, 78.6, 75.0, 74.4, 74.0, 73.6, 72.3, 60.6, 57.4, 56.2, 47.2, 43.2, 35.3, 32.6, 28.2, 26.5, 22.6, 21.0, 15.5, 14.7, 10.8.

FABMS (NOBA) M+Na calcd for $C_{47}H_{59}NO_{16}SNa$ 948. Found: 948.

Example 17

3'-N-debenzoyl-3'-N-(t-butoxycarbonyl)-7-O-methylthiomethyl-3'-desphenyl-3'-isobutenylpaclitaxel

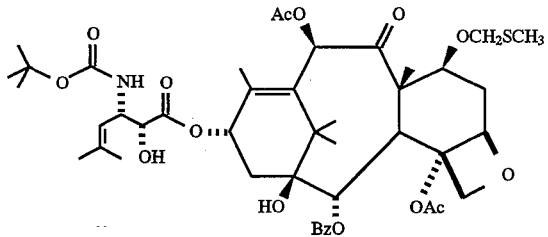

To a solution of 7-O-methylthiomethylbaccatin III (1.5 g, 2.3 mmol) in 30 mL of THF was added n-BuLi (1.0 mL, 2.5M in hexane, 2.5 mmol) at −60° C. and stirred for 10 minutes. Then a solution of (±)-cis-3-triethylsilyloxy-4-isobutenyl-N-t-butoxycarbonylazetidin-2-one (3.3 g, 9.3 mmol) in 10 mL of THF was added dropwise. The solution was then stirred at 0° C. for 30 min. and quenched with sat. $NH_4Cl$ solution and extracted with ethyl acetate. The solution was dried over $MgSO_4$ and concentrated and the residue chromatographed over silica gel (3:1 hexane/ethyl acetate). The product was dissolved in 100 mL of THF and was shaken with $Bu_4NF$ (2.3 mL, 1.0M in THF, 2.3 mmol) diluted with ethyl acetate and washed with brine. The solution was dried over $MgSO_4$ and concentrated and the residue chromatographed over silica gel (1.5:1 hexane/ethyl acetate) to give 1.6 g of the title product (78%); IR(film) 3452 (br), 1724, 1370, 1242, 1096, 1066 $cm^{-1}$; $^1$H-NMR ($CDCl_3$, 300 MHz) $\delta$ 8.07 (d, J=7.2 Hz, 2H), 7.59 (t, J=7.5 Hz, 1H), 7.45 (t, J=7.8 Hz, 2H), 6.54 (s, 1H), 6.11 (t, J=9.3 Hz, 1H), 5.66 (d, J=6.0 Hz, 1H), 5.29 (d, J=6.0 Hz, 1H), 4.94 (d, J=8.1 Hz, 1H), 4.75 (m, 2H), 4.64 (ABq, J=12.0, 2.7 Hz, 2H), 4.29 (m, 2H), 4.20 (m, 2H), 3.86 (d, J=6.0 Hz, 1H), 3.37 (bd, 1H), 2.79 (m, 1H), 2.35 (s, 6H), 2.16 (s, 3H), 2.10 (s, 3H), 2.04 (s, 3H), 1.82 (m, 1H), 1.74 (s, 9H), 1.34 (s, 9H), 1.23 (s, 3H), 1.20 (s, 3H); $^{13}$C NMR ($CDCl_3$, 75.5 Hz) $\delta$202, 170.2, 169.2, 166.9, 155.4, 140.6, 138.0, 133.7, 133.1, 130.1, 129.2, 128.6, 120.6, 83.8, 81.2, 79.9, 78.7, 77.2, 76.1, 75.5, 74.6, 74.0, 73.7, 72.2, 57.4, 51.5, 47.1, 43.2, 35.4, 32.9, 28.2, 26.4, 25.8, 22.4, 21.0, 18.6, 15.1, 14.8, 10.9.

FABMS (NOBA) M+H calcd for $C_{45}H_{62}NSO_{15}$ 888. Found: 888.

Example 18

7-O-methylthiomethyl-3'-desphenyl-3'-isobutenylpaclitaxel

The title compound was prepared as in Example 17 from 7-O-methylthiomethylbaccatin III and (±)-cis-3-triethylsilyloxy-4-isobutenyl-N-benzoylazetidin-2-one.

Example 19

3'-Desphenyl-3'-(2-furyl)-2'-O-ethyloxycarbonyl-7-O-methylthiomethylpaclitaxel

The title compound can be prepared from (3R,4R)-1-benzoyl-4-(2-furyl)-3-triethylsilyloxy-2-azetidinone and 7-O-methylthiomethylbaccatin III following the procedures decribed in Examples 7(a) and 7(b).

Example 20

2'-O-n-propylcarbonyl-7-O-phosphonooxymethylpaclitaxel (a) Preparation of 2'-O-n-propylcarbonylpaclitaxel

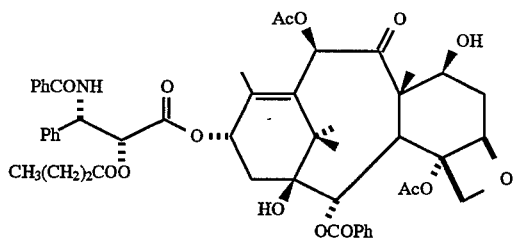

To a solution of paclitaxel (15.0 g, 17.5 mmol) and diisopropylethyl amine (18.3 mL, 105 mmol) in dichloromethane (175 mL) cooled to 0° C. was added butyryl chloride (5.49 mL, 52.4 mmol) dropwise over 2 min. The reaction mixture was then warmed to room temperature and stirred for 16h. The reaction mixture was then partitioned between ethyl acetate and a saturated aqueous ammonium chloride solution. The organic phase was then washed with a saturated sodium bicarbonate solution followed by brine, dried over sodium sulfate and concentrated in vacuo. The residual oil was purified using flash chromatography (eluted with hexanes:ethyl acetate) to provide the title ester (15.9 g, 98% yield) as a white solid; $^1$H-NMR (CDCl$_3$, 300 MHz) δ8.13–8.05 (2H, m), 7.75–7.65 (2H, m), 7.62–7.30 (11H, m), 6.88 (1H, d, J=9.0 Hz), 6.26 (1H, s), 6.23 (1H, dd, J=8.4 Hz), 5.92 (1H, dd, J=9.3, 6.0 Hz), 5.65 (1H, d, J=7.1 Hz), 5.48 (1H, d, J=3.2 Hz), 4.94 (1H, d, J=7.9 Hz), 4.21 (1H, dd, J=10.4, 6.5 Hz), 4.28 (1H, d, J=8.4 Hz), 4.17 (1H, d, J=8.4 Hz), 3.78 (1H, d, J=7.0 Hz), 2.64–1.02 (26H, m, including singlets at 2.43, 2.19, 1.91, 1.65, 1.65, 1.20, 1.10, 3H each), 0.87 (3H, dd, J=8.2 Hz).

(b) Preparation of 2'-O-n-propylcarbonyl-7-O-methylthiomethylpaclitaxel

To a solution of 2'-O-n-propylcarbonylpaclitaxel (14.4 g, 15.6 mmol) and dimethyl sulfide (9.23 mL, 124.8 mmol) in acetonitrile (312 mL) cooled to −40° C. was added benzoyl peroxide (15.1 g, 62.3 mmol) and the reaction mixture was warmed to room temperature over 1 h. At this time a TLC (eluted with hexanes:ethyl acetate, 1:1) indicated the reaction was complete. The reaction mixture was then diluted with ethyl acetate and the resulting organic solution was washed three times with a saturated sodium bicarbonate solution then brine. The organic phase was then dried over sodium sulfate and concentrated in vacuo. The 5 residual oil was purified via flash chromatography (eluted with hexanes:ethyl acetate) to provide the title compound (14.4 g, 93%) as a white solid; $^1$H-NMR (CDCl$_3$, 300 MHz) δ8.21–8.19 (2H, m), 7.72–7.70 (2H, m), 7.62–7.26 (11H, m), 6.92 (3H, s), 6.20 (1H, dd, J=8.4 Hz), 5.92 (1H, dd, J=9.0, 3.1 Hz), 5.66 (1H, d, J=6.9 Hz), 5.51 (1H, d, J=3.2 Hz), 4.92 (1H, d, J=8.2 Hz), 4.68–4.59 (2H, m), 4.32–4.26 (2H, m), 4.15 (1H, d, J=8.3 Hz), 3.86 (1H, d, J=6.8 Hz), 2.77 (1H, m), 2.50–1.05 (25H, m), 0.87 (3H, dd, J=7.3 Hz).

(c) Preparation of 2'-O-n-propylcarbonyl-7-O-(dibenzylphosphonooxymethyl)paclitaxel N-Iodosuccinimide (4.9 g, 21.8 mmol) was added in one portion to a solution of 2'-O-n-propylcarbonyl-7-O-methylthiomethylpaclitaxel (10.7 g, 11.0 mmol), dibenzylphosphate (15.3 g, 55.0 mmol) and 5 g of oven dried 3 Angstrom sieves in THF (200 mL) at room temperature and the resulting mixture was stirred for 1 h. At this time a TLC analysis (eluted with hexanes:ethyl acetate, 1:1) indicated the reaction was complete. The reaction mixture was then diluted to twice the initial volume with ethyl acetate and filtered through a bed of celite. The filtrate was then poured into a saturated sodium bicarbonate solution containing 1% sodium thiosulfate by weight. The organic layer was then washed four times with a saturated aqueous sodium bicarbonate solution followed by brine. The aqueous layer was then back extracted with ethyl acetate and the combined organics were dried over sodium sulfate and concentrated in vacuo. The residual oil was purified via flash chromatography (hexanes:ethyl acetate) to provide the title dibenzylphosphate (9.9 g, 76% yield) as a white solid; $^1$H-NMR (CDCl$_3$, 300 MHz) δ8.10–8.08 (2H, m), 7.74–7.71 (2H, m), 7.61–7.25 (21H, m), 6.94 (1H, d, J=9.0 Hz), 6.31 (1H, s), 6.20 (1H, dd, J=8.7 Hz), 5.91 (1H, dd, J=9.0, 3.1 Hz), 5.64 (1H, d, J=6.9 Hz), 5.49 (1H, d, J=3.0 Hz), 5.39 (1H, dd, J=6.6 Hz), 5.05–4.98 (5H, m), 4.86 (1H, d, J=8.4 Hz), 4.26–4.12 (3H, m), 3.84 (1H, d, J=6.8 Hz), 2.82–2.71 (1H, m), 2.52–1.05 (26 H, m, including singlets at 2.43, 2.18, 1.97, 1.69, 1.22, 1.20, 3H each) 0.90–0.85 (3H, dd, J=7.3 Hz).

(d) Preparation of 2'-O-n-propylcarbonyl-7-O-phosphonooxymethylpaclitaxel

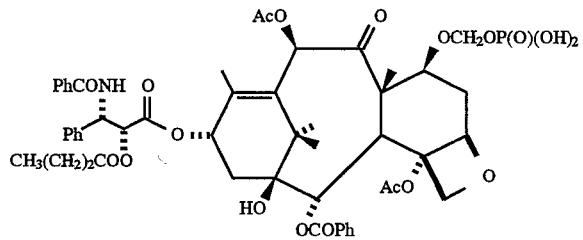

To a nitrogen purged Parr hydrogenation vessel was added 2.5 g of 10% palladium-on-carbon followed by neat ethyl acetate (150 mL) and a solution of 2'-O-n-propylcarbonyl-7-O-(dibenzylphosphonooxymethyl)paclitaxel (4.9 g, 4.14 mmol) in ethyl acetate (40 PAL). The reaction vessel was then fixed to a Parr hydrogenator, placed under vacuum, then pressurized with a hydrogen atmosphere of 50 psi. The heterogenous mixture was then shaken for 5 h after which time a TLC analysis (eluted with hexanes:ethyl acetate) indicated the consumption of starting material. The reaction mixture was then placed under vacuum and subsequently purged with nitrogen. The mixture was then filtered using a sintered glass funnel and the filtrate concentrated in vacuo to provide the title compound (3.7 g, 91% yield) which was pure by $^1$H-NMR analysis.

(e) Preparatin of 2'-O-n-propylcarbonyl-7-O-phosphonooxymethylpaclitaxel triethanolamine salt To a solution of 2'-O-n-propylcarbonyl-7-O-phosphonooxymethylpaclitaxel (1.1 g, 1.09 mmol) in dichloromethane (50 mL) was added a 0.1M solution of triethanolamine (10.9 mL, 1.09 mL) in ethyl acetate and the resulting mixture was stirred for 5 min at room temperature. The reaction mixture was then concentrated in vacuo and the resulting white solid was purified by first dissolving the crude material in a minimum amount of a methylene chloride-ethyl acetate mixture. Hexanes were then added to this solution and the desired amine salt precipitated as a white solid. The mixture was then decanted to provide the amine salt as a white solid which had an observed HPLC purity greater than 95%; $^1$H-NMR (Acetone-d$_6$, D$_2$O, 300 MHz) δ8.09–8.07 (2H, m), 7.86–7.84 (2H), 7.69–7.24 (11H, m), 7.24 (1H, dd, J=7.5 Hz), 6.36 (1H, s), 6.05 (1H, dd, J=8.4 Hz), 5.85 (1H, d, J=6.7 Hz), 5.61 (1H, d, J=7.0 Hz), 5.49 (1H, d, J=6.9 Hz), 5.15–5.13 (1H, m), 4.98 (1H, d, J=8.2 Hz), 4.87 (1H, dd, J=12.1 Hz, 6.4 Hz), 4.12 (bs, 2H), 3.89–3.80 (7H, m), 3.36–3.30 (6H, m), 2.95–2.93 (1H, m), 2.42–1.50 (25H, m, including singlets at 2.42, 2.22, 1.93, 1.66, 3H each), 1.13 (bs, 6H), 0.86–0.81 (2H, dd, J=7.4 Hz).

Example 21.2'-O-Methylcarbonyl-7-O-phosphonooxymethylpaclitaxel (a) Preparation of 2'-O-acetylpaclitaxel

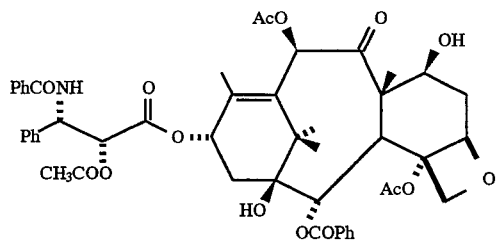

To a solution of paclitaxel (8.0 g, 9.37 mmol) and diisopropylethyl amine (4.89 mL, 28.1 mmol) in dichloromethane (140 mL) cooled to 0° C. was added acetyl chloride (1.0 mL, 14.1 mmol) dropwise over 2 min. The reaction mixture was then warmed to room temperature and stirred for 10h. The reaction mixture was then partitioned between ethyl acetate and a saturated aqueous ammonium chloride solution. The organic phase was then washed with a saturated sodium bicarbonate solution followed by brine, dried over sodium sulfate and concentrated in vacuo. The residual oil was purified using flash chromatography (eluted with hexanes:ethyl acetate) to provide 2'-O-acetylpaclitaxel (7.7 g, 92%) as a white solid; $^1$H-NMR (CDCl$_3$, 300 MHz) δ8.10–8.08 (2H, m), 7.92–7.90 (1H, m), 7.89–7.70 (2H, m), 7.60–7.29 (11H, m), 6.94 (1H, d, J=9.2 Hz), 6.26 (1H, s), 6.23 (1H, dd, J=9.5 Hz), 5.93 (1H, dd, J=9.2, 3.1 Hz), 5.65 (1H, d, J=7.0 Hz), 5.48 (1H, d, J=3.2 Hz), 4.94 (1H, d, J=7.8 Hz), 4.42 (1H, dd, J=10.8 Hz, 6.6 Hz), 4.28 (1H, d, J=8.4 Hz), 4.16 (1H, d, J=8.4 Hz), 3.78 (1H, d, J=6.9 Hz), 2.60–1.02 (25H, m, including singlets at 2.42, 2.19, 2.12, 1.90, 1.65, 1.25, 1.11, 3H each).

(b) Preparation of 2'-O-acetyl-7-O-methylthiomethylpaclitaxel

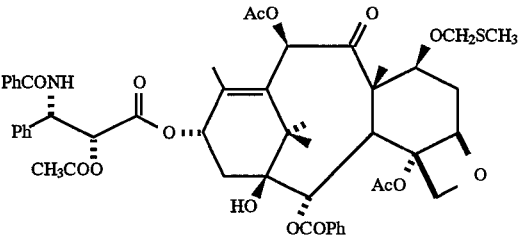

To a solution of 2'-O-acetylpaclitaxel (7.7 g, 8.60 mmol) and dimethyl sulfide (5.1 mL, 68.8 mmol) in acetonitrile (200 mL) cooled to −40° C. was added benzoyl peroxide (8.3 g, 34.4 mmol) and the reaction mixture was warmed to room temperature over 1 h. At this time a TLC (eluted with hexanes:ethyl acetate, 1:1) indicated the reaction was complete. The reaction mixture was then diluted with ethyl acetate and the resulting organic solution was washed three times with a saturated sodium bicarbonate solution then brine. The organic phase was then dried over sodium sulfate and concentrated in vacuo. The residual oil was purified via flash chromatography (hexanes:ethyl acetate) to provide the title methylthiomethylether (7.39 g, 90%) as a white solid; $^1$H-NMR (CDCl$_3$, 300 MHz) δ8.10–8.08 (2H, m), 7.77–7.73 (2H, m), 7.65–7.26 (11H, m), 6.53 (3H, 2), 6.20 (1H, dd, J=8.3 Hz), 5.92 (1H, dd, J=12.2, 3.1 Hz), 5.67 (1H, d, J=7.0 Hz), 5.51 (1H, d, J=3.2 Hz), 4.94 (1H, d, J=8.2 Hz), 4.69–4.60 (3H, m), 4.33–4.28 (2H, m), 4.27 (1H, d, J=8.4 Hz), 3.86 (1H, d, J=6.9 Hz), 2.84–2.74 (1H, m), 2.50–1.1 (28H, m, including singlets at 2.41, 2.15, 2.13, 2.11, 2.06, 1.73, 1.18, 1.15, 3H each).

(c) Preparation of 2'-O-acetyl-7-O-(dibenzylphosphonooxymethyl)paclitaxel

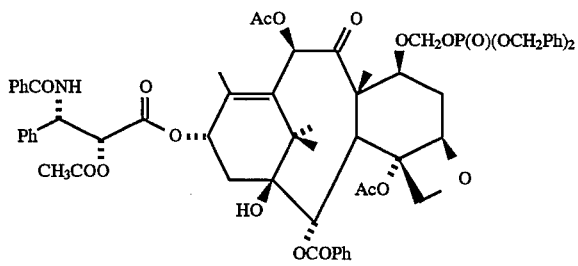

N-Iodosuccinimide (1.75 g, 7.85 mmol) was added in one portion to a solution of 2'-O-acetyl-7-O-methylthiomethylpaclitaxel (5.0 g, 5.23 mmol), dibenzylphosphate (7.3 g, 26.1 mmol) and 5 g of oven dried 3 Angstrom sieves in THF (104 mL) at room temperature and the resulting mixture was stirred for 1.5 h. At this time a TLC analysis (eluted with hexanes:ethyl acetate, 1:1) indicated the reaction was complete. The reaction mixture was then diluted to twice the volume with ethyl acetate and filtered through a bed of celite. The filtrate was then poured into a saturated sodium bicarbonate solution containing 1% sodium thiosulfate by weight. The organic layer was then washed four times with a saturated aqueous sodium bicarbonate solution followed by brine. The aqueous layers were then back extracted with ethyl acetate and the combined organics were dried over sodium sulfate and concentrated in vacuo. The residual oil was purified via flash chromatography (eluted with hexanes:ethyl acetate) to provide the title dibenzylphosphate (4.9 g, 80%) as a white solid.

(b) Preparation of 2'-O-acetyl-7-O-phosphonooxymethylpaclitaxel

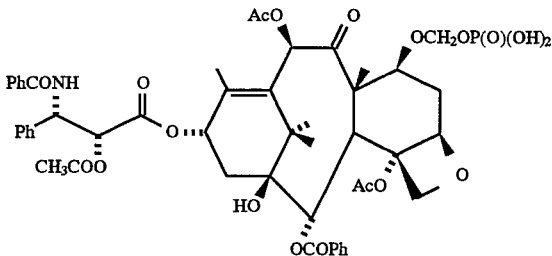

To a nitrogen purged Parr hydrogenation vessel was added 700 mg of 10% palladium-on-carbon followed by neat ethyl acetate (130 mL) and a solution of 2'-O-acetyl-7-O-(dibenzylphosphonooxymethyl)paclitaxel (1.0 g, 0.84 mmol) in ethyl acetate (40 mL). The reaction vessel was then fixed to a Parr hydrogenator, placed under vacuum, then pressurized with a hydrogen atmosphere of 50 psi. The reaction mixture was then shaken for 6 h after which time a TLC analysis (eluted with hexanes:ethyl acetate) indicated the consumption of the starting material. The reaction mixture was then placed under vacuum and subsequently purged with nitrogen. The heterogenous solution was then filtered using a sintered glass funnel and the filtrate concentrated in vacuo to provide a white solid (848 mg) which $^1$H-NMR analysis showed to be a mixture of the desired title compound (50%) and 2'-O-acetylpaclitaxel.

(e) Preparation of 2'-O-acetyl-7-O-phosphonooxymethylpaclitaxel triethanolamine salt To a solution of 2'-O-acetyl-7-O-phosphonooxymethylpaclitaxel (424 mg, 0.42 mmol) and the aforementioned side product 2'-O-acetylpaclitaxel in dichloromethane (15 mL) was added a 0.1M solution of triethanolamine (3.7 mL, 3.8 mmol) in ethyl acetate and the resulting mixture was stirred for 10 min at room temperature. The reaction mixture was then concentrated in vacuo and the resulting white solid was purified by C18 chromatography (water:acetonitrile 2.3:1) to provide the desired amine salt (310 mg, 72%) which had an observed HPLC purity greater than 96%; $^1$H-NMR (Acetone-d$_6$, D$_2$O, 300 MHz) δ8.08–8.05 (2H, m), 7.86–7.83 (2H, m), 7.69–7.24 (11H, m), 7.23 (1H, dd, J=7.4 Hz), 6.35 (1H, s), 6.02 (1H, dd, J=8.3 Hz), 5.79 (1H, d, J=6.9 Hz), 5.59 (1H, d, J=7.1 Hz), 5.45 (1H, d, J=6.9 Hz), 5.12 (1H, dd, J=6.4 Hz), 4.95 (1H, d, J=8.4 Hz), 4.86 (1H, dd, J=11.5, 6.5 Hz), 4.24–4.18 (1H, m), 4.12 (2H, bs), 3.92–3.89 (6H, m), 3.80–3.77 (1H, m), 3.46–3.43 (6H, m), 3.00–2.89 (1H, m), 2.39–1.65 (21H including singlets at 2.39, 2.14, 2.12, 1.92, 1.65, 1.11 3H each) 1.11 (6H, bs).

Example 22

2'-O-methoxycarbonyl-7-O-phosphonooxymethylpaclitaxel (a) Preparation of 2'-O-methoxycarbonylpaclitaxel

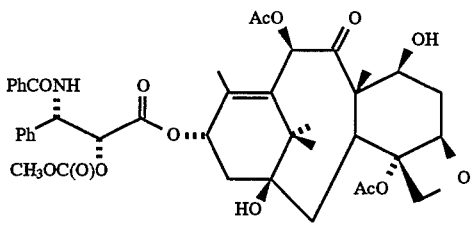

To a solution of paclitaxel (8.0 g, 9.60 mmol) and diisopropylethyl amine (5.0 mL, 28.8 mmol) in dichloromethane (96 mL) cooled to 0° C. was added chloromethyl carbonate (1.11 mL, 14.4 mmol) dropwise over 2 min. The reaction mixture was then warmed to room temperature and stirred for 20 h. The reaction mixture was then partitioned between ethyl acetate and a saturated aqueous ammonium chloride solution. The organic phase was then washed with a saturated sodium bicarbonate solution, followed by brine, dried over sodium sulfate and concentrated in vacuo. The residual oil was purified using flash chromatography (hexanes:ethyl acetate) to provide the title compound (7.8 g, 91.3%) as a white solid; ¹H-NMR (CDCl₃, 300MHz) δ8.12–8.09 (2H, m), 7.72–7.70 (2H, m), 7.62–7.30 (11H, m), 6.96 (1H, d, J=9.3 Hz), 6.29–6.23 (3H, m), 5.95 (1H, dd, J=9.3, 2.5 Hz), 5.66 (1H, d, J=7.1 Hz), 5.38 (1H, d, J=2.6 Hz), 4.94 (1H, d, J=7.8 Hz), 4.41 (1H, dd, J=10.8, 6.6 Hz), 4.28 (1H, d, J=8.4 Hz), 4.17 (1H, d, J=8.4 Hz), 3.79–3.78 (3H, m), 2.60–1.04 (22H, m, including singlets at 2.43, 2.19, 1.90, 1.65, 1.22, 1.10, 3H each).

(b) Preparation of 2'-O-methoxycarbonyl-7-O-methylthiomethylpaclitaxel

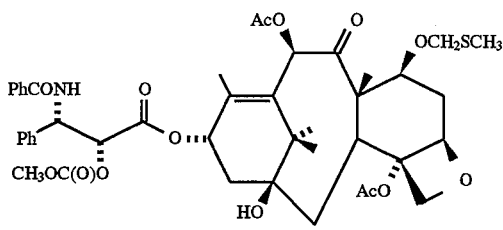

To a solution of 2'-O-methoxycarbonylpaclitaxel (7.4 g, 8.10 mmol) and dimethyl sulfide (4.8 mL, 64.8 mmol) in acetonitrile (162 mL) cooled to −40° C. was added benzoyl peroxide (7.48 g, 32.4 mmol) and the reaction mixture was warmed to room temperature over 1 h. At this time a TLC analysis (eluted with hexanes:ethyl acetate, 1:1) indicated the reaction was complete. The reaction mixture was then diluted with ethyl acetate and the resulting organic solution was washed three times with a saturated sodium bicarbonate solution then brine. The organic phase was then dried over sodium sulfate and concentrated in vacuo. The residual oil was purified via flash chromatography (eluted with hexanes:ethyl acetate) to provide the title compound (7.4 g, 95%) as a white solid; ¹H-NMR (CDCl₃, 300 MHz) δ8.25–8.23 (2H, m), 7.87–7.77 (2H, m), 7.60–7.30 (11H, m), 6.93 (1H, d, J=9.2 Hz), 6.53 (1H, s), 6.25 (1H, dd, J=8.2 Hz), 5.95 (1H, dd, J=11.7, 2.4 Hz), 5.68 (1H, d, J=6.9 Hz), 5.40 (1H, d, J=2.6 Hz), 4.95 (1H, d, J=8.1 Hz), 4.69–4.60 (2H, m), 4.31–4.26 (2H, m), 4.16 (1H, d, J=8.4 Hz), 3.86 (1H, J=6.9 Hz), 3.79 (3H, s), 2.84–2.74 (1H, m), 2.43–1.10 (25H, including singlets at 2.44, 2.15, 2.10, 2.08, 1.73, 1.19, 1.16 3H).

(c) Preparation of 2'-O-methoxycarbonyl-7-O-(dibenzylphosphonooxymethyl)paclitaxel

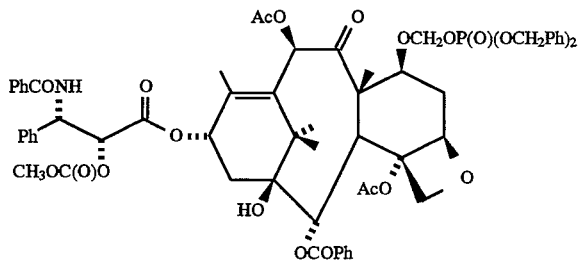

N-Iodosuccinimide (1.74 g, 7.77 mmol) was added in one portion to a solution of 2'-O-methoxycarbonylpaclitaxel (5.04 g, 5.18 mmol), dibenzylphosphate (7.2 g, 25.8 mmol) and 5 g of oven dried 3 Angstrom sieves in THF (100 mL) at room temperature and the resulting mixture was stirred for 1.5 h. At this time a TLC analysis (eluted with hexanes:ethyl acetate, 1:1) indicated the reaction was complete. The reaction mixture was then diluted to twice the volume with ethyl acetate and filtered through a bed of celite. The filtrate was then poured into a saturated sodium bicarbonate solution containing 1% sodium thiosulfate by weight. The organic layer was then washed four times with a saturated aqueous sodium bicarbonate solution followed by brine. The aqueous layer was then back extracted with ethyl acetate and the combined organics were dried over sodium sulfate and concentrated in vacuo. The residual oil was purified via flash chromatography (eluted with hexanes:ethyl acetate) to provide the title compound (5.1 g, 96%) as a white solid; ¹H-NMR (CDCl₃, 300 MHz) δ8.12–8.08 (2H, m), 7.73–7.70 (2H, m), 7.62–7.27 (21H, m), 7.00 (1H, d, J=9.2 Hz), 6.31 (1H, s), 6.24–6.21 (1H, m), 5.96–5.92 (1H, m), 5.66–5.64 (1H, m), 5.40–5.36 (2H, m), 5.05–4.93 (5H, m), 4.87–4.84 (1H, m), 4.29–4.05 (3H, m), 3.85–3.83 (1H, m), 3.77 (3H, s), 2.81–2.71 (1H, m), 2.62–1.05 (22H, m, including singlets at 2.43, 2.19, 2.01, 1.73, 1.22, 1.15, 3H each).

(d) Preparation of 2'-O-methoxycarbonyl-7-O-phosphonooxymethylpaclitaxel

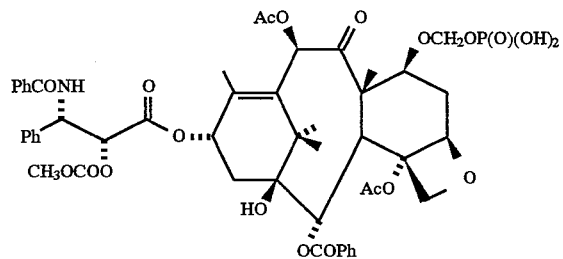

To a nitrogen purged Parr hydrogenation vessel was added 1.3 g of 10% palladium-on-carbon followed by neat ethyl acetate (140 mL) and a solution of 2'-O-methoxycarbonyl-7-O-(dibenzylphosphonooxymethyl)paclitaxel (3.4 g, 3.32 mmol) in ethyl acetate (40 mL). The reaction vessel was then fixed to a Parr hydrogenator, placed under vacuum, then pressurized with a hydrogen atmosphere of 50 psi. The resulting mixture was shaken for 8.5 h after which time a TLC analysis (eluted with hexanes:ethyl acetate) indicated the consumption of starting material. The reaction mixture was then placed under vacuum and subsequently purged with nitrogen. The heterogenous solution was then filtered using a sintered glass funnel and the filtrate concentrated in vacuo to provide a white solid (2.9 g) which ¹H-NMR analysis showed to be a mixture of the desired title product (67%) and 2'-O-methoxycarbonylpaclitaxel (33%).

(e) Preparation of 2'-O-methoxycarbonyl-7-O-phosphonooxymethylpaclitaxel triethanolamine salt To a solution of 2'-O-methoxycarbonyl-7-O-phosphonooxymethylpaclitaxel (1.91 g, 1.87 mmol) and the aforementioned side product 2'-O-methoxycarbonylpaclitaxel in dichloromethane (11 mL) was added a 0.1M solution of triethanolamine (18.9 mL, 1.89 mmol) in ethyl acetate and the resulting mixture was stirred for 5 min at room temperature. The reaction mixture was then concentrated in vacuo and the resulting white solid was purified by C18 chromatography (eluted with water:acetonitrile 2.3:1) to provide after subsequent lyophilization the triethanolamine salt which had an observed HPLC purity greater than 97%; ¹H-NMR (Acetone-d₆, D₂O, 300 MHz) δ8.08–8.06 (2H, m), 7.88–7.55 (2H, m), 7.69–7.24 (11H, m), 7.24 (1H, dd, J=7.3 Hz), 6.36 (1H, m), 6.05 (1H, dd, J=8.8 Hz), 5.82 (1H, d, J=6.8 Hz), 5.60 (1H, d, J=7.1 Hz), 5.46 (1H, d, J=6.9 Hz), 5.13 (1H, dd, J=6.5 Hz), 5.98 (1H, d, J=8.1 Hz), 4.87 (1H, dd, J=11.8 Hz, 6.3 Hz), 4.21 (1H, dd, J=10.3, 6.9 Hz), 4.13 (bs, 6H), 3.92–3.89 (6H, m), 3.81 (1H, d, J=7.02), 3.76 (3H, s), 3.46–3.42 (6H, m), 3.01–2.90 (1H, m), 2.42 (3H, s), 2.20–1.80 (10H, including singlets at 2.20, 1.93), 1.66 (3H, s), 1.12 (6H, bs).

Example 23

Preparation of phosphonooxymethoxymethyl-7-O-phosphonooxymethylpaclitaxel (a) Preparation of 2'-O-methylthiomethoxymethylpaclitaxel

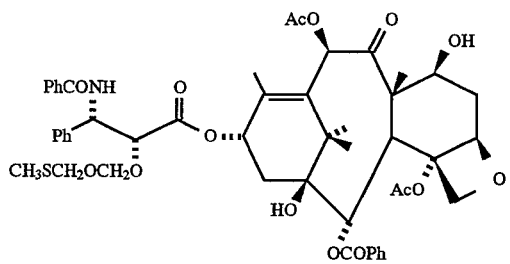

Palladium (10%) on carbon (3 g) was added to a solution of 2'-O-methylthiomethoxymethyl-7-O-benzyloxycarbonylpaclitaxel (1.2 g, 1.11 mmol) in ethyl acetate (100 mL) and ethanol (70 mL) housed in a Parr bottle. The vessel was affixed to a Parr apparatus and the reaction mixture subjected to hydrogen at 50 psi. The reaction mixture was shaken for 20.5 h, then filtered using a sintered glass funnel. The filtrate was concentrated in vacuo and the residual oil purified via flash chromatography (eluted with hexanes:ethyl acetate) to provide the desired (0.98 g, 93%) as a solid. $^1$H-NMR (CDCl$_3$, 300 MHz), δ8.12–8.10 (2H, m), 7.76–7.73 (2H, m),7.61–7.27 (11H, m), 7.03 (1H, d, J=8.9 Hz), 6.40–6.27 (1H, m), 6.25 (1H, s), 5.80 (1H, dd, J=8.9, 2.4 Hz), 5.66 (1H, d, J=7.1 Hz), 4.98–4.94 (1H, m), 4.86–4.79 (2H, m), 4.75–4.68 (1H, Ira), 4.43–4.39 (1H, m), 4.31–4.26 (2H, m), 4.05 (1H, d, J=11.7 Hz), 3.78 (1H, d, J=7.1 Hz), 2.60–1.06 (25H, m, including singlets at 2.45, 2.21, 2.02, 1.85, 1.66, 1.22, 1.11, 3H each).

(b) Preparation of 2'-O-methylthiomethoxymethyl-7-O-methylthiomethylpaclitaxel

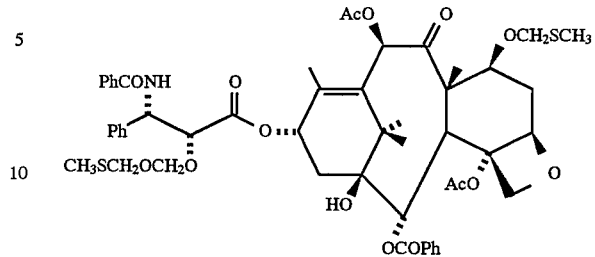

To a solution of 2'-O-methylthiomethoxymethylpaclitaxel. (0.98 g, 1.03 mmol) and dimethyl sulfide (0.6 mL, 8.11 mmol) in acetonitrile (20 mL) cooled to –40° C. was added benzoyl peroxide (1.0 g, 4.13 mmol) and the reaction mixture was warmed to room temperature over 30 min. At this time a TLC analysis (eluted with hexanes:ethyl acetate, 1:1) indicated the reaction was complete. The reaction mixture was then diluted with ethyl acetate and the resulting organic solution was washed three times with a saturated sodium bicarbonate solution then brine. The organic phase was then dried over sodium sulfate and concentrated in vacuo. The residual oil was purified via flash chromatography (eluted with hexanes:ethyl acetate) to provide the title product (0.945 g, 91%) as a white solid; $^1$H-NMR (CDCl$_3$, 300 MHz) δ8.13–8.11 (2H, m), 7.79–7.77 (2H, m), 7.61–7.29 (11H, m), 6.54 (1H, s), 6.30–6.26 (1H, m), 5.83–5.80 (1H, m), 5.71–5.69 (1H, m), 5.01–4.66 (6H, m), 4.34–4.04 (5H, m), 3.88 (1H, d, J=6.6 Hz), 2.90–2.80 (1H, m), 2.55–1.05 (27H, m, including singlets at 2.51, 2.18, 2.11, 1.80, 1.21, 1.20, 3H each).

(c) Preparation of 2'-O-dibenzylphosphonooxymethoxymethyl-7-O-(dibenzylphosphonooxymethyl)paclitaxel

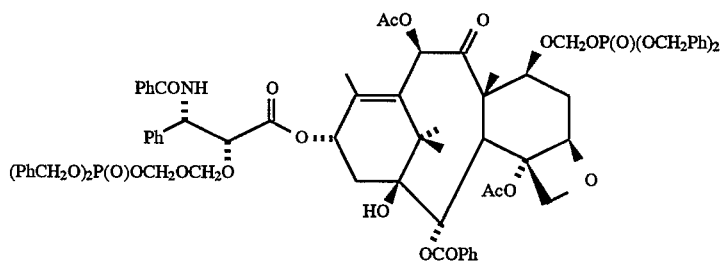

N-Iodosuccinimide (0.615 g, 2.74 mmol) was added in one portion to a solution 2'-O-methylthiomethoxymethyl-7-O-methylthiomethylpaclitaxel (0.92 g, 0.916 mmol), dibenzylphosphate (2.03 g, 7.30 mmol) and 1 g of oven dried 3 Angstrom sieves in THF (18 mL) at room temperature and the resulting mixture was stirred for 30 min. At this time a TLC analysis (eluted with hexanes:ethyl acetate, 1:2) indicated the reaction was complete. The reaction mixture was then diluted to twice the volume with ethyl acetate and filtered through a bed of celite. The filtrate was then poured into a saturated sodium bicarbonate solution containing 1% sodium thiosulfate by weight. The organic layer was then washed four times with a saturated aqueous sodium bicarbonate solution followed by brine. The aqueous layer was then back extracted with ethyl acetate and the combined organics were dried over sodium sulfate and concentrated in vacuo. The residual oil was purified via flash chromatography (eluted with hexanes:ethyl acetate) to provide the title product (0.768 g, 58%) as a white solid; $^1$H-NMR (CDCl$_3$, 300 MHz) δ8.10–8.05 (2H, m), 7.80–7.74 (2H, m), 7.65–7.27 (11H, m), 6.30 (1H, s), 6.25–6.18 (1H, m), 5.82 (1H, dd, J=9.1, 3.4 Hz), 5.63 (1H, dd, J=6.9 Hz), 5.38 (1H, dd, J=6.6 Hz), 5.10–4.60 (15H, m), 4.30–4.10 (3H, m), 3.80 (1H, d, J=6.8 Hz), 2.85–2.65 (1H, m), 2.50–1.60 (22H, m, including singlets at 2.47, 2.16, 1.91, 1.72, 1.88, 1.15, 3H each).

(d) Preparation of 2'-O-phosphonooxymethoxymethyl-7-O-phosphonooxymethylpaclitaxel

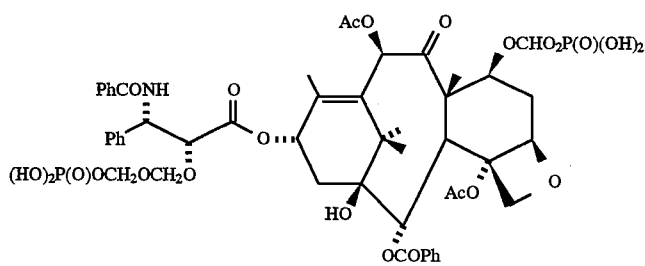

To a nitrogen purged Parr hydrogenation vessel was added 1.3 g of 10% palladium-on-carbon followed by neat ethyl acetate (110 mL) and a solution of 2'-O-dibenzylphosphonooxymethoxymethyl-7-O-(dibenzylphosphonooxymethyl)paclitaxel (0.721 g, 0.498 mmol) in ethyl acetate (40 mL). The reaction vessel was then fixed to a Parr hydrogenator, placed under vacuum then pressurized with a hydrogen atmosphere of 50 psi. The heterogenous mixture was then shaken for 16 h after which time a TLC analysis (eluted with hexanes:ethyl acetate) indicated the consumption of starting material. The reaction mixture was then placed under vacuum and subsequently purged with nitrogen. The mixture was then filtered using a sintered glass funnel and the filtrate concentrated in vacuo to provide the title product (0.413 g) which was at 60% purity by HPLC analysis.

(e) Preparation of 2'-O-phosphonooxymethoxymethyl-7-O-phosphonooxymethylpaclitaxel bis-triethanolamine salt To a solution of crude of 2'-O-phosphonooxymethoxymethyl-7-O-phosphonooxymethylpaclitaxel (413 mg) in dichloromethane (10 mL) was added a 0.1M solution of triethanolamine (7.6 mL, 0.076 mmol) in ethyl acetate and the resulting mixture was stirred for 5 min at 5 room temperature. The reaction mixture was then concentrated in vacuo and the resulting white solid was purified by C18 chromatography (eluted with water:acetonitrile, 9:1 to 5.6:1). Fractions of eluent containing the desired salt in greater than 96% purity by HPLC were combined and the acetonitrile was removed via rotary evaporation. The resulting aqueous solution of the amine salt was lyophilized to provide the desired salt (0.210 g, 30% over 2 steps) as a white solid. $^1$H- NMR (Acetone-d$_6$, D$_2$O, 300 MHz) δ7.97–7.94 (2H, m), 7.79–7.76 (2H, m), 7.67–7.33 (11H, m), 7.12–7.07 (1H, m), 6.26 (1H, s), 5.89 (1H, dd, J=8.6 Hz), 5.48 (1H, d, J=7.9 Hz), 5.00–4.79 (8H, m), 4.70 (1H, d, J=8.1 Hz), 4.15–4.03 (3H, m), 3.74–3.66 (7H, m), 3.14–2.86 (8H, m), 2.33–1.00 (20H, m, including singlets at 2.33, 2.10, 1.88, 1.56, 1.02, 1.00, 3H each).

ADDITIONAL EXAMPLES

The general procedures provided in the foregoing examples and descriptions are followed in the preparation of the following compounds within the scope of formula (A).

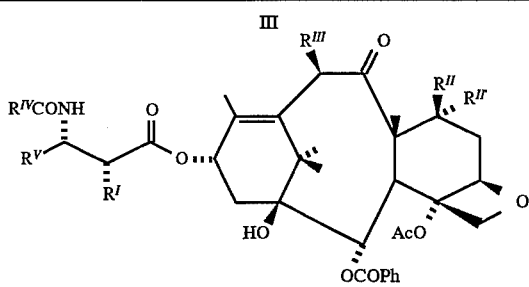

| $R^I$ | $R^{II'}$ | $R^{II}$ | $R^{III}$ | $R^{IV}$ | $R^V$ |
|---|---|---|---|---|---|
| OH | H | —OCH$_2$OP(O)(OH)$_2$ | AcO | Ph | 4-F—Ph— |
|  |  |  |  |  | 4-CH$_3$—Ph |
|  |  |  |  |  | 2-furanyl |
|  |  |  |  |  | 2-thienyl |
|  |  |  |  |  | (CH$_3$)$_2$CH— |
|  |  |  |  |  | isobutenyl |
|  |  |  |  |  | (2-methyl-1-propenyl) |
|  |  |  |  |  | *c-C$_3$H$_6$— |
|  |  |  |  |  | 3-furanyl |
|  |  |  |  |  | 3-thienyl |
|  |  |  |  |  | 2-propenyl |
| —OCH$_2$OP(O)(OH)$_2$ | H | OH | AcO | Ph | 4-CF$_3$—Ph— |
|  |  |  |  |  | 2-furanyl |
|  |  |  |  |  | (CH$_3$)$_2$CH— |
|  |  |  |  |  | 2-thienyl |
|  |  |  |  |  | isobutenyl |
|  |  |  |  |  | cyclopropyl |
|  |  |  |  |  | 3-thienyl |
|  |  |  |  |  | 3-furanyl |
|  |  |  |  |  | 2-propenyl |
|  |  |  |  |  | isopropyl |
| CH$_3$CH$_2$OC(O)O— | H | —OCH$_2$OP(O)(OH)$_2$ | AcO | Ph | 4-F—Ph— |
|  |  |  |  |  | 2-thienyl |
|  |  |  |  |  | isopropyl |
|  |  |  |  |  | 2-propenyl |
|  |  |  |  |  | isobutenyl |
|  |  |  |  |  | cyclopropyl |
|  |  |  |  |  | 2-furanyl |
|  |  |  |  |  | 3-furanyl |
|  |  |  |  |  | 3-thienyl |
| —OCH$_2$OP(O)(OH)$_2$ | H | OH | OH | (CH$_3$)$_3$CO— | Ph |
|  |  | H |  |  |  |
|  |  | CH$_3$CH$_2$OC(O)O— |  |  |  |
| OH | H | —OCH$_2$OP(O)(OH)$_2$ | OH | (CH$_3$)$_3$CO— | Ph |
| CH$_3$CH$_2$OC(O)O$_2$ |  |  |  |  |  |
| —OCH$_2$OP(O)(OH)$_2$ | H | H | AcO | Ph | Ph |
|  |  | CH$_3$CH$_2$OC(O)O— |  |  |  |
| OH | H | —OCH$_2$OP(O)(OH)$_2$ | AcO | Ph | Ph |
| CH$_3$OC(O)O— |  |  |  |  |  |
| CH$_3$CH$_2$OC(O)O— |  |  |  |  |  |
| CH$_3$(CH$_2$)$_2$OC(O)O— |  |  |  |  |  |
| CH$_3$(CH$_2$)$_3$OC(O)O— |  |  |  |  |  |
| CCl$_3$CH$_2$OC(O)O— |  |  |  |  |  |
| CH$_3$C(O)O— |  |  |  |  |  |
| CH$_3$CH$_2$(O)O— |  |  |  |  |  |
| CH$_3$(CH$_2$)$_2$C(O)O— |  |  |  |  |  |
| CH$_3$(CH$_2$)$_3$C(O)O— |  |  |  |  |  |
| PhC(O)O— |  |  |  |  |  |
| PhOC(O)O— |  |  |  |  |  |
| CH$_2$=CHCH$_2$OC(O)O— |  |  |  |  |  |
| PhCH$_2$OC(O)O— |  |  |  |  |  |
| OH | H | OH | —OCH$_2$OP(O)(OH)$_2$ | Ph | Ph |
| OH | H | H | —OCH$_2$OP(O)(OH)$_2$ | Ph | Ph |
| —OCH$_2$OP(O)(OH)$_2$ | H | H | H | (CH$_3$)$_3$CO— | 4-CH$_3$O—Ph |
| OH | H | —OCH$_2$OP(O)(OH)$_2$ | AcO | (CH$_3$)$_3$CO— | isobutenyl |
|  |  |  |  |  | 2-propenyl |
|  |  |  |  |  | cyclopropyl |
|  |  |  |  |  | 3-furanyl |
|  |  |  |  |  | 3-thienyl |
|  |  |  |  |  | isopropyl |
|  |  |  |  |  | cyclobutyl |
|  |  |  |  |  | isopropyl |
| CH$_3$OC(O)O— | H | —OCH$_2$OP(O)(OH)$_2$ | AcO | (CH$_3$)$_3$CO— | isobutenyl |

-continued

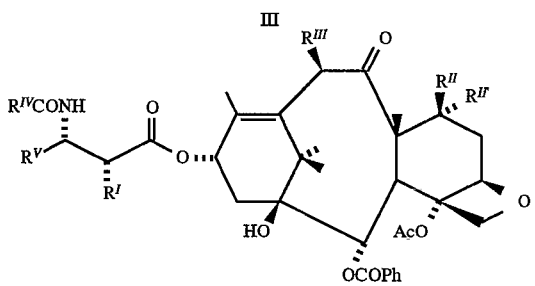

| R^I | R^II, R^II' | R^III | R^IV | R^V |
|---|---|---|---|---|
| CH₃CH₂OC(O)O— | H  —OCH₂OP(O)(OH)₂ | AcO | (CH₃)₃CO— | 2-propenyl<br>cyclopropyl<br>3-furanyl<br>3-thienyl<br>isopropyl<br>cyclobutyl<br>isopropyl<br>isobutenyl |
| CH₃(CH₂)₂OC(O)O— | H  —OCH₂OP(O)(OH)₂ | AcO | (CH₃)₃CO— | 2-propenyl<br>cyclopropyl<br>3-furanyl<br>3-thienyl<br>isopropyl<br>cyclobutyl<br>isopropyl<br>isobutenyl |
| CH₃(CH₂)₃OC(O)O— | H  —OCH₂OP(O)(OH)₂ | AcO | (CH₃)₃CO— | 2-propenyl<br>cyclopropyl<br>3-furanyl<br>3-thienyl<br>isopropyl<br>cyclobutyl<br>isopropyl<br>isobutenyl |
| CCl₃CH₂OC(O)O— | H  —OCH₂OP(O)(OH)₂ | AcO | (CH₃)₃CO— | 2-propenyl<br>cyclopropyl<br>3-furanyl<br>3-thienyl<br>isopropyl<br>cyclobutyl<br>isopropyl<br>isobutenyl |
| CH₃C(O)O— | H  —OCH₂OP(O)(OH)₂ | AcO | (CH₃)₃CO— | 2-propenyl<br>cyclopropyl<br>3-furanyl<br>3-thienyl<br>isopropyl<br>cyclobutyl<br>isopropyl<br>isobutenyl |
| CH₃CH₂(O)O— | H  —OCH₂OP(O)(OH)₂ | AcO | (CH₃)₃CO— | 2-propenyl<br>cyclopropyl<br>3-furanyl<br>3-thienyl<br>isopropyl<br>cyclobutyl<br>isopropyl<br>isobutenyl |
| CH₃(CH₂)₂C(O)O— | H  —OCH₂OP(O)(OH)₂ | AcO | (CH₃)₃CO— | 2-propenyl<br>cyclopropyl<br>3-furanyl<br>3-thienyl<br>isopropyl<br>cyclobutyl<br>isopropyl<br>isobutenyl |
| CH₃(CH₂)₃C(O)O— | H  —OCH₂OP(O)(OH)₂ | AcO | (CH₃)₃CO— | isopropyl<br>isobutenyl |

-continued

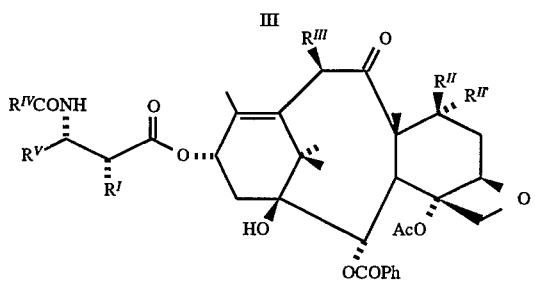

| $R^I$ | $R^{II'}$ | $R^{II}$ | $R^{III}$ | $R^{IV}$ | $R^V$ |
|---|---|---|---|---|---|
| PhC(O)O— | H | —OCH$_2$OP(O)(OH)$_2$ | AcO | (CH$_3$)$_3$CO— | 2-propenyl<br>cyclopropyl<br>3-furanyl<br>3-thienyl<br>isopropyl<br>cyclobutyl<br>isopropyl<br>isobutenyl |
| PhOC(O)O— | H | —OCH$_2$OP(O)(OH)$_2$ | AcO | (CH$_3$)$_3$CO— | 2-propenyl<br>cyclopropyl<br>3-furanyl<br>3-thienyl<br>isopropyl<br>cyclobutyl<br>isopropyl<br>isobutenyl |
| CH$_2$=CHCH$_2$OC(O)O— | H | —OCH$_2$OP(O)(OH)$_2$ | AcO | (CH$_3$)$_3$CO— | 2-propenyl<br>cyclopropyl<br>3-furanyl<br>3-thienyl<br>isopropyl<br>cyclobutyl<br>isopropyl<br>isobutenyl |
| PhCH$_2$OC(O)O— | H | —OCH$_2$OP(O)(OH)$_2$ | AcO | (CH$_3$)$_3$CO— | 2-propenyl<br>cyclopropyl<br>3-furanyl<br>3-thienyl<br>isopropyl<br>cyclobutyl<br>isopropyl<br>isobutenyl |
| —OCO$_2$CH$_2$CH$_3$ | H | —OCH$_2$OP(O)(OH)$_2$ | AcO | CH$_3$CH$_2$CH$_2$CH$_2$O— | 2-propenyl<br>cyclopropyl<br>3-furanyl<br>isobutenyl<br>2-propenyl<br>cyclopropyl<br>cyclobutyl<br>3-thienyl<br>2-thienyl<br>isopropyl |
| OH | H | —OCH$_2$OP(O)(OH)$_2$ | AcO | CH$_3$CH$_2$CH$_2$CH$_2$O— | 2-furanyl<br>3-furanyl<br>isobutenyl<br>2-propenyl<br>cyclopropyl<br>cyclobutyl<br>3-thienyl<br>2-thienyl<br>isopropyl |
| —OCO$_2$CH$_2$CH$_3$ | H | —OCH$_2$OP(O)(OH)$_2$ | AcO | isopropyloxy | 2-furanyl<br>3-furanyl<br>2-thienyl<br>isobutenyl<br>2-propenyl<br>cyclopropyl<br>cyclobutyl |

-continued

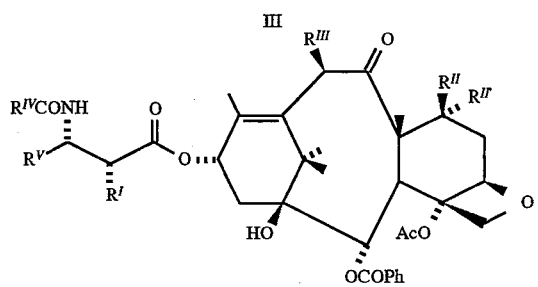

| $R^I$ | $R^{II'}$ | $R^{II}$ | $R^{III}$ | $R^{IV}$ | $R^V$ |
|---|---|---|---|---|---|
| OH | H | —OCH$_2$OP(O)(OH)$_2$ | OMe | (CH$_3$)$_3$CO— | 2-thienyl<br>2-propenyl<br>2-furanyl<br>3-furanyl<br>3-thienyl<br>isopropyl<br>cyclopropyl<br>isobutenyl |
| —OCO$_2$CH$_2$CH$_3$ | H | —OCH$_2$OP(O)(OH)$_2$ | —OC(O)Ph | (CH$_3$)$_3$CO— | 2-thienyl<br>2-propenyl<br>2-furanyl<br>3-furanyl<br>3-thienyl<br>isopropyl<br>cyclopropyl<br>isobutenyl |
| OH | H | —OCH$_2$OP(O)(OH)$_2$ | —OC(O)Ph | (CH$_3$)$_3$CO— | 2-thienyl<br>2-propenyl<br>2-furanyl<br>3-furanyl<br>3-thienyl<br>isopropyl<br>cyclopropyl<br>isobutenyl |
| —OCO$_2$CH$_2$CH$_3$ | H | —OCH$_2$OP(O)(OH)$_2$ | —OCO$_2$CH$_3$ | Ph<br>CH$_3$CH$_2$CH$_2$CH$_2$O—<br>isopropyloxy | 2-thienyl<br>2-propenyl<br>2-furanyl |
| OH | H | —OCH$_2$OP(O)(OH)$_2$ | —OCO$_2$CH$_3$ | Ph<br>CH$_3$CH$_2$CH$_2$CH$_2$O—<br>isopropyloxy | 2-furanyl |
| —OCO$_2$CH$_2$CH$_3$ | H | —OCH$_2$OP(O)(OH)$_2$ | OMe | Ph<br>CH$_3$CH$_2$CH$_2$CH$_2$O—<br>isopropyloxy | 2-furanyl |
| OH | H | —OCH$_2$OP(O)(OH)$_2$ | OMe | Ph<br>CH$_3$CH$_2$CH$_2$CH$_2$O—<br>isopropyloxy | 2-furanyl |
| —OCO$_2$CH$_2$CH$_3$ | H | —OCH$_2$OP(O)(OH)$_2$ | —OC(O)Ph | Ph<br>CH$_3$CH$_2$CH$_2$CH$_2$O—<br>isopropyloxy | 2-furanyl |
| OH | H | —OCH$_2$OP(O)(OH)$_2$ | —OC(O)Ph | Ph<br>CH$_3$CH$_2$CH$_2$CH$_2$O—<br>isopropyloxy | 2-furanyl |
| —OCO$_2$CH$_2$CH$_3$ | H | —OCH$_2$OCH$_2$OP(O)(OH)$_2$ | —OCO$_2$CH$_3$ | (CH$_3$)$_3$CO—<br>isopropyloxy<br>CH$_3$CH$_2$CH$_2$CH$_2$O— | 2-furanyl |
| OH | H | —OCH$_2$OCH$_2$OP(O)(OH)$_2$ | —OCO$_2$CH$_3$ | (CH$_3$)$_3$CO—<br>isopropyloxy<br>CH$_3$CH$_2$CH$_2$CH$_2$O— | 2-furanyl |
| —OCO$_2$CH$_2$CH$_3$ | H | —OCH$_2$OCH$_2$OP(O)(OH)$_2$ | OMe | (CH$_3$)$_3$CO—<br>isopropyloxy<br>CH$_3$CH$_2$CH$_2$CH$_2$O— | 2-furanyl |
| OH | H | —OCH$_2$OCH$_2$OP(O)(OH)$_2$ | OMe | (CH$_3$)$_3$CO—<br>isopropyloxy<br>CH$_3$CH$_2$CH$_2$CH$_2$O— | 2-furanyl |
| —OCO$_2$CH$_2$CH$_3$ | H | —OCH$_2$OCH$_2$OP(O)(OH)$_2$ | —OC(O)Ph | (CH$_3$)$_3$CO—<br>isopropyloxy<br>CH$_3$CH$_2$CH$_2$CH$_2$O— | 2-furanyl |
| OH | H | —OCH$_2$OCH$_2$OP(O)(OH)$_2$ | —OC(O)Ph | (CH$_3$)$_3$CO—<br>isopropyloxy<br>CH$_3$CH$_2$CH$_2$CH$_2$O— | 2-furanyl |
| —OCO$_2$CH$_2$CH$_3$ | H | —OCH$_2$OCH$_2$OP(O)(OH)$_2$ | —OCO$_2$CH$_3$ | (CH$_3$)$_3$CO— | isobutenyl |
| —OCO$_2$CH$_2$CH$_3$ | H | —OCH$_2$OCH$_2$OP(O)(OH)$_2$ | OMe | (CH$_3$)$_3$CO— | isobutenyl |

-continued

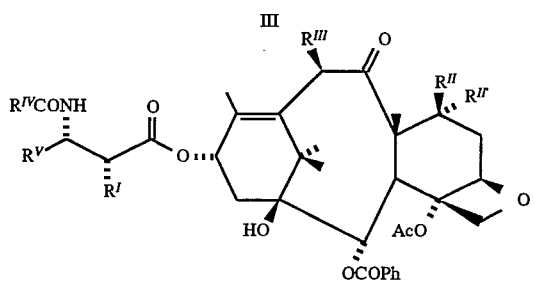

| $R^I$ | $R^{II'}$ | $R^{II}$ | $R^{III}$ | $R^{IV}$ | $R^V$ |
|---|---|---|---|---|---|
| —OCO$_2$CH$_2$CH$_3$ | H | —OCH$_2$OCH$_2$OP(O)(OH)$_2$ | —OC(O)Ph | (CH$_3$)$_3$CO— | isobutenyl |
| OH | H | —OCH$_2$OCH$_2$OP(O)(OH)$_2$ | —OCO$_2$CH$_3$ | Ph | 2-furanyl |
| OH | H | —OCH$_2$OCH$_2$OP(O)(OH)$_2$ | OMe | Ph | 2-furanyl |
| OH | H | —OCH$_2$OCH$_2$OP(O)(OH)$_2$ | —OC(O)Ph | Ph | 2-furanyl |
| —OCO$_2$CH$_2$CH$_3$ | H | —OCH$_2$OCH$_2$OP(O)(OH)$_2$ | —OCO$_2$CH$_3$ | (CH$_3$)$_3$CO— | 2-propenyl |
| —OCO$_2$CH$_2$CH$_3$ | H | —OCH$_2$OCH$_2$OP(O)(OH)$_2$ | OMe | (CH$_3$)$_3$CO— | 2-propenyl |
| —OCO$_2$CH$_2$CH$_3$ | H | —OCH$_2$OCH$_2$OP(O)(OH)$_2$ | —OC(O)Ph | (CH$_3$)$_3$CO— | 2-propenyl |
| —OCH$_2$OCH$_2$OP(O)(OH)$_2$ | H | OH | AcO | (CH$_3$)$_3$CO— | 2-furanyl<br>2-thienyl<br>3-furanyl<br>3-thienyl<br>isobutenyl<br>2-propenyl<br>cyclopropyl |
| —OCH$_2$OCH$_2$OP(O)(OH)$_2$ | H | OH | AcO | CH$_3$CH$_2$CH$_2$CH$_2$O—<br>isopropyloxy<br>(CH$_3$)$_3$CO— | 2-furanyl |
| —OCH$_2$OCH$_2$OP(O)(OH)$_2$ | H | OH | —OCO$_2$CH$_3$ | (CH$_3$)$_3$CO—<br>Ph<br>isopropyloxy | 2-furanyl |
| —OCH$_2$OCH$_2$OP(O)(OH)$_2$ | H | OH | OMe | (CH$_3$)$_3$CO—<br>Ph<br>isopropyloxy | 2-furanyl |
| —OCH$_2$OCH$_2$OP(O)(OH)$_2$ | H | OH | —OC(O)Ph | (CH$_3$)$_3$CO—<br>Ph<br>isopropyloxy | 2-furanyl |
| —OCO$_2$CH$_2$CH$_3$ | H | —OCH$_2$OCH$_2$OP(O)(OH)$_2$ | AcO | Ph | Ph |
| OH | F | H | —OCH$_2$OP(O)(OH)$_2$ | (CH$_3$)$_3$CO—<br>Ph | Ph |
| —OCO$_2$CH$_2$CH$_3$ | F | H | —OCH$_2$OP(O)(OH)$_2$ | (CH$_3$)$_3$CO—<br>Ph | Ph |
| —OCH$_2$OP(O)(OH)$_2$ | F | H | AcO | Ph | 2-furanyl<br>isobutenyl<br>3-furanyl<br>2-thienyl<br>2-propenyl<br>cyclopropyl<br>3-thienyl<br>isopropyl |
| —OCH$_2$OCH$_2$OP(O)(OH)$_2$ | F | H | AcO | Ph | 2-furanyl<br>isobutenyl<br>3-furanyl<br>2-thienyl<br>2-propenyl<br>cyclopropyl<br>3-thienyl<br>isopropyl |
| —OCH$_2$OP(O)(OH)$_2$ | F | H | AcO | (CH$_3$)$_3$CO— | 2-furanyl<br>3-thienyl<br>isobutenyl<br>3-furanyl<br>cyclopropyl<br>2-thienyl<br>Ph<br>2-propenyl |
| —OCH$_2$OCH$_2$OP(O)(OH)$_2$ | F | H | AcO | (CH$_3$)$_3$CO— | 2-furanyl<br>3-thienyl<br>isobutenyl<br>3-furanyl<br>cyclopropyl<br>2-thienyl<br>Ph<br>2-propenyl |
| —OCH$_2$OP(O)(OH)$_2$ | F | H | —OCO$_2$CH$_3$ | (CH$_3$)$_3$CO— | 2-furanyl |

-continued

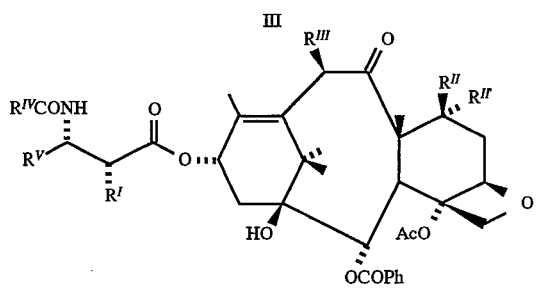

| $R^I$ | $R^{II'}$ | $R^{II}$ | $R^{III}$ | $R^{IV}$ | $R^V$ |
|---|---|---|---|---|---|
| —OCH₂OP(O)(OH)₂ | F | H | OMe | (CH₃)₃CO— | 2-furanyl |
| —OCH₂OP(O)(OH)₂ | F | H | —OC(O)Ph | (CH₃)₃CO— | 2-furanyl |
| —OCH₂OCH₂OP(O)(OH)₂ | F | H | —OCO₂CH₃ | (CH₃)₃CO— | 2-furanyl |
| —OCH₂OCH₂OP(O)(OH)₂ | F | H | OMe | (CH₃)₃CO— | 2-furanyl |
| —OCH₂OCH₂OP(O)(OH)₂ | F | H | —OC(O)Ph | (CH₃)₃CO— | 2-furanyl |
| —OCH₂OCH₂OP(O)(OH)₂ | H | OH | OH | (CH₃)₃CO— | Ph |
| OH | H | —OCH₂OCH₂OP(O)(OH)₂ | OH | (CH₃)₃CO— | Ph |
| —OCO₂CH₂CH₃ | H | —OCH₂OCH₂OP(O)(OH)₂ | OH | (CH₃)₃CO— | Ph |
| OH | H | OH | —OCH₂OCH₂OP(O)(OH)₂ | (CH₃)₃CO— | Ph |
| —OCO₂CH₂CH₃ | H | OH | —OCH₂OCH₂OP(O)(OH)₂ | (CH₃)₃CO— | Ph |
| OH | F | H | —OCH₂OCH₂OP(O)(OH)₂ | (CH₃)₃CO— | Ph |
| | | | | | 2-furanyl |
| | | | | | 3-furanyl |
| | | | | | 2-thienyl |
| | | | | | 3-thienyl |
| | | | | | isobutenyl |
| | | | | | cyclopropyl |
| | | | | | 2-propenyl |
| —OCO₂CH₂CH₃ | F | H | —OCH₂OCH₂OP(O)(OH)₂ | (CH₃)₃CO— | Ph |
| | | | | | 2-furanyl |
| | | | | | 3-furanyl |
| | | | | | 2-thienyl |
| | | | | | 3-thienyl |
| | | | | | isobutenyl |
| | | | | | cyclopropyl |
| | | | | | 2-propenyl |
| —OCH₂OCH₂OP(O)(OH)₂ | H | —OCH₂OCH₂OP(O)(OH)₂ | OAc | Ph | Ph |
| | | | | | 2-furanyl |
| —OCH₂OCH₂OP(O)(OH)₂ | H | —OCH₂OCH₂OP(O)(OH)₂ | OAc | tBuO | Ph |
| | | | | | 2-furanyl |
| —OCH₂(OCH₂)₂OP(O)(OH)₂ | H | OH —OCH₂OCH₂OP(O)(OH)₂ —OCH₂OP(O)(OH)₂ —OCH₂(OCH₂)₂OP(O)(OH)₂ | OAc | Ph | Ph |
| —OCH₂(OCH₂)₂OP(O)(OH)₂ | H | OH | OAc | tBuO | Ph |
| | | | | | 2-furanyl |
| —OCH₂(OCH₂)₂OP(O)(OH)₂ | H | —OCH₂OP(O)(OH)₂ | OAc | tBuO | Ph |
| | | | | | 2-furanyl |
| —OCH₂(OCH₂)₂OP(O)(OH)₂ | H | —OCH₂OCH₂OP(O)(OH)₂ | OAc | tBuO | Ph |
| | | | | | 2-furanyl |
| —OCH₂(OCH₂)₂OP(O)(OH)₂ | H | —OCH₂(OCH₂)₂OP(O)(OH)₂ | OAc | tBuO | Ph |
| | | | | | 2-furanyl |
| —OCH₂(OCH₂)₃OP(O)(OH)₂ | H | —OH | OAc | Ph | Ph |
| —OCH₂(OCH₂)₃OP(O)(OH)₂ | H | —OH | OAc | tBuO | Ph |
| | | | | | 2-furanyl |
| —OCH₂(OCH₂)₃OP(O)(OH)₂ | H | —OCH₂OP(O)(OH)₂ | OAc | Ph tBuO | Ph |
| —OCH₂(OCH₂)₃OP(O)(OH)₂ | H | —OCH₂OP(O)(OH)₂ | OAc | tBuO | 2-furanyl |
| —OCH₂(OCH₂)₃OP(O)(OH)₂ | H | —OCH₂OCH₂OP(O)(OH)₂ | OAc | Ph tBuO | Ph |
| —OCH₂(OCH₂)₃OP(O)(OH)₂ | H | —OCH₂OCH₂OP(O)(OH)₂ | OAc | tBuO | 2-furanyl |
| —OCH₂(OCH₂)₃OP(O)(OH)₂ | H | —OCH₂(OCH₂)₂OP(O)(OH)₂ | OAc | Ph tBuO | Ph |
| —OCH₂(OCH₂)₃OP(O)(OH)₂ | H | —OCH₂(OCH₂)₂OP(O)(OH)₂ | OAc | tBuO | 2-furanyl |
| —OCH₂(OCH₂)₃OP(O)(OH)₂ | H | —OCH₂(OCH₂)₃OP(O)(OH)₂ | OAc | Ph | Ph |
| | | | | | 2-furanyl |
| —OCH₂(OCH₂)₃OP(O)(OH)₂ | H | —OCH₂(OCH₂)₃OP(O)(OH)₂ | OAc | tBuO | Ph |
| | | | | | 2-furanyl |

*"c" indicates cyclo

We claim:
1. A compound having the formula

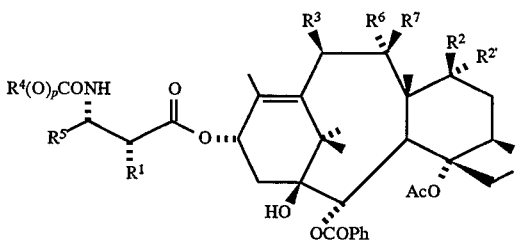

wherein $R^1$ is hydroxy, —$OCH_2(OCH_2)_mOP(O)(OH)_2$, —$OC(O)R^x$ or —$OC(O)OR^x$;

$R^{2'}$ is hydrogen, and $R^2$ is hydrogen, hydroxy, —$OCH_2(OCH_2)_mOP(O)(OH)_2$, —$OC(O)R^x$ or —$OC(O)OR^x$;

$R^3$ is hydrogen, hydroxy, $C_{1-6}$alkyloxy, —$OC(O)R^x$, —$OCH_2(OCH_2)_mOP(O)(OH)_2$ or —$OC(O)OR^x$;

one of $R^6$ or $R^7$ is hydrogen and the other is hydroxy, $C_{1-6}$ alkanoyloxy, or —$OCH_2(OCH_2)_mOP(O)(OH_2)$; or $R^6$ and $R^7$ together form an oxo group; with the proviso that at least one of $R^1$, $R^2$, $R^3$, $R^6$ or $R^7$ is —$OCH_2(OCH_2)_mOP(O)(OH)_2$;

m is zero or an integer one to six inclusive;

$R^4$ and $R^5$ are independently $C_{1-6}$ alkyl, $C_{2-6}$ alkenyl, $C_{2-6}$ alkynyl, or —Z—$R^6$;

Z is a direct bond, $C_{1-6}$ alkyl or $C_{2-6}$ alkenyl;

$R^6$ is aryl, substituted aryl, $C_{3-6}$ cycloalkyl, or heteroaryl;

p is 0 or 1; and $R^x$ is $C_{1-6}$ alkyl optionally substituted with one to six same or different halogen atoms, $C_{3-6}$ cycloalkyl, $C_{2-6}$ alkenyl or hydroxy; or $R^x$ is a radical of the formula

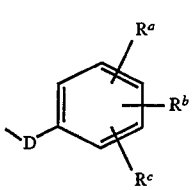

wherein D is a bond or $C_{1-6}$ alkyl; and $R^a$, $R^b$ and $R^c$ are independently hydrogen, amino, $C_{1-6}$ alkylamino, di-$C_{1-6}$alkylamino, halogen, $C_{1-6}$ alkyl, or $C_{1-6}$ alkoxy.

2. A compound of claim 1 wherein $R^{2'}$ is hydrogen, and $R^2$ is —$OCH_2OP(O)(OH)_2$; or a pharmaceutically acceptable salt thereof.

3. A compound of claim 2 wherein $R^1$ is hydroxy, —$OC(O)R^x$ or —$OC(O)OR^x$.

4. A compound of claim 3 wherein $R^x$ is $C_{1-6}$alkyl.

5. A compound of claim 3 wherein $R^3$ is hydrogen, hydroxy or acetoxy.

6. A compound of claim 3 wherein $R^4$ $(O)_p$ is phenyl or t-butoxy.

7. A compound of claim 3 wherein $R^5$ is phenyl, 2-furyl or 2-thienyl.

8. A compound of claim 1 which is 2'-O-(ethoxycarbonyl)-7-O-(phosphonooxymethyl)paclitaxel, or a pharmaceutically acceptable salt thereof.

9. The sodium salt of the compound of claim 8.
10. The triethanolamine salt of the compound of claim 8.
11. The triethylamine salt of the compound of claim 8.
12. The arginine salt of the compound of claim 8.
13. The lysine salt of the compound of claim 8.
14. The ethanolamine salt of the compound of claim 8.
15. The N-methylglucamine salt of the compound of claim 8.
16. A compound of claim 1 which is 7-O-(phosphonooxymethyl)paclitaxel, or a pharmaceutically acceptable salt thereof.
17. The sodium salt of the compound of claim 16.
18. A compound of claim 1 which is 3'-N-debenzoyl-3'-desphenyl-3'-N-(t-butyloxycarbonyl)-3'-(2-furyl)-2'-O-ethyloxycarbonyl-7-O-phosphonooxymethylpaclitaxel, or a pharmaceutically acceptable salt thereof.
19. The triethanolamine salt of the compound of claim 18.
20. A compound of claim 1 which is 3'-N-debenzoyl-3'-desphenyl-3'-N-(t-butyloxycarbonyl)-3'-(2-thienyl)-2'-O-ethyloxycarbonyl-7-O-phosphonooxymethylpaclitaxel or a pharmaceutically acceptable salt thereof.
21. The triethanolamine salt of the compound of claim 20.
22. A compound of claim 1 which is 2'-O-methoxycarbonyl-7-O-phosphonooxymethylpaclitaxel.
23. A compound of claim 1 which is 2'-O-methylcarbonyl-7-O-phosphonooxymethylpaclitaxel.
24. A compound of claim 1 which is 2'-O-n-propylcarbonyl-7-O-phosphonooxymethylpaclitaxel.
25. A compound of claim 1 wherein $R^1$ is —$OCH_2OP(O)(OH)_2$, or a pharmaceutically acceptable salt thereof.
26. A compound of claim 25 wherein $R^{2'}$ is hydrogen, $R^2$ is hydrogen, hydroxy or —$OC(O)OR^x$, and $R^x$ is as defined as claim 1.
27. A compound of claim 26 wherein $R^3$ is hydrogen, hydroxy or acetoxy.
28. A compound of claim 26 wherein $R^4(O)_p$ is phenyl or t-butoxy.
29. A compound of claim 26 wherein $R^5$ is phenyl.
30. A compound of claim 1 which is 2'-O-(phosphonooxymethyl)paclitaxel, or a pharmaceutically acceptable salt thereof.
31. A compound of claim 1 wherein $R^1$ and $R^2$ are both —$OCH_2OP(O)(OH)_2$, or a pharmaceutically acceptable salt thereof.
32. A compound of claim 1 which is 2',7-O-bis(phosphonooxymethyl)paclitaxel or a pharmaceutically acceptable salt thereof.
33. The sodium salt of the compound of claim 32.
34. A compound of claim 1 wherein $R^1$ is —$OCH_2OCH_2OP(O)(OH)_2$, or a pharmaceutically acceptable salt thereof.
35. A compound of claim 1 which is 2'-O-phosphonooxymethoxymethyl-7-O-phosphonooxymethylpaclitaxel.
36. A compound of claim 1 which is 2'-O-phosphonooxymethoxymethylpaclitaxel, or a pharmaceutically acceptable salt thereof.
37. The triethanolamine salt of the compound of claim 36.
38. A compound of claim 1 wherein $R^3$ is —$OCH_2OP(O)(OH)_2$, or a pharmaceutically acceptable salt thereof.
39. A compound of claim 1 which is 10-desacetyl-3'-N-desbenzoyl-3'-N-(t-butyloxycarbonyl)-10-O-(phosphonooxymethyl)paclitaxel, or a pharmaceutically acceptable salt thereof.
40. The triethanolamine salt of compound of claim 39.
41. A compound of claim 1 wherein $R^1$ is —$OCH_2OCH_2OCH_2OP(O)(OH)_2$.
42. A compound of claim 41 which is 2'-O-[(phosphonooxymethoxy)methoxymethyl]paclitaxel.
43. A compound of claim 41 which is 2'-O-[(phosphonooxymethoxy)methoxy]methyl-7-O-phosphonooxmethylypaclitaxel.

* * * * *